(12) United States Patent
Klein et al.

(10) Patent No.: US 10,449,311 B2
(45) Date of Patent: Oct. 22, 2019

(54) CONTROLLING ARTERIAL BLOOD GAS CONCENTRATION

(71) Applicant: THORNHILL SCIENTIFIC INC., Toronto (CA)

(72) Inventors: Michael Klein, Toronto (CA); Joseph Fisher, Thornhill (CA)

(73) Assignee: THORNHILL SCIENTIFIC INC., Toronto, Ontario (CA)

( * ) Notice: Subject to any disclaimer, the term of this patent is extended or adjusted under 35 U.S.C. 154(b) by 758 days.

(21) Appl. No.: 14/959,810

(22) Filed: Dec. 4, 2015

(65) Prior Publication Data

US 2016/0158481 A1 Jun. 9, 2016

Related U.S. Application Data

(63) Continuation of application No. PCT/CA2014/000473, filed on Jun. 3, 2014.
(Continued)

(51) Int. Cl.
*A61M 16/12* (2006.01)
*A61M 16/00* (2006.01)
(Continued)

(52) U.S. Cl.
CPC ......... *A61M 16/0051* (2013.01); *A61B 5/087* (2013.01); *A61M 16/026* (2017.08);
(Continued)

(58) Field of Classification Search
CPC .............. A61M 16/00; A61M 16/0003; A61M 16/0051; A61M 16/0057; A61M 16/022;
(Continued)

(56) References Cited

U.S. PATENT DOCUMENTS 4,326,513 A * 4/1982 Schulz ................. A61M 16/00
128/203.14
5,558,083 A 9/1996 Bathe et al.
(Continued)

FOREIGN PATENT DOCUMENTS

WO 2007012197 A1 2/2007
WO 2011143751 A1 11/2011
(Continued)

OTHER PUBLICATIONS

Mark, Clarisse I., et al. "Precise control of end-tidal carbon dioxide and oxygen improves BOLD and ASL cerebrovascular reactivity measures." Magnetic resonance in medicine 64.3 (2010): 749-756.*
(Continued)

*Primary Examiner* — Joseph D. Boecker
(74) *Attorney, Agent, or Firm* — Perry + Currier Inc

(57) ABSTRACT

A system for controlling an amount of at least one gas X in a subject's lung to target at least one end tidal partial pressure of at least one gas X ($PetX^T$) uses a control system for controlling the gas delivery device, wherein the control system implements a sequential gas delivery system and a feedback algorithm which compares a $PetX^T$ for a respective breath of variable size and preferably a respective current PetX value measured by a measurement system, to obtain an error signal, the feedback algorithm adapted for generating a control signal based on the error signal, the control signal determining the amount of gas X to be inspired by the subject in at least a first portion of a respective ensuing respective inspiratory cycle to target $PetX^T$ for the respective interval.

13 Claims, 37 Drawing Sheets

Related U.S. Application Data

(60) Provisional application No. 61/831,492, filed on Jun. 5, 2013.

(51) Int. Cl.
*G06F 19/00* (2018.01)
*A61B 5/087* (2006.01)

(52) U.S. Cl.
CPC ......... *A61M 16/12* (2013.01); *G06F 19/3481* (2013.01); *A61M 2205/50* (2013.01); *A61M 2230/432* (2013.01); *A61M 2230/435* (2013.01); *A61M 2230/437* (2013.01)

(58) Field of Classification Search
CPC .............. A61M 16/024; A61M 16/026; A61M 2016/0027; A61M 2230/202; A61M 2230/43; A61M 2230/432; A61M 2230/435; A61M 2230/437; A61M 2205/50; A61B 5/087; A61B 5/091; A61B 5/097
See application file for complete search history.

(56) References Cited

U.S. PATENT DOCUMENTS

| | | | |
|---|---|---|---|
| 6,799,570 B2 | 10/2004 | Fisher et al. | |
| 7,959,443 B1* | 6/2011 | Frembgen | G09B 23/32 434/262 |
| 2002/0185129 A1 | 12/2002 | Fisher et al. | |
| 2005/0109340 A1 | 5/2005 | Tehrani | |
| 2007/0044805 A1* | 3/2007 | Wedler | A61M 16/024 128/207.14 |
| 2007/0062534 A1 | 3/2007 | Fisher et al. | |
| 2009/0120435 A1* | 5/2009 | Slessarev | A61M 16/0051 128/203.14 |
| 2012/0215124 A1 | 8/2012 | Fisher et al. | |
| 2014/0311491 A1* | 10/2014 | Klein | A61B 5/083 128/204.22 |
| 2015/0114394 A1* | 4/2015 | Klein | A61M 16/026 128/203.25 |

FOREIGN PATENT DOCUMENTS

| | | |
|---|---|---|
| WO | 2012139204 A1 | 10/2012 |
| WO | 2012151583 A1 | 11/2012 |
| WO | 2013082703 A1 | 6/2013 |
| WO | 2013138910 A1 | 9/2013 |
| WO | 2013163735 A1 | 11/2013 |

OTHER PUBLICATIONS

International Search Report on corresponding PCT application (PCT/CA2014/000473) from International Searching Authority (CIPO) dated Aug. 19, 2014.

\* cited by examiner

| Subject | No SGD | | | | SGD | | | |
| --- | --- | --- | --- | --- | --- | --- | --- | --- |
| | RMS | SD | MIN | MAX | RMS | SD | MIN | MAX |
| 1 | 1.11 | 1.11 | -4.20 | 3.80 | 0.29 | 0.29 | -1.00 | 0.90 |
| 2 | 1.94 | 1.94 | -11.00 | 6.20 | 0.28 | 0.28 | -1.10 | 1.20 |
| 3 | 4.05* | 4.04* | -14.80* | 7.30* | 0.75 | 0.75 | -3.20 | 1.90 |

*test was terminated early

Fig. 7

| Stage | Ventilation | Target PetCO2 (mmHg) | Duration (min) |
|---|---|---|---|
| A | Natural | 55 | 1 |
| B | Hyperventilation | 55 | 0.5 |
| C | Natural | 55 | 0.5 |
| D | Hyperventilation | 55 | 0.5 |
| E | Natural | 55 | 0.5 |
| F | Alternating between hyperventilation and natural breathing each breath | 55 | 1 |
| G | Natural | 60 | 5 |
| H | Natural | Alternating between 55 and 60 every 0.5 min | 2 |

Fig. 8g

Apparatus

Definitions of abbreviated terms

| Term | Units | Definition |
|---|---|---|
| $n$ | | Total number of breaths in the target sequence |
| $i$ | | Index of breath number in the target sequence |
| $P_{ET}O2[i]^T$ | mmHg | Target end-tidal partial pressure of O2 during breath $i$ |
| $P_{ET}CO2[i]^T$ | mmHg | Target end-tidal partial pressure of CO2 during breath $i$ |
| $P_{ET}O2[i]^M$ | mmHg | Measured end-tidal partial pressure of O2 during breath $i$ |
| $P_{ET}CO2[i]^M$ | mmHg | Measured end-tidal partial pressure of CO2 during breath $i$ |
| $pH[i]$ | | pH of pulmonary end-capillary blood during breath $i$ |
| $[HCO_3]$ | mmol/L | Bicarbonate concentration of the blood throughout the circulation |
| $P_pO2[i]$ | mmHg | Partial pressure of O2 in the pulmonary end-capillary blood during breath $i$ |
| $P_pCO2[i]$ | mmHg | Partial pressure of CO2 in the pulmonary end-capillary blood during breath $i$ |
| $T$ | C | Body temperature |
| $S_pO2[i]$ | % | O2 saturation of the pulmonary end-capillary blood during breath $i$ |
| $Hb$ | g/dL | Concentration of haemoglobin in the blood throughout the circulation |
| $C_pO2[i]$ | ml/dL | O2 content of the pulmonary end-capillary blood during breath $i$ |
| $C_pCO2[i]$ | ml/dL | CO2 content of the pulmonary end-capillary blood during breath $i$ |

Fig. 21

| | | |
|---|---|---|
| $C_aO2[i]$ | ml/dL | O2 content of the arterial blood during breath $i$ |
| $C_aCO2[i]$ | ml/dL | CO2 content of the arterial blood during breath $i$ |
| $C_{MV(T)}O2[i]$ | ml/dL | O2 content of the mixed-venous blood leaving the tissues during breath $i$ |
| $C_{MV(T)}CO2[i]$ | ml/dL | CO2 content of the mixed-venous blood leaving the tissues during breath $i$ |
| $C_{MV}O2[i]$ | ml/dL | O2 content of the mixed-venous blood entering the pulmonary circulation during breath $i$ |
| $C_{MV}CO2[i]$ | ml/dL | CO2 content of the mixed-venous blood entering the pulmonary circulation during during breath $i$ |
| $s$ | %/100 | Intrapulmonary shunt fraction |
| $Q$ | dL/min | Cardiac output |
| $T_B$ | min | Breath period |
| $VO2$ | ml/min | Overall metabolic consumption of O2 |
| $VCO2$ | ml/min | Overall metabolic production of CO2 |
| $n_{O2}$ | | Total number of compartments in the model of O2 in the tissues |
| $j$ | | Index of the compartments in the model of O2 in the tissues |
| $vo2_j$ | %/100 | Fraction of the overall metabolic consumption of O2 assigned to compartment $j$ of the model of O2 in the tissues |
| $q_j$ | %/100 | Fraction of the overall cardiac output assigned to compartment $j$ of the model of O2 in the tissues |
| $dO2_j$ | ml | Storage capacity for O2 of compartment $j$ of the model of |

Fig. 21 – (continued)

| | | |
|---|---|---|
| | | O2 in the tissues |
| $n_{CO2}$ | | Total number of compartments in the model of CO2 in the tissues |
| $k$ | | Index of the compartments in the model of CO2 in the tissues |
| $vco2_k$ | %/100 | Fraction of the overall metabolic production of CO2 assigned to compartment $k$ of the model of CO2 in the tissues |
| $q_k$ | %/100 | Fraction of the overall cardiac output assigned to compartment $k$ of the model of CO2 in the tissues |
| $dCO2_k$ | ml | Storage capacity for CO2 of compartment $k$ of the model of CO2 in the tissues |
| SGDC | | Sequential gas delivery circuit |
| PT | | Pressure transducer |
| GA | | O2/CO2 gas analyzer |
| DX | | Display |
| CPU | | Computer |
| ID | | Input device |
| GB | | Gas blender |
| FT | | Flow transducer |
| $G_i$ | | The controlled gas mixture inspired by the subject |

Fig. 21 – (continued)

| | | |
|---|---|---|
| $G_2$ | | Neutral gas inspired by the subject |
| $FG_1$ | ml/min | Rate at which the controlled gas mixture ($G_1$) is made available for inspiration |
| $VG_1$ | ml | Average volume of the controlled gas mixture ($G_1$) inspired into the alveoli per breath |
| $VG_2$ | ml | Average volume of neutral gas ($G_2$) inspired into the alveoli per breath |
| $V_T$ | ml | Tidal volume |
| $V_D$ | ml | Anatomical dead space |
| $P_I O2[i]$ | mmHg | Partial pressure of O2 in the controlled gas mixture ($G_1$) during breath $i$ |
| $P_I CO2[i]$ | mmHg | Partial pressure of CO2 in the controlled gas mixture ($G_1$) during breath $i$ |
| $F_I O2[i]$ | %/100 | Fractional concentration of O2 in the controlled gas mixture ($G_1$) during breath $i$ |
| $F_I CO2[i]$ | %/100 | Fractional concentration of CO2 in the controlled gas mixture ($G_1$) during breath $i$ |
| $FRC$ | ml | Functional residual capacity |
| $W$ | kg | Subject weight |
| $H$ | m | Subject height |
| $A$ | years | Subject age |
| $G$ | male/female | Subject sex |
| $n_R$ | # breaths | Recirculation time |

Fig. 21 – (continued)

| | | |
|---|---|---|
| $PB$ | mmHg | Barometric pressure |
| $n_{SG}$ | | Total number of source gases blended to create the controlled gas mixture |
| $m$ | | Index of source gases blended to create the controlled gas mixture |
| $SG_m$ | | Source gas $m$ blended to create the controlled gas mixture |
| $FSG_m[i]$ | ml/min | Flow rate of source gas $m$ ($SG_m$) during breath $i$ |
| $fo2_m$ | %/100 | Fractional concentration of O2 in source gas $m$ ($SG_m$) |
| $fco2_m$ | %/100 | Fractional concentration of CO2 in source gas $m$ ($SG_m$) |
| $P_{ET}O2_0^M$ | mmHg | Baseline/resting measured end-tidal partial pressure of O2 |
| $P_{ET}CO2_0^M$ | mmHg | Baseline/resting measured end-tidal partial pressure CO2 |
| $VB_{O2}[i]$ | ml | The volume of O2 transferred between the alveolar space and the pulmonary circulation during breath $i$ |
| $VB_{CO2}[i]$ | ml | The volume of CO2 transferred between the alveolar space and the pulmonary circulation during breath $i$ |
| $\alpha$ | ml/mmHg | Correction factor for tuning the estimate of the functional residual capacity ($FRC$) |
| $\beta$ | ml/min/mmHg | Correction factor for tuning the overall metabolic production of O2 ($VO2$) |
| $\gamma$ | ml/min/mmHg | Correction factor for tuning the overall metabolic consumption of CO2 ($VCO2$) |

Fig. 21 – (continued)

| Starting PCO2 (mm Hg) | 1st Baseline (40mm Hg) | 1st Step (50 mm Hg) | 2nd Baseline (40mm Hg) | 2nd Step (50 mm Hg) | 3rd Baseline (40mm Hg) | Delta PCO2 First step | Delta PCO2 second step |
|---|---|---|---|---|---|---|---|
| 40 | 40 | 50 | 41 | 50 | 40 | 10 | 9 |
| 39 | 39 | 49 | 40 | 49 | 40 | 10 | 9 |
| 41 | 41 | 49 | 42 | 50 | 41 | 8 | 8 |
| 40 | 39 | 48.5 | 40 | 49 | 40 | 9 | 9 |
| 35 | 39 | 48 | 40 | 48 | 40 | 9 | 8 |
| 40 | 39 | 48 | 39 | 49 | 40 | 9 | 10 |

Fig. 25

CONTROLLING ARTERIAL BLOOD GAS CONCENTRATION

CROSS-REFERENCE TO RELATED APPLICATIONS

This application is a Continuation of co-pending International Application No. PCT/CA2014/000473, filed Jun. 3, 2014, the disclosure of which is incorporated herein by reference. This application further claims the benefit, under 35 U.S.C. § 119(e), of U.S. Provisional Application No. 61/831,492, filed Jun. 5, 2013, the disclosure of which is incorporated herein by reference.

FIELD OF THE INVENTION

The present invention relates to a system, method and apparatus for controlling arterial blood gas concentrations of one or more gases.

BACKGROUND OF THE INVENTION

Techniques for controlling end-tidal partial pressures of carbon dioxide, oxygen and other gases are gaining increasing importance for a variety of research, diagnostic and medicinal purposes. Methods for controlling end tidal pressures of gases have gained particular importance as a means for manipulating arterial levels of carbon dioxide (and also oxygen), for example to provide a controlled vasoactive stimulus to enable the measurement of cerebrovascular reactivity (CVR) e.g. by MRI.

Conventional methods of manipulating arterial carbon dioxide levels such as breath holding, hyperventilation and inhalation of fixed concentration of carbon dioxide balanced with medical air or oxygen are deficient in their ability to rapidly and accurately attain targeted arterial carbon dioxide partial pressures for the purposes of routinely measuring vascular reactivity in a rapid and reliable manner.

The end-tidal partial pressures of gases are determined by the gases inspired into the lungs, the mixed venous partial pressures of gases in the pulmonary circulation, and the exchange of gases between the alveolar space and the blood in transit through the pulmonary capillaries. Changes in the end-tidal partial pressures of gases are reflected in the pulmonary end-capillary partial pressures of gases, which in turn flow into the arterial circulation. The gases in the mixed-venous blood are determined by the arterial inflow of gases to the tissues and the exchange of gases between the tissue stores and the blood, while the blood is in transit through the tissue capillary beds.

In the simplest approaches, manipulation of the end-tidal partial pressures of gases has been attempted with fixed changes to the composition of the inspired gas. However, without any additional intervention, the end-tidal partial pressures of gases vary slowly and irregularly as exchange occurs at the lungs and tissues. Furthermore, the ventilatory response to perturbations in the end-tidal partial pressures of gases is generally unpredictable and potentially unstable. Often, the ventilatory response acts to restore the condition of the blood to homeostatic norms. Therefore, any changes in the end-tidal partial pressures of gases are immediately challenged by a disruptive response in the alveolar ventilation. Consequently, fixed changes in the inspired gas composition provoke only slow, irregular, and transient changes in blood gas partial pressures.

In more complex approaches, manipulation of the end-tidal partial pressures of gases has been attempted with negative feedback control. This approach continuously varies the composition of the inspired gas so as to minimize error between measured and desired end-tidal partial pressures of gases. Technically, such systems suffer from the same limitations as all negative feedback control systems—an inherent trade-off between response time and stability. For example, to generate a transition (e.g. a 10 mm. Hg increase) in PetCO2 for imaging vascular reactivity of the heart (e.g. by MRI) rapid transition times can be commercially vital but augmenting transition time cannot be done at the expense of stability. Stability may also be affected by irregular breathing in response to exercise, in response to positioning of a subject on a medical examination table or as a result of stresses arising during the course of a diagnostic procedure in which control of blood gas concentration is used as a stimulus. Notably, elevating the partial pressure of $CO_2$ (and to some extent oxygen) causes hyperventilation which in turn affects stability. Consequently, there is a need to overcome previous limitations in end-tidal gas control, allowing for more precise and rapid execution of end tidal gas targeting sequences in a wide range of subjects and environments.

SUMMARY OF THE INVENTION

The present invention is particularly directed to targeting a partial pressure of at least one gas X ($PetX^T$) in a mammal's arterial blood in circumstances in which the subject's tidal volume is of variable size from breath to breath such that the amount of a gas of requisite composition to attain the target arterial partial pressure of gas X that will prove to be inhaled by the subject in any respective breath is not predictable in advance, for example in most circumstances where the subject is not breathing on a ventilator that is controlling the subject's tidal volume. Accordingly such tidal volumes may be of variable size from breath to breath, as in the common case of a spontaneously breathing subject.

For present purposes a surrogate measure of the subject's arterial partial pressure of gas X in the form of the subject's end tidal partial pressure of gas X ($P_{ET}X$) is deemed to be a sufficiently closely approximation of the arterial value inasmuch as the end tidal expired gas is a gas of composition which has substantially equilibrated with blood leaving the lung and entering the systemic circulation.

Erratic breathing is not uncommon in subjects compelled to breath via a gas delivery device, as discussed below. The present inventors have developed a new method and apparatus for more rapidly and accurately targeting and maintaining an end tidal partial pressure of a gas X in a subject's lung in circumstances in which tidal volume from breath to breath is unpredictable and potentially highly erratic. Accordingly, it is now possible to more effectively target a partial pressure of at least one gas X in a spontaneously breathing subject's arterial blood across the range of scenarios and varied subject responses which potentially encompass highly erratic breathing.

Breath size is considered to be variable if it varies unpredictably, for example, for purposes herein in a manner or to an extent which cannot, in the existing circumstances, be described as insignificant. Methods of mechanical ventilation, for example, that do not control breath size are amenable to such an advantageous method of targeting.

The present invention is corroborated by the discovery, in human clinical testing, that a target end tidal concentration of a gas X can be attained and maintained in a spontaneously breathing subject using a negative feedback algorithm despite substantial unpredictable changes in the subject's minute ventilation. This clinical study demonstrates that the inherent trade-off between response time and stability in targeting a particular end tidal concentration of a gas X, using negative feedback control, can be substantially mitigated using sequential gas delivery (SGD) in subjects responding variously to test conditions, the foregoing despite a given subject's changing response to the type of gas being delivered (e.g. where gas X is carbon dioxide subjects will tend to hyperventilate to greater or lesser extents) or the possible amplitude or such change having regard the nature of the diagnostic or therapeutic protocol. For example, the stress of breathing through an apparatus and/or the stress associated with being confined or otherwise discomforted in an imaging device (not measured in this study) and/or the stress or pain associated with receiving therapy (not measured in this study). Indeed, this advantage has been determined to be appreciable despite highly erratic breathing and even when a prospective or feed-forward model is used as an aid to reduce the variability achievable with negative feedback alone in attaining the target end tidal partial pressure of gas X.

The study data presented herein shows that fluctuation from a targeted end tidal $PCO_2$ was significantly less using SGD than without using SGD under conditions in which breath size of subject was substantially varied in a series of breaths over time.

Accordingly, in respective aspects, the invention is directed to one of a method, system, computer program product, IC chip (e.g. a programmable chip) and apparatus for targeting a partial pressure of at least one gas X ($PetX^T$) in a spontaneously breathing mammal's (subject's) arterial blood (optionally using end tidal values as preferred non-invasive surrogate measures of the actual arterial values) as well as to a method of controlling a gas delivery device (for respiratory gas delivery) such as a gas blender.

It should be appreciated that the same end tidal partial pressure of gas X may be targeted for a series of successive breaths. Therefore, the term "targeting" or "for attaining" or "to attain" or "attainable" (terms used interchangeably) implies that a some particular value for $PetX^T$ will be targeted, optionally on a breath by breath basis, whether or not the target for a respective breath [i] is the same or different, higher or lower. Therefore the term "to attain" or "target" and related terms encompass an often important goal maintaining a particular target end tidal partial pressure of gas X from breath to breath or interval to interval. It should also be appreciated that logistically attainable target partial pressures for several gases may in principle be targeted independently of one another. A predictive algorithm can be employed to discern logistically attainable targets which are relatively extreme; non-extreme values for logistically attainable target partial pressures for one or more gases will be known to persons skilled in the art as a matter of experience with the subject matter of the invention.

Those skilled in the art will also appreciate that increasing a target end tidal partial pressure of a gas X may require delivery of a gas containing a computed amount or concentration of gas X and that the control system may direct reduction in the concentration of a gas X to obtain a lower partial pressure of gas X by sending a signal to the flow controller to deliver a gas containing a low concentration or 0% of gas X for one or more breaths. This should be appreciated as well in the particular context in which gas X is a gas produced or consumed by the body (e.g carbon dioxide, oxygen, an anesthetic etc). It should also be appreciated that a spontaneously breathing subject may be asked to hyperventilate or hypoventilate "to attain" (i.e. "with the goal of attaining") a reduced partial pressure of a gas X more quickly or slowly and that a subject's spontaneous ventilation may be assisted mechanically in a manner known to those skilled in the art, particularly in a manner or to an extent that breath size for the duration in question is variable and unpredictable.

According to one aspect, the invention is directed to a method for targeting at least one partial pressure of at least one gas X ($PetX^T$) in a subject, optionally in a spontaneously breathing mammal's blood, comprising, with respect to a series of respective breaths [i]:

(A) making available to a subject a first gas in the first part of a respective breath [i] and a neutral second gas (e.g. a gas having a partial pressure of gas X which equals the measured end tidal concentration of gas X in an immediately preceding breath or equals $PetX^T$ targeted in the current respective breath [i]), in the second part of a respective breath [i], wherein the amount of neutral gas received in a respective breath [i] at least equals or preferably exceeds the dead space volume of the subject's lung; and (B) using a feedback control algorithm to:

(i) obtain, on a breath by breath basis, a measured value corresponding, at least approximately, to the arterial partial pressure of gas X after gas exchange in a previous breath (preferably breath [i−1]);

(ii) based on the measured value, compute an error signal with respect to $PetX^T$ for the respective breath [i]; and (iii) generate a control signal based on the error signal that determines the amount of gas X needed to be inspired by the subject in the first gas to target $PetX^T$ for the respective breath [i].

Optionally, the method is employed to conduct clinical testing in a mammal.

Optionally, the method is directed to enhancing a non-therapeutic diagnostic procedure, optionally an imaging procedure, the imaging procedure optionally exploiting a high resolution imaging modality, for example an MRI-based imaging modality.

Optionally, the method is employed in a therapeutic procedure.

Optionally, the method is employed to control a gas delivery device in the form of a gas blender adapted for delivering a respiratory gas to a mammal.

The gas delivery device optionally comprises a measurement system for measuring the concentration of gas X in a subject's end tidal exhaled breath (arterial blood gases can also be measured directly in blood but such methods, although encompassed herein, are typically invasive) and a flow controller for controlling a gas delivery the concentration of gas X in a gas inhaled by the subject in a respective breath [i].

Optionally, the amount of gas X required to be inspired by the subject the first portion of a respective breath [i] to target the $PetX^T$ for a respective interval or breath is also determined prospectively based on a predictive algorithm. Optionally, the feedback control signal is added to the control signal generated as a result of the prospective determination.

Optionally, the amount of gas X required to be inspired by the subject in at least a first portion of a respective breath [i] to target the $PetX^T$ for a respective interval is determined prospectively, on a breath by breath basis.

The invention encompasses any robust feedback control algorithm known to those skilled in the art. Optionally, the feedback control signal is generated using a feedback control algorithm selected from a group comprising a PD, a PI and a PID control algorithm.

Optionally, the predictive algorithm (an example of which is more fully described with reference to Section C hereinbelow) is executed by:

a. obtaining input of the concentration of gas X in the mixed venous blood entering the subject's pulmonary circulation for gas exchange in one or more respective breaths [i] ($C_{MV}X[i]$);

b. obtaining input of a logistically attainable end tidal partial pressure of gas X ($PetX[i]^T$) for a respective breath [i];

c. obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation.

Optionally, the mass balance equation is computed based on a tidal model of the lung.

Optionally, the mass balance equation is computed in terms of discrete respective breaths [i] including one or more discrete volumes comprising or corresponding to a subject's FRC, anatomic dead space, a volume of gas transferred between the subject's lung and pulmonary circulation in the respective breath [i] and an individual tidal volume of the respective breath [i].

Optionally, a concentration of gas X ($F_IX$) in the first inspired gas is computed from the mass balance equation to target or attain a $PetX[i]^T$ in a respective breath [i].

Optionally, the mass balance equation is solved for $F_IX$.

Optionally, the predictive algorithm obtains inputs required to compute an $F_IX$ to target $PetX[i]^T$ for a respective breath [i], wherein $F_IX$ is computed prospectively using a mass balance equation which comprises terms corresponding to optionally all the terms in:

$$F_IX[i] = \frac{(P_{ET}X[i]^T - P_{ET}X[i-T]^T) \cdot (FRC + V_T) + P_{ET}X[i-1]^T \cdot (FG_1 \cdot T_B) - PB \cdot Q \cdot (1-s) \cdot T_B \cdot (C_{MV}X[i] - C_pX[i])}{FG_1 \cdot T_B \cdot P_B} \quad \text{eq. 1}$$

or $$F_IX[i] = \frac{P_{ET}X[i]^T \cdot (FRC + V_T) - P_{ET}X[i-1]^T \cdot (FRC + V_D) - PB \cdot Q \cdot (1-s) \cdot T_B \cdot (C_{MV}X[i] - C_pX[i])}{(V_T - V_D) \cdot PB} \quad \text{eq. 2}$$

It may be appreciated (as more fully discussed below) that some of these terms might be considered by those practicing the invention to exert minor effects on the targeting outcome, depending on which term and the circumstances including the degree to which accuracy is required, whether a smaller or large target change in arterial partial pressure of gas X is sought, the identity of gas X and it's importance in the testing procedure, whether a particular target is being maintained (at one extreme) and whether a rapid transition to one or several new targets, in rapid succession, is being sought (at the other extreme) as well as other factors affecting how well the hardware and negative feedback system function is a given situation. Accordingly, the invention contemplates that accounting only for an application or situation specific subset of the terms in the equations will still provide a useful predictive model for attaining one or more target end tidal concentration of gas X.

The invention is also directed to a computer program product and an IC chip for targeting at least one partial pressure of at least one gas X ($PetX^T$) in a subject, optionally in a spontaneously breathing mammal's blood, comprising, with respect to a series of respective breaths [i], machine readable code for:

(A) making available to a subject a first gas in the first part of a respective breath [i] and one of a neutral second gas and a gas having a partial pressure of gas X which equals $PetX^T$ targeted in the respective breath [i], in the second part of a respective breath [i], wherein the amount of neutral gas (i.e. neutral with respect to the previous breath or the current breath, as explained below) received in a respective breath [i] at least equals or preferably exceeds the dead space volume of the subject's lung; and (B) using a feedback control algorithm to:
(i) obtain, on a breath by breath basis, a measured value corresponding, at least approximately, to the arterial partial pressure of gas X after gas exchange in a previous breath (preferably breath [i−1]);
(ii) based on the measured value, compute an error signal with respect to $PetX^T$ for the respective breath [i]; and
(iii) generate a control signal based on the error signal that determines the amount of gas X needed to be inspired by the subject in the first gas to target $PetX^T$ for the respective breath [i].

Optionally, a method, computer program product, IC chip, system or apparatus of the invention are employed as enhanced research tools.

In an apparatus, for example a gas delivery device including a measurement system, the control system of the apparatus is typically implemented by a computer, the computer typically configured to provide output signals to one or more rapid flow controllers based on input from the measurement system.

Optionally, the gas delivery device is a gas blender and the measurement system includes at least one flow sensor positioned to measure flow of an inspiratory gas stream to a subject and wherein the gas blender is controlled to add a variable amount of a gas containing a gas X to the inspiratory gas stream based on measurements obtained from the flow sensor to deliver an amount of gas X required to be inspired by the subject to target the $PetX^T$ for a respective interval.

The breathing circuit may a physical SGD circuit in which the subject inhales neutral gas in the second part of a respective breath [i] in the form of gas exhaled by the subject's in a previous breath or alternatively an SGD circuit may be constituted by a virtual SGD circuit which may employ a conventional breathing circuit.

For the purposes of the present invention, the term neutral gas includes gas having a partial pressure of gas X which is the same at the partial pressure of gas X at the end of a previous breath, preferably the immediately preceding breath. An alternative to delivering this neutral gas from a previous breath as the second gas (the gas delivered for the remainder of a respective breath [i]) is delivering a gas having the targeted end tidal partial pressure of gas X for the respective breath [i] in question which is "neutral" with respect the current breath in contrast to the previous breath.

Optionally, the method is employed to control a gas delivery device e.g. in the form of a gas blender adapted for delivering a respiratory gas to a mammal, the steps of this method optionally including:

a) measuring for a respective breath [i] the concentration of the at least one gas X in a subject's expired gas in a previous breath;

b) making available to a subject, for inspiration in a respective breath [i], a first gas and a second gas which is one of a neutral gas and a gas having a partial pressure of gas X which equals $PetX^T$ targeted in the respective breath [i], such that when the subject's minute ventilation exceeds the fresh gas available for a breath, the second gas is delivered for the remainder of the breath;

c) computing an error signal based on $PetX^T$ for the respective breath [i] and a measured value of the concentration of gas X in the subject's end tidal expired gas for the previous breath [i−1];

d) generating a control signal based on the error signal that determines the amount of gas X needed to be inspired by the subject in first gas to target $PetX^T$ for the respective breath [i].

Irrespective of whether the breathing circuit is a physical sequential gas delivery circuit or a virtual sequential gas delivery circuit, ensuring that the subject (mammal) gets a volume of neutral gas which substantially equals and preferably exceeds its dead space volume (since breath sizes varies it is better to exceed the dead space volume by a safe margin) better ensures that the entirety of the first gas participates in gas exchange. This is optionally accomplished by setting the flow of the first gas into the breathing circuit to be equal to or less (preferably) than the subject's baseline minute ventilation minus the subject's anatomic dead space ventilation, so that the entire volume of the first gas controls enters the alveolar space and participates in gas exchange.

The term sequential gas delivery and by extension circuits adapted or used for this purpose are defined below in Section C under a separate heading and in connection with Section B which explains virtual sequential gas delivery.

In one aspect, the invention is directed to a method for targeting an end tidal partial pressure of a gas X ($PetX^T$) in a respective breath [i], comprising, with respect to a respective breath [i]:

a) measuring at least at the end of at least one previous breath, the concentration of the at least one gas X in a subject's expired gas to obtain a measured value of the concentration of gas X in the subject's end tidal expired gas in the previous breath, preferably the previous breath is the immediately preceding breath [i−1];

b) setting the flow of the first gas into the breathing circuit to be equal to or less than the subject's baseline minute ventilation minus the subject's anatomic dead space ventilation;

c) making available to a subject, for inspiration a first gas and a second gas, such that when the subject's minute ventilation exceeds the fresh gas available for a breath, the second gas is delivered for the remainder of the breath;

wherein the first gas has a partial pressure of a gas X (PX) computed using a feedback algorithm which compares a $PetX^T$ for a respective breath [i] and the measured value of the concentration of gas X in the subject's end tidal expired gas to obtain an error signal, the feedback algorithm adapted for generating a control signal based on the error signal that determines the amount of gas X needed to be inspired by the subject in first gas to target $PetX^T$ for the respective breath [i]; and wherein the second gas is one of a neutral gas (optionally a gas which has a (PX) approximating the PX in the subject's arterial blood after the immediately preceding breath) and the $PetX^T$ for the current respective breath [i]).

Optionally the method employs a sequential gas delivery breathing circuit.

Optionally, the method employs a virtual sequential gas algorithm as hereinafter described.

Optionally, the gas X is carbon dioxide.

Optionally, the imaging procedure measures a vascular response to vasoactive amount of carbon dioxide, optionally a vasodilatory amount of carbon dioxide.

Optionally, the partial pressures of a plurality of gases are controlled; optionally a plurality of gases comprising at least one of carbon dioxide and oxygen.

In another aspect, the invention is directed to a method for enhancing a non-therapeutic diagnostic imaging procedure in a subject, wherein the method involves targeting at least one end tidal partial pressure of a gas X ($PetX^T$) in a respective breath [i], optionally to produce a vasoactive response, comprising, with respect to a respective breath [i]:

a) measuring at least at the end of at least one previous breath, the concentration of the at least one gas X in a subject's expired gas to obtain a measured value of the concentration of gas X in the subject's end tidal expired gas in the previous breath, preferably the previous breath is the immediately preceding breath [i−1];

b) setting the flow of the first gas into the breathing circuit to be equal to or less than the subject's baseline minute ventilation minus the subject's anatomic dead space ventilation;

c) making available to a subject, for inspiration a first gas and a second gas, such that when the subject's minute ventilation exceeds the fresh gas available for a breath, the second gas is delivered for the remainder of the breath;

wherein the first gas has a partial pressure of a gas X (PX) computed using a feedback algorithm which compares a $PetX^T$ for a respective breath [i] and the measured value of the concentration of gas X in the subject's end tidal expired gas to obtain an error signal, the feedback algorithm adapted for generating a control signal based on the error signal that determines the amount of gas X needed to be inspired by the subject in first gas to target $PetX^T$ for the respective breath [i];

and wherein the second gas is one of a neutral gas (optionally a gas which has a (PX) approximating the PX in the subject's arterial blood after the immediately preceding breath) and the $PetX^T$ for the current respective breath [i].

Preferably, $PetX^T$ is targeted in each of a series successive breaths i, i+1 . . . i+n preceding the capture of a respective image and optionally for the duration in which the respective image is captured.

In yet another aspect, the invention is directed to a method for controlling a gas delivery device to target an end tidal partial pressure of a gas X ($PetX^T$) in a respective breath [i], the gas delivery device operatively connected to a breathing circuit, the method comprising, with respect to a respective breath [i]:

a) measuring at least at the end of at least one previous breath, the concentration of the at least one gas X in a subject's expired gas to obtain a measured value of the concentration of gas X in the subject's end tidal expired gas in the previous breath, preferably the previous breath is the immediately preceding breath [i−1];

b) setting the flow of the first gas into the breathing circuit to be equal to or less than the subject's baseline minute ventilation minus the subject's anatomic dead space ventilation;

c) making available to a subject, for inspiration a first gas and a second gas, such that when the subject's minute ventilation exceeds the fresh gas available for a breath, the second gas is delivered for the remainder of the breath; wherein the first gas has a partial pressure of a gas X (PX) computed using a feedback algorithm which compares a $PetX^T$ for a respective breath [i] and the measured value of the concentration of gas X in the subject's end tidal expired gas to obtain an error signal, the feedback algorithm adapted for generating a control signal based on the error signal that determines the amount of gas X needed to be inspired by the subject in first gas to target $PetX^T$ for the respective breath [i];
and wherein the second gas is one of a neutral gas, optionally a gas which has a (PX) approximating the PX in the subject's arterial blood after the immediately preceding breath, and the $PetX^T$ for the current respective breath [i].

According to yet another aspect, the invention is directed to an apparatus for attaining a target partial pressure of at least one gas X ($PetX^T$) in a spontaneously breathing mammal's blood, comprising:
(1) a gas delivery device configured for connection to a breathing circuit;
(2) a control system;
(3) a measurement system configured to obtain a value which represents an approximation of the partial pressure of the at least one gas X in the subject's arterial blood after gas exchange in a previous breath, optionally the concentration of the at least one gas X in a subject's end tidal expired gas after gas exchange in breath [i−1];
wherein the control system is configured, with respect to a series of respective breaths [i]
(A) to make available to a subject a first gas in the first part of a respective breath [i] and a neutral second gas in the second part of a respective breath [i], such that the amount of neutral gas received in a respective breath [i] at least equals and preferably exceeds the dead space volume;
(B) to use a feedback control algorithm to:
(i) obtain, on a breath by breath basis, the measured value corresponding, at least approximately, to the arterial partial pressure of gas X after gas exchange in a previous breath (preferably breath [i−1]);
(ii) based on the measured value, compute an error signal with respect to $PetX^T$ for the respective breath [i]; and
(iii) generate a control signal based on the error signal that determines the amount of gas X needed to be inspired by the subject in the first gas to target $PetX^T$ for the respective breath [i].

The invention is also directed to an apparatus for targeting an end tidal partial pressure of a gas X ($PetX^T$), optionally in a spontaneously breathing mammal, comprising:
(1) a gas delivery device configured for connection to a breathing circuit;
(2) a measurement system configured for measuring the concentration of the at least one gas X in a subject's end tidal expired gas;
(3) a control system for controlling the gas delivery device, wherein the control system is configured to target a $PetX^T$ for a series of respective inspiratory cycles of potentially variable length, the control system including a processor configured, for a respective breath [i]:
  A. to obtain input of at least one logistically attainable $PetX^T$ value;
  B. to obtain input from the measurement system of at least one measured value corresponding to the subject's current arterial blood concentration of gas X (e.g. $PaCO_2$), optionally the end tidal partial of gas X (PetX) attained as a result of gas exchange in a previous breath, preferably the immediately preceding respective breath [i−1];
  C. to determine of an amount of gas X required to be inspired by the subject in at least a first portion of an inspiratory cycle of a respective breath [i] to target the $PetX^T$ for a respective interval, the gas delivery device configured to set a volume of the first portion of the inspiratory cycle in a respective breath [i] to be equal to or preferably less than the subject's baseline minute ventilation minus the subject's anatomic dead space ventilation;
  D. to control the amount of gas X in a volume of gas delivered to the subject in a first portion of the inspiratory cycle of a respective breath [i] and in a second remaining portion of that inspiratory cycle, to target the $PetX^T$ via breath [i], at least one of the breathing circuit and the control system configured to be able to provide to a subject, for inspiration:
    (a) a gas of a first composition determined by the processor for the first portion of the inspiratory cycle of a respective breath [i]; and
    (b) when the subject's ventilation in a respective breath [i] exceeds the gas of first composition available for a breath, a gas of second composition having a partial pressure of gas X (PX) selected from one of a PX approximating the PX in the subject's arterial blood after a previous breath, preferably a respective breath [i−1], and a $PetX^T$ targeted in the respective breath [i], the gas of second composition available for inspiration for the second remaining portion of the inspiratory cycle of a respective breath [i];
and wherein the control system implements a feedback algorithm which compares a $PetX^T$ for a respective breath [i] and optionally the value measured for the respective breath [i] from a previous breath.

According to another aspect, the invention is directed to a system for controlling an amount of at least one gas X in a mammal's lung, optionally a human subject, to target at least one end tidal partial pressure of at least one gas X ($PetX^T$), the system comprising:
(1) a measurement system preferably configured for measuring the concentration of the at least one gas X in a subject's end tidal expired gas;
(2) a control system for controlling a gas delivery device, optionally a gas blender, wherein the control system is configured to target and maintain a $PetX^T$ for a series of respective inspiratory cycles of variable length, the control system including a processor configured, for a respective breath [i]:
  A. to obtain input of at least one logistically attainable $PetX^T$ value;
  B. to obtain input from the measurement system of at least one measured value corresponding to the subject's current arterial blood concentration of gas X (e.g. $PaCO_2$), optionally the end tidal partial of gas X (PetX) attained as a result of gas exchange in the immediately preceding respective breath [i−1];
  C. to determine of an amount of gas X required to be inspired by the subject in at least a first portion of an inspiratory cycle of a respective breath [i] to target the $PetX^T$ for a respective interval;
  D. to set a volume of the first portion of the inspiratory cycle in a respective breath [i] to be less than the subject's baseline minute ventilation minus the subject's anatomic dead space ventilation;

E. to control the amount of gas X in a volume of gas delivered to the subject in a first portion of the inspiratory cycle of a respective breath [i] and in a second remaining portion of that inspiratory cycle, to target the $PetX^T$ via breath [i], at least one of the breathing circuit and the control system configured to be able to provide to a subject, for inspiration:
  (a) a gas of a first composition determined by the processor, during the first portion of the inspiratory cycle of a respective breath [i]; and
  (b) when the subject's ventilation in a respective breath [i] exceeds the gas of first composition available for a breath, a gas of second composition having a partial pressure of gas X (PX) selected from one of a PX approximating the PX in the subject's arterial blood after a previous breath, preferably a respective breath [i−1], and a $PetX^T$ targeted in the respective breath [i] (i.e. the gas of second composition is provided for inspiration for the second remaining portion of the inspiratory cycle of a respective breath [i]);

and wherein the control system implements a feedback algorithm which compares a $PetX^T$ for a respective breath [i] and preferably a respective current measured PetX value to obtain an error signal, the feedback algorithm adapted for generating a control signal based on the error signal, the control signal determining the amount of gas X to be inspired by the subject in at least a first portion of a respective ensuing respective inspiratory cycle to target $PetX^T$ for the respective interval.

The system optionally comprises a gas delivery device. Alternatively, the system is embodied in a separate computer, optionally a portable computer that is connected to a gas delivery device, optionally a gas blender.

In one embodiment, the control system is configured to target a $PetX^T$ for a plurality of respective intervals. Optionally, each respective interval is a single breath.

According to one aspect, the invention is directed to a system for controlling an amount of at least one gas X in a subject's lung to target at least one end tidal partial pressure of at least one gas X ($PetX^T$), the system comprising:
(1) a gas delivery device configured for connection to a breathing circuit, the breathing circuit of the type connectable a patient airway interface;
(2) a measurement system for measuring the concentration of the at least one gas X in a subject's end tidal expired gas;
(3) a control system for controlling the gas delivery device, wherein the control system is configured to target at least one $PetX^T$ for at least one in a series of respective intervals, the respective intervals at least defined by a series of respective inspiratory cycles of variable size, the control system including a processor configured to, for a respective breath [i]:
  A. obtain input of at least one logistically attainable $PetX^T$ value for the respective interval;
  B. obtain input from the measurement system of at least one measured PetX value attained as a result of gas exchange in a previous interval, preferably in an immediately preceding respective breath [i−1];
  C. determine of an amount of gas X required to be inspired by the subject in at least a first portion of an inspiratory cycle of a respective breath [i] to target the $PetX^T$ for a respective interval, the gas delivery device configurable to set a volume of the first portion of the inspiratory cycle in a respective breath [i] to be equal to or preferably less than the subject's baseline minute ventilation minus the subject's anatomic dead space ventilation;
  D. Control the amount of gas X in a volume of gas delivered to the subject in a first portion of the inspiratory cycle of a respective breath [i] and in a second remaining portion of that inspiratory cycle, to target the $PetX^T$ for the interval, the breathing circuit or the control system configured to make available to a subject, for inspiration:
    (a) a gas of a first composition determined by the processor for the first portion of the inspiratory cycle of a respective breath [i]; and
    (b) when the subject's ventilation in a respective breath [i] exceeds the gas of first composition available for a breath, a gas of second composition having a partial pressure of gas X (PX) selected from a PX approximating the PX in the subject's arterial blood after a previous breath, preferably a respective breath [i−1], or a $PetX^T$ targeted in the respective breath [i], the gas of second composition available for inspiration for the second remaining portion of the inspiratory cycle of a respective breath [i];

and wherein the control system implements a feedback algorithm which compares a $PetX^T$ for a respective breath [i] and preferably a respective current measured PetX value to obtain an error signal, the feedback algorithm adapted for generating a control signal based on the error signal, the control signal determining the amount of gas X to be inspired by the subject in at least a first portion of a respective ensuing respective inspiratory cycle to target $PetX^T$ for the respective interval.

In one embodiment, the control system is configured to target a $PetX^T$ for a plurality of respective intervals. Optionally, each respective interval is a single breath.

In the context of the using feedback to improve an predictive model, the term "target" means to set as a goal "approximating" a particular end tidal value of gas X that is preferably at least as accurate as that which could be obtained by prospective modelling alone as defined below under the heading "Prospective Model For End Tidal Targeting, Targeting Sequences and Various Applications of End Tidal Targeting Systems and Algorithms". Although a prospective model is not required for operation of the invention, the attainment of the target using feedback and a sequential gas delivery approach is optionally capable of producing the results obtained in Example 1 below, however it will be appreciated that the accuracy demands of the particular application may well provide for latitude in targeting accuracy.

Optionally, the amount of gas X required to be inspired by the subject in at least a first portion of a respective breath [i] to target the $PetX^T$ for a respective interval is determined prospectively based on a predictive or feed forward algorithm, and a feedback control signal is added to the control signal generated as a result of the prospective determination in any applicable manner known to those skilled in the art.

With respect to the description of the prospective algorithm described in Section C below, it will be appreciated that reference to "controlling" the amount in a volume of gas delivered to the subject in a respective breath [i] to target the respective $PetX[i]^T$ based on the prospective computation, represents a partial accomplishment of the objective of using feedback to adjust the output of the predictive model. Thus "controlling" as described in Section C is to be understood for purposes of the present invention as "controlling in part or in tandem with negative feedback". The predictive algorithm is optionally tuned as herein defined in Section C.

Optionally, the amount of gas X required to be inspired by the subject in at least a first portion of a respective breath [i] to target the $PetX^T$ for a respective interval is determined prospectively on a breath by breath basis based on a tidal model of the lung (as described herein in Section C).

Optionally, the feedback control signal is generated using a feedback control algorithm selected from a group comprising a PD, a PI and a PID control algorithm.

Optionally, the gas delivery device is a real-time gas blender.

Optionally, the breathing circuit includes a patient airway interface, a distally located one way inspiratory valve and a distally located one way expiratory valve. Optionally, the measurement system includes a gas X analyzer positioned to measure the gas X concentration exiting the one expiratory valve.

Each of the individual features described herein and each member feature of groups of features described collectively for convenience below or above, whether described individually or as members features of a group of features, is to be considered as described individually with respect to each of the broadest and narrower aspects of the invention described in this summary of invention.

BRIEF DESCRIPTION OF THE DRAWINGS

Particular embodiments of the invention will now be described with reference to the drawings, of which:

FIG. 7 presents tabulated results of Example 1 using one embodiment of a system according to the invention, the system used for implementing a targeting sequence to control a subject's end tidal concentration of $CO_2$ according to the invention.

FIG. 8g reproduces a targeting sequence including a time line of the target end tidal $PCO_2$ values sought to be approximated using the invention.

FIG. 10 is a schematic representation of a lung illustrating how sequentially delivered components of a respiratory gas may contribute differentially to gas exchange with the pulmonary circulation.

FIG. 11 is a schematic representation of one example of a reference breathing circuit.

FIG. 12 is a schematic representation of another example of a reference breathing circuit.

FIG. 13 is a schematic representation of one embodiment of a respiratory gas delivery system according to the invention.

FIG. 14 is a schematic representation of another embodiment of a respiratory gas delivery system according to the invention.

FIGS. 15-25 relate to features of the invention described above that are particularly related to a prospective model of end tidal targeting of one or more gases, and in particular, a tidal model for this purpose. Immediately below, in the figure descriptions, and in the related description under the heading "Prospective Model For End Tidal Targeting, Targeting Sequences and Various Applications of End Tidal Targeting Algorithms". Reference to the invention is to the inventions as defined in the summary of invention organized under this heading and reference numerals appearing in FIGS. 15-24 are tied only to the description under this heading and to the invention defined in claims paragraphs 1B to 79B and 1C to 89C which define an embodiment of a prospective model that may be used in connection with the subject matter of the instant invention.

FIG. 15 is a schematic overview of the movement of blood and the exchange of gases throughout the entire system.

FIG. 16 is a detailed schematic representation of the movement of blood and the exchange of gases at the tissues.

FIG. 17 is a detailed schematic representation of the movement of blood and the exchange of gases at the lungs when sequential rebreathing is not employed.

FIG. 18 is a detailed schematic representation of the movement of blood and the exchange of gases at the lungs when sequential rebreathing is employed.

FIG. 19 is a schematic diagram of one embodiment of an apparatus according to the invention that can be used to implement an embodiment of a method according to the invention.

FIG. 20 is a graphic representation of a tuning sequence and observed errors that can be used to tune model parameters.

FIG. 21 is a Table of abbreviations (Table 1) used in the description under the heading: "Prospective Model For End Tidal Targeting, Targeting Sequences and Various Applications of End Tidal Targeting Algorithms"

FIG. 23 is a graphical representation of blood flow responses to $PCO_2$ predicted for the model of a brain vascular territory with a partially-stenosed vessel branch and a healthy branch in parallel as revealed by a ramp sequence.

FIG. 24 is a graphical representation of a bold signal response to $PCO_2$ as revealed by a ramp sequence and corresponding CVR maps for an axial slice at different $PetCO_2$ ranges for a patient with moya moya disease.

FIG. 25 discloses end tidal targets and results of targeting obtained using the prospective model and represents a partial raw data set—for 6 of the subjects.

SECTION A: DETAILED DESCRIPTION OF PREFERRED EMBODIMENTS OF PRESENT INVENTION

Figure 1:
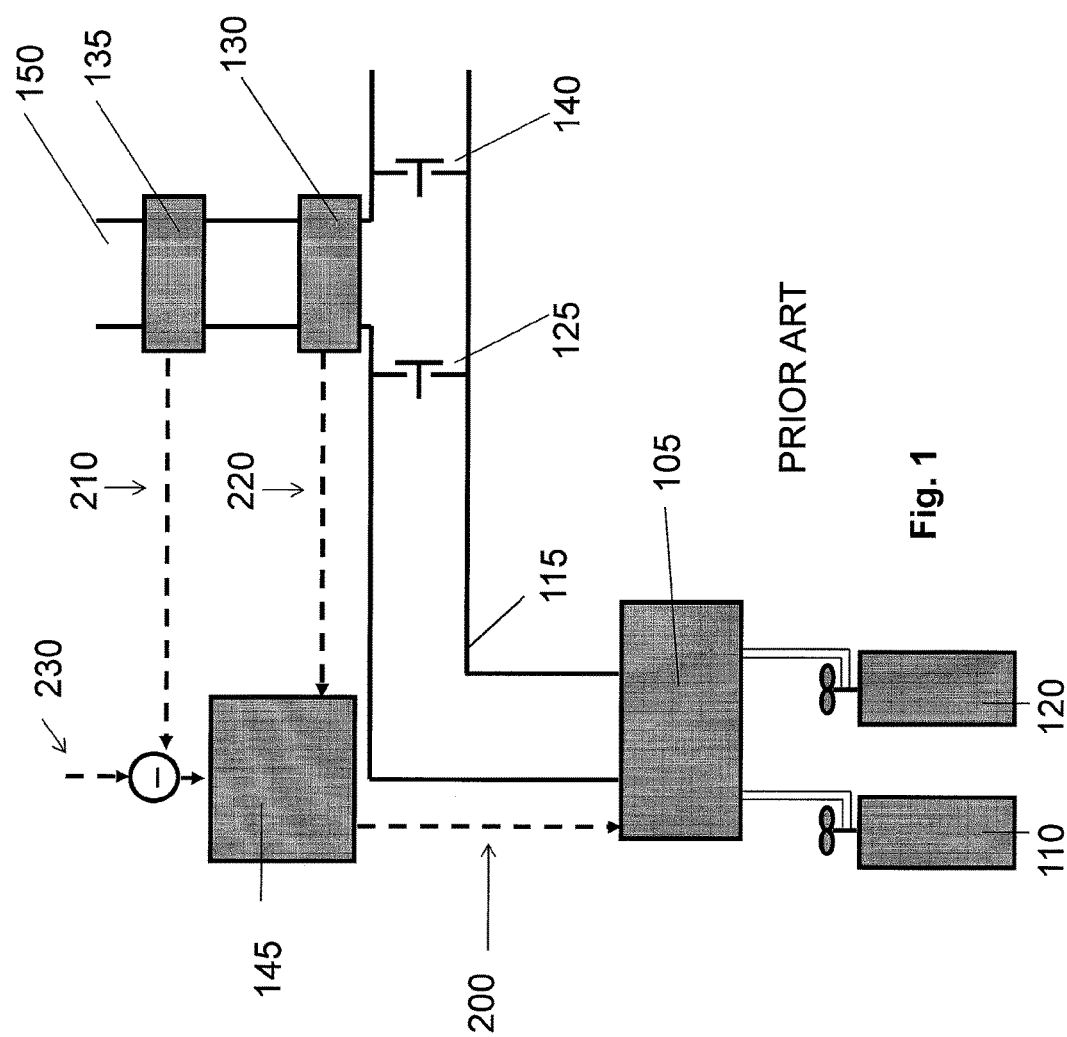
FIG. 1 is a diagrammatic representation of one prior art dynamic end tidal forcing system.

The expressions "for attaining" or "to attain" are used to express the goal of a targeting algorithm and are used synonymously with the term "targeting". Use herein of this phraseology with reference to $PetX[i]^T$ should be understood to be most meaningful in a particular context for which the invention is used, for example having regard to the precision of the technology used for measuring the results and delivering the gas. Additionally, for gases such as oxygen and carbon dioxide relevant context includes the extent to which a particular $PetX[i]^T$ departs from normal partial pressures of these gases since homeostatic mechanisms are in play to temper change. For the sake of example only, assuming a measurement error of +/−2 mm. of Hg, in the case of $CO_2$, for a $PetX[i]^T$ between 30 and 50 mmHg, a measured $PetCO_2$ value that is within 1 to 3 mm. of Hg of $PetX[i]^T$ can be considered to be a goal ("targeted") and also actually achieved with relative precision.

For present purposes, a mass balance equation is understood to be a mathematical relationship that applies the law of conservation of mass (i.e. the amount of at least one gas X) to the analysis of movement of at least one gas X, in and out of the lung, for the purpose of prospectively targeting an end tidal partial pressure of gas X. Optionally, where an end tidal partial pressure of gas X is sought to be changed from a baseline steady state value or controlled for a sequence of respective breaths [i] the mass balance equation will account for the transfer of a mass of gas X between a subject's lung and pulmonary circulation (i.e. the mixed venous blood entering the pulmonary capillaries ($C_{MV}X[i]$)); so that this key source of flux affecting the end tidal partial pressure of gas X in the breath(s) of interest, is accounted for.

The term "high resolution" when used with reference to imaging modality or device refers to an imaging modality enjoying a spatial resolution of 1 cubic centimeter or smaller. The term includes MRI imaging modalities (for example BOLD, T2*, ASL) and other imaging modalities well known as being useful to quantify surrogate measures of blood flow (CT, SPECT, PET).

A "gas blender" means a device that combines one or more stored (optionally stored under pressure or delivered by a pump) gases in a pre-defined or selectable proportion for delivery a selectable rate of flow, preferably under computer control. For example one or more stored gases may be combined with pumped room air or a combination of pure or blended (each blended gas may have at least 10% oxygen for safety) gases respectively contain one of carbon dioxide, oxygen and nitrogen as the sole or predominant component. Optionally, the selectable proportion is controlled automatically using an input device, optionally by variably controlling the flow of each stored gas (pure or pre-blended) separately, preferably using rapid flow controllers, to enable various concentrations or partial pressures of a gas X to be selected at will within a pre-defined narrow or broad range. For example, the gas blender may be a high flow blender which blows gas past the mouth (i.e. in which gas that is not inspired is vented to the room) or the gas blender may be adapted to conserve gas by delivering gas in volumes that closely match the patient's volume requirements of a breath.

Optionally, the respiratory gas delivery apparatus contains the basic structural or specialized algorithmic features described in WO/2012/139204.

The term "real time gas blender" means, with reference to instant invention, a gas blending apparatus that introduces a variable amount of at least one gas X (e.g. carbon dioxide, oxygen, nitric oxide or other medically active gases) into a principal inspiratory gas stream (e.g. consisting of air or oxygen enriched air) to make available to a subject, for inspiration, a combined gas stream having a selected concentration of gas X. Control of gas X flow into the principal gas stream is, in principle, based on continuously determining the rate of flow of the principal inspiratory gas flow and adding amounts of gas X accordingly. Such a blender may employ a flow based algorithm, for example as described in U.S. Pat. No. 5,558,083, or may more advantageously employ a volume-based control system as described in our co-pending published PCT application WO/2012/139204.

The term "computer" is used broadly to refer to any device (constituted by one or any suitable combination of components) which may be used in conjunction with discrete electronic components and/or parts e.g. valves to perform the functions contemplated herein, including computing and obtaining input signals and providing output signals, and optionally storing data for computation, for example inputs/outputs to and from electronic components and application specific device components as contemplated herein. As contemplated herein a signal processor or processing device in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a pressure transducer, a gas analyzer, any type of input device for inputting parameters or values (for example, a knob, dial, keyboard, keypad, mouse, touch screen etc.), input from a computer readable memory etc. Key outputs may include output to a flow controller (e.g. PI control or PID control etc.). The term "processor" and "computer" are used interchangeably.

The term "dynamic end tidal forcing" refers to a negative feedback control system that continuously measures an end tidal value of a gas of interest and compares that value to one or more target values to control the composition of a gas delivered to a subject in an attempt to match one or more target end tidal values.

The term "high flow" used to describe a gas blender means that the gas blender is able to blend component gases of an inspiratory gas to a required concentration of at least one gas X for inspiration in amounts sufficient to continuously supply a volume of gas that supports the full inspiratory volume requirements of a subject under various physiological conditions which means that the output of the gas blender might need to be high well above a subject's minute ventilation. For example, in one exemplary study (Wise R G, et al. Dynamic forcing of end-tidal carbon dioxide and oxygen applied to functional magnetic resonance imaging. J Cereb Blood Flow Metab. 2007 August; 27 (8): 1521-32) the total gas delivery rate to the breathing system was maintained at 70 liters per minute (LPM) to avoid rebreathing of expired gases and to minimize the delay in supplying updated gas mixtures to the subject.

Various applications of the invention defined in the Summary of Invention above are presented throughout the disclosure herein and some are listed in the pubmed cross-referenced references 1 to 16 at the conclusion of the disclosure.

The demands of a diagnostic application may be ascertained empirically or from the literature. For example, a measure of short response times of brain blood vessels to hypercapnic stimulus can be determined to require a square wave change in the stimulus such as a change of 10 mmHg $P_{ET}CO_2$ from one breath to the next. Another example is when measuring response of BOLD signal with MRI to changes in partial pressure of $CO_2$ in the blood, the changes needed may be determined to be abrupt as the BOLD signal has considerable random drift over time.

For measuring heart vascular reactivity, the inventors have demonstrated that attaining target end tidal concentrations to within 1 to 3 mm of Hg of the targets, preferably to within 1 to 2 mm of Hg of the targets, using an apparatus, computer program product, or IC chip and method according to the invention enables the invention to be used for cardiac stress testing (see WO2012/1151583). Therefore, according to one aspect, the invention is directed to the use of apparatus, computer program product, IC chip and/or method according to the invention for cardiac stress testing.

The invention is also adapted for use as a controlled stimulus, for example to calibrate a BOLD signal (Mark C I et al. Improved fMRI calibration: Precisely controlled hyperoxic versus hypercapnic stimuli (2011) NeuroImage 54 1102-1111); Driver ID. et al. Calibrated BOLD using direct measurement of changes in venous oxygenation (2012) NeuroImage 63(3) 2278-87) or as an adjunct or preliminary step in diagnosing abnormal cerebrovascular reactivity. For example, determining the presence of abnormally reduced vascular reactivity using an apparatus, computer program product, IC chip and/or method according to the invention is useful for predicting susceptibility to stroke (Silvestrini, M. et al. Impaired Cerebrovascular Reactivity and Risk of Stroke in Patients With Asymptomatic Carotid Artery Stenosis JAMA (2000) 283(16) 2179; Han J. S. et al. Impact of Extracranial Intracranial Bypass on Cerebrovascular Reactivity and Clinical Outcome in Patients With Symptomatic Moyamoya Vasculopathy, Stroke (2011) 42:3047-3054) or dementia (Balucani, C. et al. Cerebral Hemodynamics and Cognitive Performance in Bilateral Asymptomatic Carotid Stenosis Neurology (2012) October 23; 79(17) 1788-95) and diagnosing or assessing cerebrovascular disease (Mutch W A C et al. Approaches to Brain Stress Testing: BOLD Magnetic Resonance Imaging with Computer-Controlled Delivery of Carbon Dioxide (2012) PLoS ONE 7(11) e47443).

The invention is similarly adapted for diagnosing or assessing idiopathic intracranial hypertension (IIH) or idiopathic normal pressure hydrocephalus (Chang, Chia-Cheng et al. A prospective study of cerebral blood flow and cerebrovascular reactivity to acetazolamide inpatients with idiopathic normal-pressure hydrocephalus (2009) J Neurosurg 111:610-617), traumatic brain injury (Dicheskul M L and Kulikov V P Arterial and Venous Brain Reactivity in the Acute Period of Cerebral Concussion 2011 Neuroscience and Behavioural Physiology 41(1) 64), liver fibrosis or liver disease in which liver fibrosis is a feature (Jin, N. et al. Carbogen Gas-Challenge BOLD MR Imaging in a Rat Model of Diethylnitrosamine-induced Liver Fibrosis January 2010 Radiology 254(1) 129-137) and conditions manifesting abnormal kidney vascular reactivity, for example renal denervation in transplant subjects (Sharkey et. al., Acute effects of hypoxaemia, hyperoxaemia and hypercapnia on renal blood flow in normal and renal transplant subjects, Eur Respir J 1998; 12: 653-657.

As seen in FIG. 1, a prior art dynamic end tidal forcing system employs a high flow blender 105 to blend gases stored under pressure in tanks 110 and 120 e.g. an air tank 110 and a gas X tank 120 e.g. a $CO_2$ tank. A breathing circuit comprising a conduit 115 leads from the high flow blender 105 to a patient 150 outfitted with an airway interface such as a mask (not shown). Conduit 115 is connected to the patient airway interface through a one way inspiratory valve 125, a flow meter 130 and a gas analyzer 135 e.g. a $CO_2$ sensor. A subject exhales through the gas analyzer and through one way expiratory valve 140. Input of one or more target end tidal values of gas X 230 is received by a feedback controller 145 which also receives input from flow meter 130. The feedback controller 145, which may be embodied in a microprocessor or an external processor (e.g. a PC) receives output 210 from the gas X analyzer 135 and the difference between the gas analyzer output 210 and the current target end tidal value is used to provide an output signal 200 to a rapid flow controller in a high flow gas blender 105 to output an inspired concentration of gas X ($F_IX$) required to attain the target end tidal concentration of gas X based on the feedback algorithm. The sole source of inspiratory gas is the output from the gas blender 105, so that total output from the gas blender 105 must at all times be greater than the subject's peak inspiratory flow rate. Gas not inspired is exhausted through the expiratory valve 140.

Figure 2:
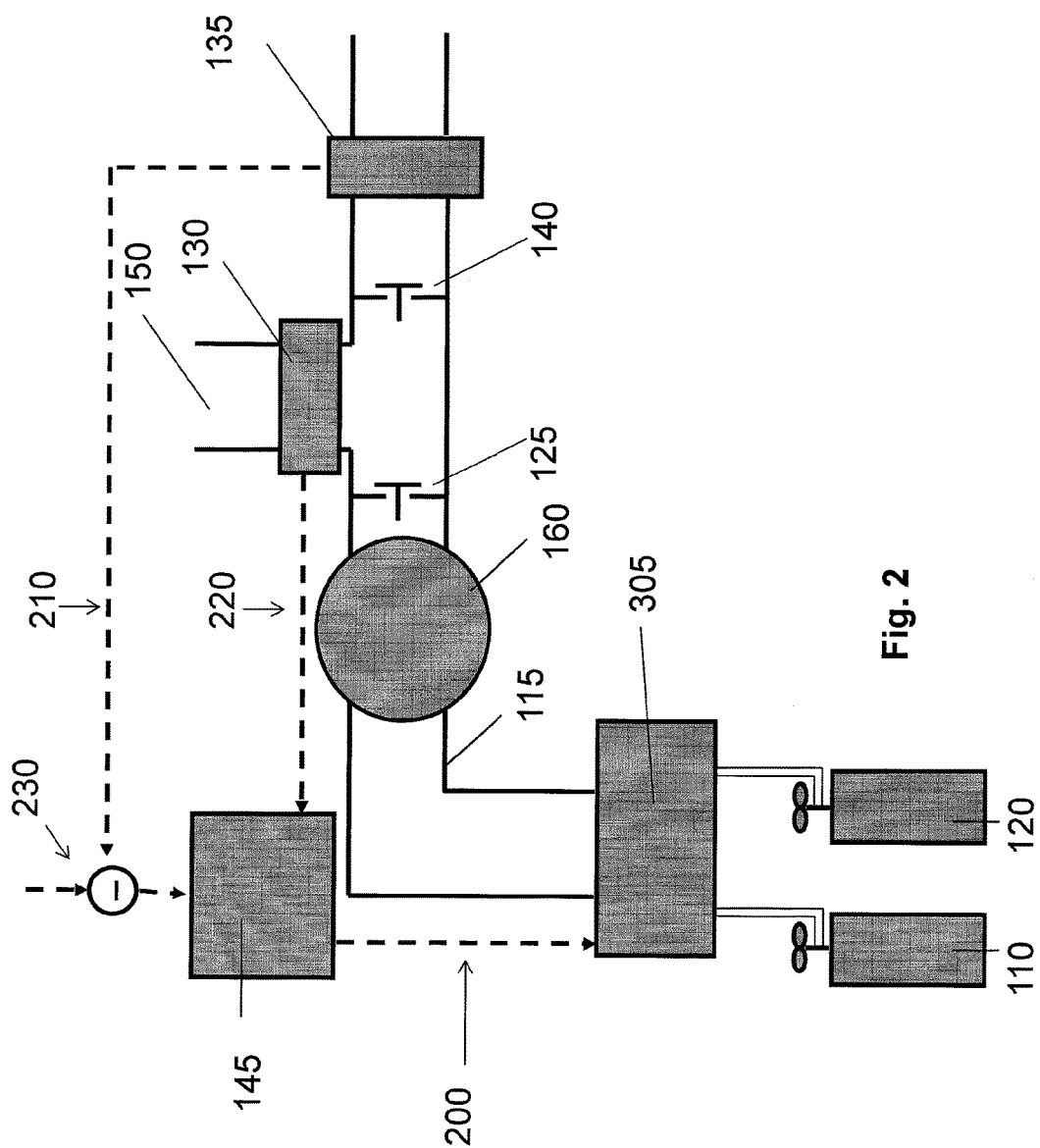
FIG. 2 is a diagrammatic representation of a modified, prior art dynamic end tidal forcing system in which an inspiratory reservoir receives inspiratory gas intended for inspiration by a subject.

FIG. 2 shows a variation of the system depicted in FIG. 1 in which a gas blender 305 is connected to an inspiratory reservoir 160 (see Koehle M S. et al. Performance of a compact end-tidal forcing system, Respir. Physiol. Neurobiol. 2009 Jun. 30; 167(2): 155-61). Accumulation of gas in the reservoir during expiration lessens the rate of flow needed to meet a subject's inspiratory requirements. This system wastes less gas than the blow-by-the-mouth method described with reference to FIG. 1 (Wise et al. 2007).

For use of a physical sequential gas delivery circuit, the flow of gas of first composition is selected so that the subject empties the gas reservoir (e.g. bag) the gas of first composition. A breath in which this per chance does not occur is ignored.

However, it will also be appreciated that a particular gas composition formulated for delivery in respective breath, as determined by a dynamic feedback system, will in each breath be mixed with uncertain amount of gas remaining in the inspiratory reservoir and tubing from a previous breath, which introduces a source of instability into the system.

Figure 3:
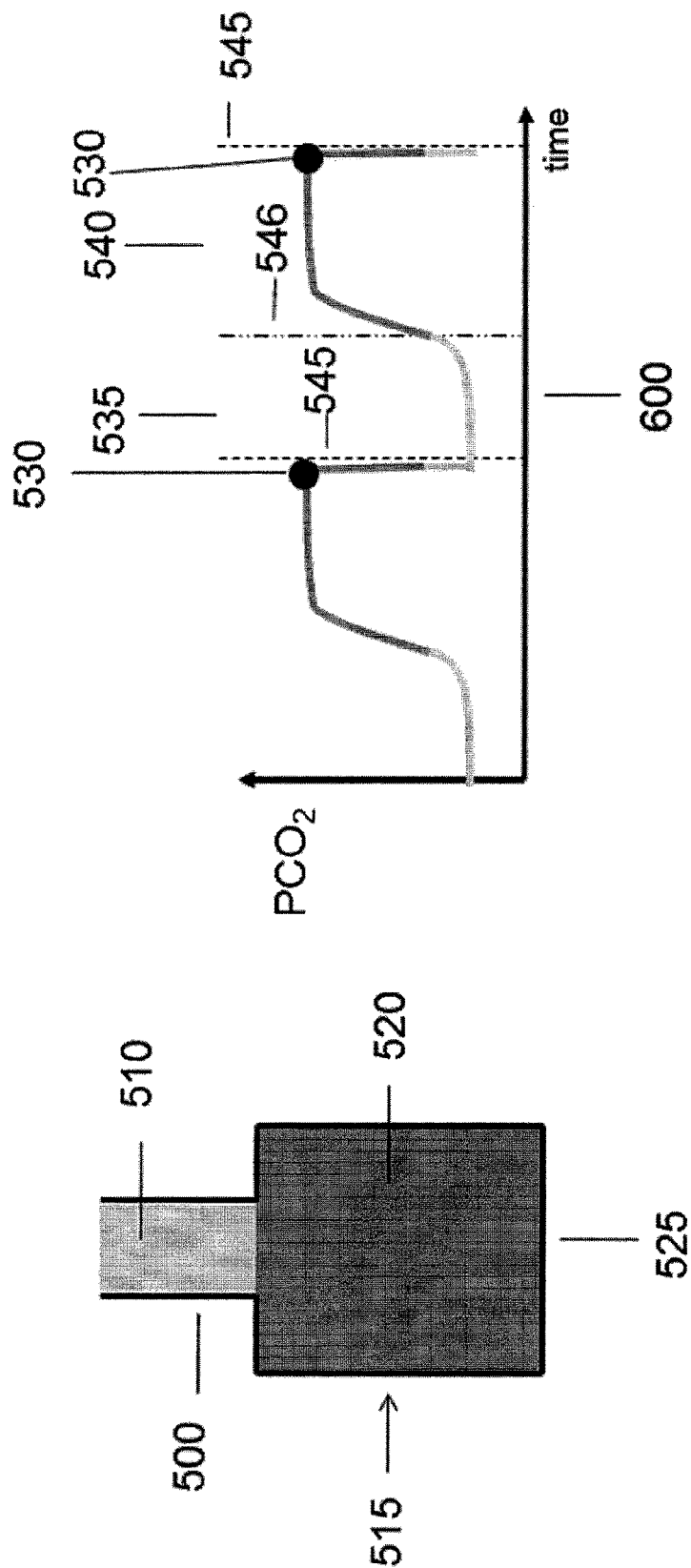
FIG. 3a is a diagrammatic representation of components a subject's expired gas that would affect the results of a capnograph that would be obtained using a prior art dynamic end tidal forcing system.
FIG. 3b is a diagrammatic representation of results that would be obtained from a capnograph when using a prior art or modified prior art dynamic end tidal forcing system. These results correspond to measured PetX values sampled from a location proximal to the patient airway interface (see positioning of gas analyzer in FIGS. 1 and 2).

Notably, in the modified system depicted in FIG. 2, the gas analyzer 135 could perhaps be placed in the expiratory limb provided that the inspiratory reservoir never overflows. The gas analyzer does not see inspiratory concentrations of gas X within a common line leading to the patient airway interface as described with reference to FIG. 1. However, as described in more detail with reference to FIG. 3, relative to the system and apparatus of the invention, greater inaccuracies may be introduced into the system as a result of errors in end tidal picking.

As seen in FIG. 3b, depicting a theoretical capnograph tracing corresponding to two consecutive inspiratory cycles demarcated by dashed lines 545, expiratory gas initially exhaled by the patient consists of the lighter shaded area gas 510 remaining in the dead space 500 after an inspiratory cycle, as seen in model of the lung 515 in FIG. 3a. This gas has essentially the concentration of gas X (e.g. $CO_2$) last inspired by the subject in the immediately preceding inspiratory cycle. This gas remains in and is first expired from the dead space 500. The last expired or end tidal gas 520 has the concentration of gas X in the alveoli 525 following gas exchange in a particular respective inspiratory cycle. Dashed line 546 demarcates the transition between expiration of the dead space gas 510 (lighter shade of gray) and the alveolar gas 520 (darker shade or gray) evidencing the beginning of a rise in the subject's $PCO_2$. It will be appreciated that end tidal picking errors may reflect $PCO_2$ values of the dead space gas 510.

The system of the present invention will now be described by way of contrast.

An embodiment of a system, method and apparatus for implementing the invention is shown schematically in consecutive embodiments described with reference to FIGS. 4, 5 and 9.

Figure 4:
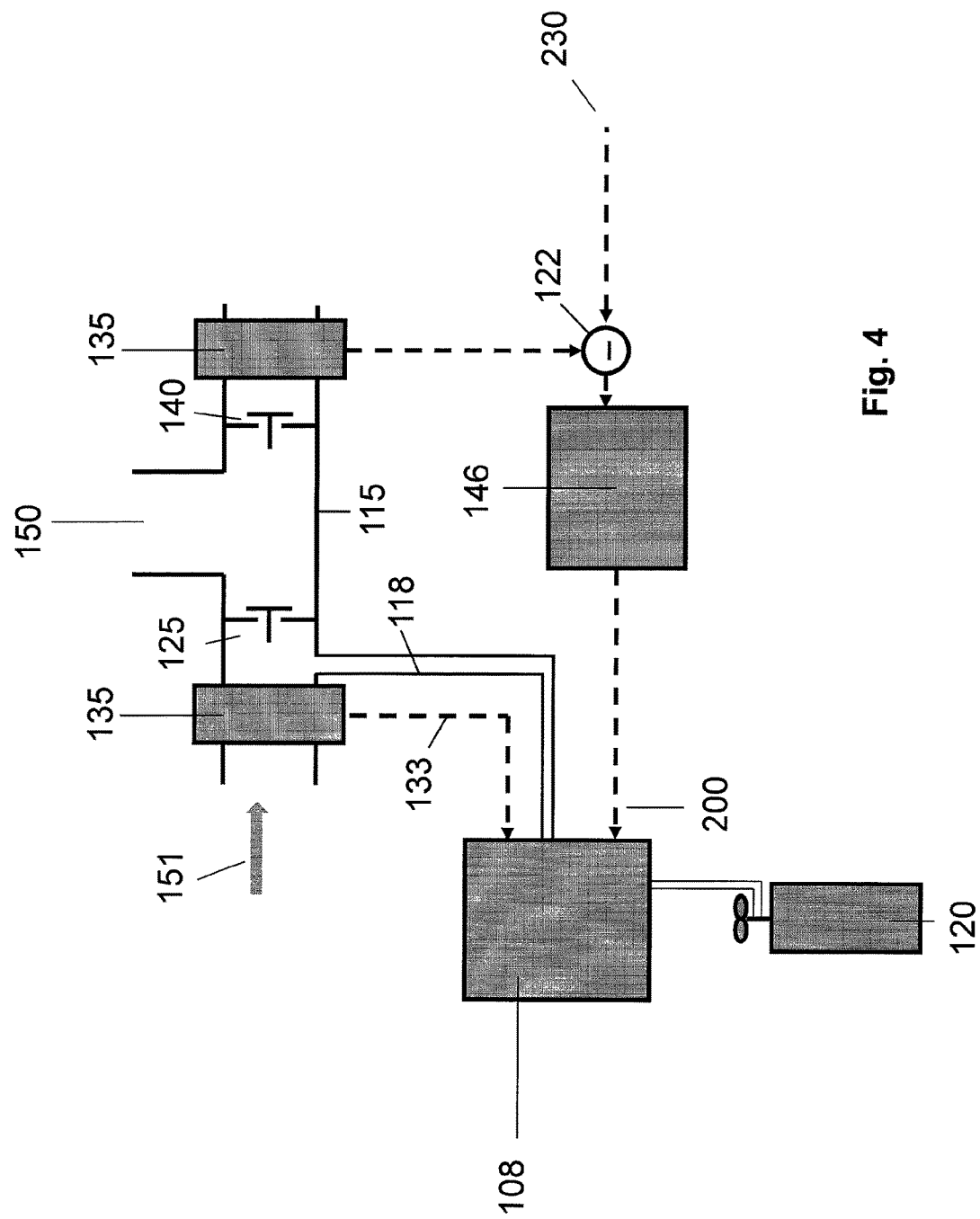
FIG. 4 is a schematic diagram showing one embodiment of a system for implementing a targeting sequence to control a subject's end tidal concentration of a gas X according to the invention.

As seen in FIG. 4, a control system including a feedback controller 146, optionally implemented by a processor, for example a microcontroller, obtains input 230 comprising at least one of a series of $PetX[i]^T$ values, the series comprising at least one such value per breath or time period, or per series of breaths or time periods, namely one or more breath or time interval associated $PetX[i]^T$ values e.g. relative increments and/or $PetX[i]^T$ decrements, which may be stored, or input 230 via using any suitable input device. Optionally, at least one target for a first series of breaths will be obtained, for example, where gas X is $CO_2$, $PCO_2$ values for each of a first series of breaths (e.g. 40 mm Hg) and then optionally at least one $PCO_2$ target for an ensuing series of breaths e.g. 50 mm of Hg, optionally followed by at least one $PCO_2$ target for a series of final breaths in the collective series (e.g. 50). Optionally, the series may define a ramp sequence as described herein.

A feedback controller 146 may use any suitable control algorithm known to control-system programmers and may optionally be selected from a group comprising a PD, a PI and a PID control algorithm. The feedback algorithm compares 122 input end tidal target values 230 with output from the gas analyzer 135 (which is processed through an end tidal gas concentration picking algorithm to pick end tidal concentration values—not shown in order to simplify the illustration), for example on a breath by breath basis, and the feedback controller then sends control signals 200 to the gas blender, for example a real-time gas blender 108 to implement the feedback control system. The real time gas blender obtains a measure of flow 133 of a primary inspiratory gas 151 (e.g. air) via flow sensor 130 and adds a variable amount of gas X from tank 120 to this gas stream via conduit 118 to compose a gas of a composition which the feedback control algorithm has determined effective to attain the end tidal partial pressure of gas X input for the breath/interval. An exemplary volumetric real time gas blender is described in our published PCT application WO 2012/139204. A different flow-based real time blending algorithm is described in U.S. Pat. No. 5,558,083.

The control system also implements sequential gas delivery (SGD) either in conjunction with using a physical circuit SGD circuit, as described with reference to FIG. 9, or using a virtual sequential gas delivery algorithm which does not require a physical SGD circuit, as described herein.

For example, input of flow sensor readings 133 and feedback controller signals 200 to the real time gas blender 108 may be used to add CO2 to inspiratory gas stream 151 via conduit 118 from gas stored under pressure in $CO_2$ tank 120.

Figure 5:
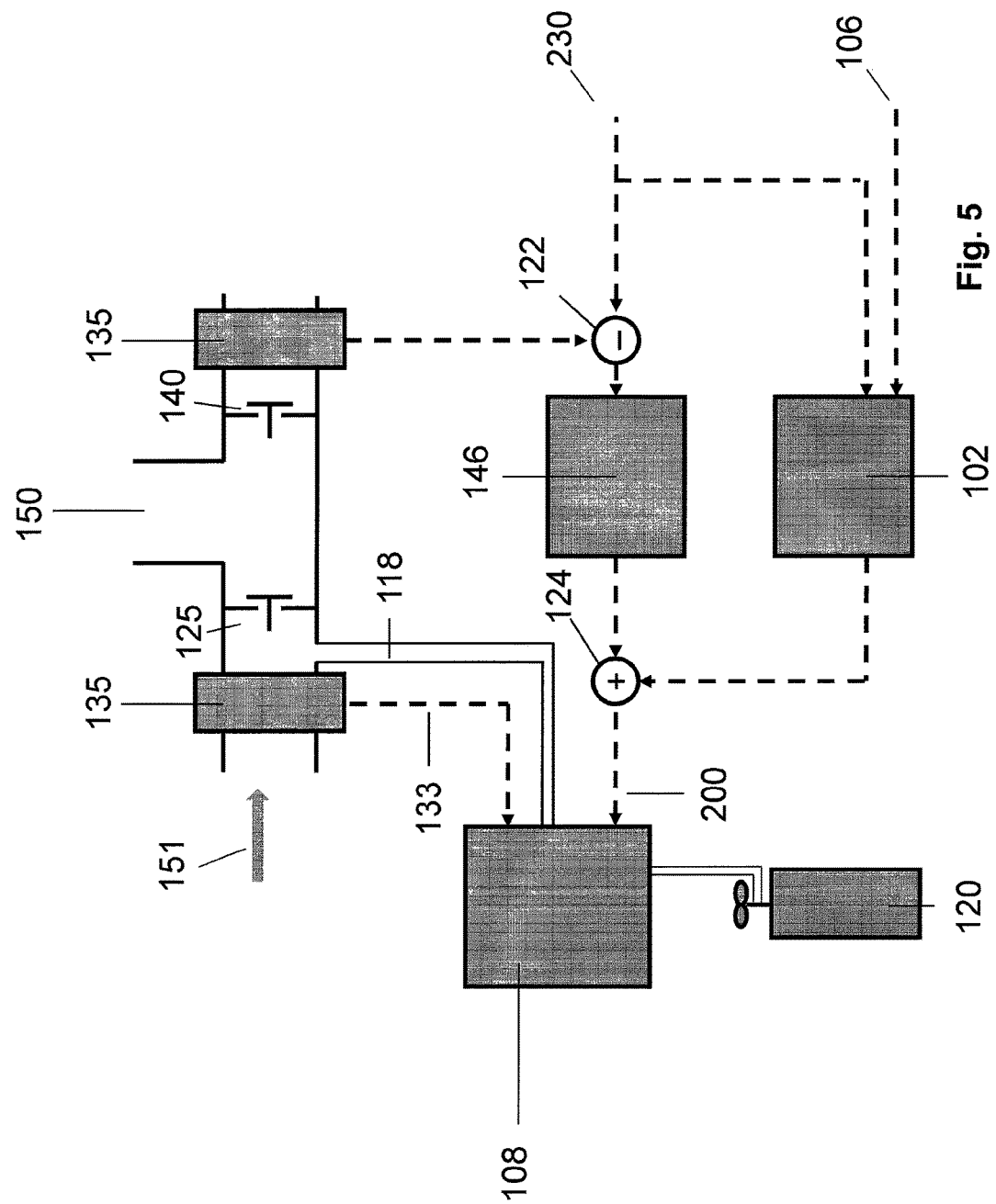
FIG. 5 is a schematic diagram showing another embodiment of a system for implementing a targeting sequence to control a subject's end tidal concentration of a gas X according to the invention.

Optionally, as seen in FIG. 5, the control system may also use a prospective model or predictive algorithm 102. For example, signals generated by the feedback controller 146 and as output of the prospective model 102 are added 124, such that the output of the prospective model (e.g. a computationally derived amount of at least one gas X required to be inspired by the subject in an inspired gas to target at least one $PetX[i]^T$ value for a respective interval) is adjusted, for example, on a breath by breath basis, by the feedback controller 146. One predictive model is based on a tidal model of the lung described in detail herein. Another (flow based) is described in Robbins P A, et al., A prediction-correction scheme for forcing alveolar gases along certain time courses. J. Appl. Physiol. 1982 May; 52(5):1353-7, for example using mass balance equations described in this 1982 paper.

The feedback controller 146, is depicted in FIG. 5 as determining the difference 122 (the error) between actual end tidal values of gas X obtained from the gas analyzer 135 (direct output of the gas analyzer is processed through an end tidal gas concentration picking algorithm to pick end tidal concentration values—not shown for simplicity) and the respective $PetX[i]^T$ input target values input 230. Patient data 106 informs the prospective model 102 (see Section C below) to enable a processor to output a computationally derived (predicted) $F_IX$ value required to target a particular $PetX[i]^T$ value as described in detail herein.

Figure 9:
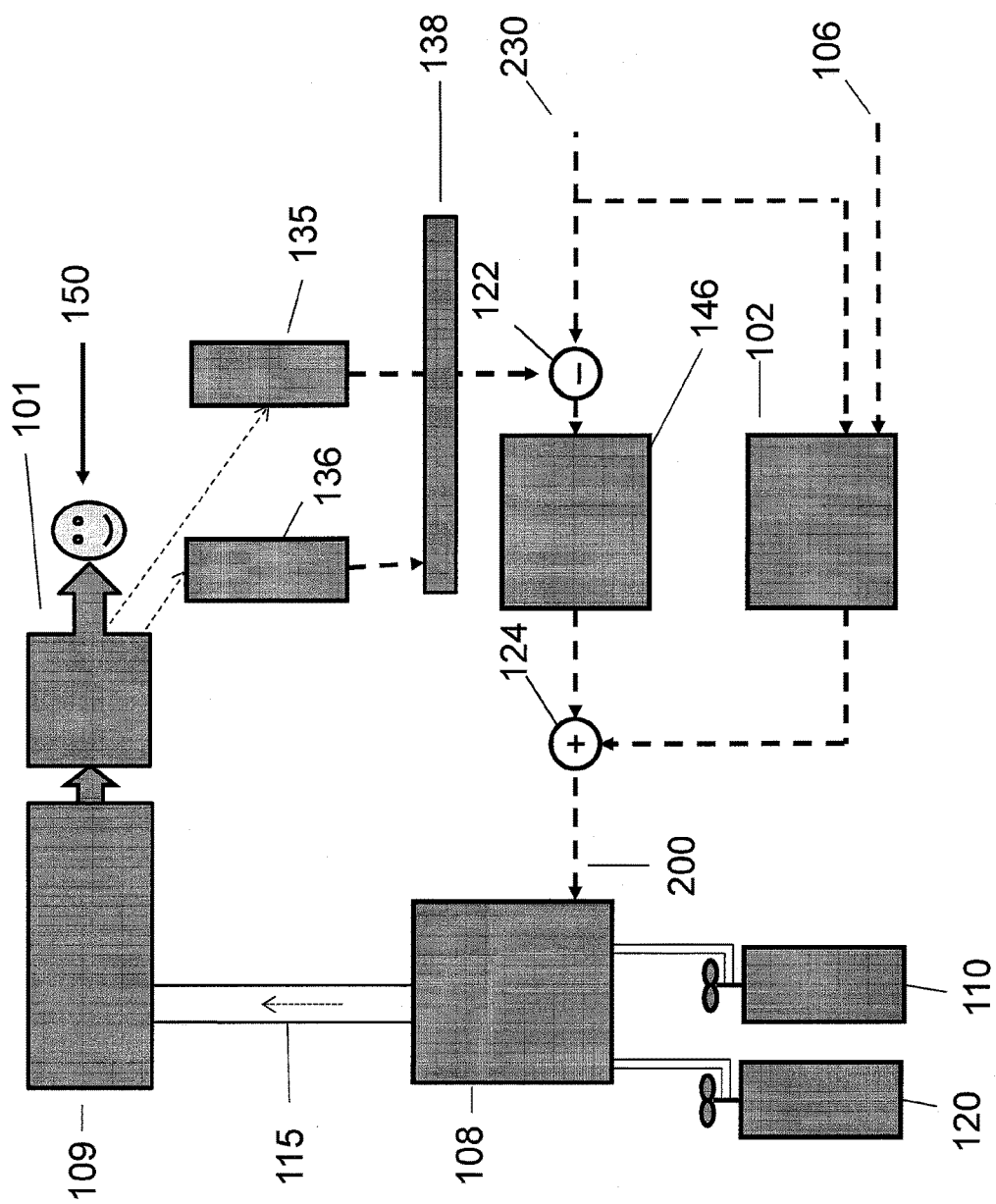
FIG. 9 is a schematic diagram showing yet another embodiment of a system for implementing a targeting sequence to control a subject's end tidal concentration of a gas X according to the invention. This system illustrates the use of a physical sequential gas delivery circuit and may be implemented with or without a prospective targeting algorithm in aid.

As seen in FIG. 9, a breathing circuit may comprise a conduit 115 which delivers gas to an inspiratory reservoir 109 and sequential gas delivery circuit 101 which is operatively associated (this association, generally described below, depicted for ease of illustration with solid arrows 104) with a gas analyzer 135 for detecting gas X concentration in a subject's exhaled gas and a pressure transducer 136 which may be used to assist end tidal picking using an end tidal picking algorithm 138. Gas conduit 115 leads from a real time gas blender 108 towards a spontaneously breathing subject 150 donning a patient airway interface such as a mask (not shown). Located along the circuit between inspiratory reservoir 109 and the patient airway interface, preferably proximal to the patient airway interface, is a one way inspiratory valve (not shown), and a gas analyzer 135 (e.g. a $CO_2$ or $O_2$ sensor) which provides output of at least gas X concentrations of gas exhaled by a subject. The circuit is optionally configured so that the subject exhales through the one way expiratory valve (not shown) and then past the gas analyzer 135. Optionally, the sequential gas delivery circuit is operatively connected to a pressure transducer 136, the output of which assists in end tidal picking via an end tidal picking algorithm 138. Input 230 of one or more target end tidal values of gas X is received by a feedback controller 146. The feedback controller 146, which may be embodied in a microprocessor or an external processor (e.g. a PC) receives output 210 from the gas X analyzer 135 (that has been processed through the end tidal picking algorithm 138) and the difference between the gas analyzer output 210 and the current target end tidal value is optionally 'added' to a signal derived from a predictive algorithm 102 (informed by subject parameters 106) which outputs a prospective determination of a predicted inspired concentration of gas X. This in turn is used to provide an output signal 200 to a rapid flow controller in gas blender 108 so as to output an inspired concentration of gas X ($F_I X$) required to attain the target end tidal concentration of gas X based on the feedback algorithm. The physical SGD circuit 101 may comprise one way inspiratory and expiratory valves (not shown) and a third valve (not shown) that enables a subject to draw on a source of gas, optionally a reservoir containing primarily expired end tidal gas expired in an immediately preceding breath or a gas of equivalent composition supplied to the patient upon depletion of the inspiratory reservoir 109 in any respective breath. SGD breathing circuits are exemplified in FIGS. 11 and 12 and in pending published US application 2007/006534 (also published under No. WO/2004/073779). In the context of the instant invention, when implemented with a specially adapted SGD circuit, the control system is used to control the rate of flow and configured to make available to a subject, for inspiration:

(a) a first inspired gas of a first composition determined by the processor for the first portion of the inspiratory cycle of a respective breath [i]; and (b) when the subject's ventilation in a respective breath [i] exceeds the first inspired gas of first composition available for a breath, a second inspired gas of second composition having a partial pressure of gas X (PX) selected from a PX approximating the PX in the subject's arterial blood after a previous breath, preferably a respective breath [i–1], or a $PetX^T$ targeted in the respective breath [i], the gas of second composition available for inspiration for the second remaining portion of the inspiratory cycle of a respective breath [i].

Some embodiments of the physical SGD circuits exemplified in WO/2004/073779 employ a set of three passive valves including one way inspiratory and expiratory valves and a valve associated with a by-pass conduit. Alternatively active valves may be employed.

In summary, a physical sequential gas delivery circuit is commonly a breathing circuit for use with a first gas (FG) and a second gas (SG), the circuit optionally comprising an inspiratory limb, an expiratory limb, an FG reservoir and a flow control system for sequentially delivering to a patient on inspiration, in a given breath [i], first the FG, preferably substantially free of SG, and, when the FG reservoir is emptied, SG, preferably substantially free of FG, for a balance of inspiration, wherein the inspiratory limb is operatively connected to the FG reservoir, and wherein the flow control system includes at least one first valve operatively associated with the expiratory limb for preventing inhalation of SG during delivery of the FG and at least one second valve operatively associated with the inspiratory limb to prevent inhalation of FG during delivery of the SG. The first and second valves may be passive (open responsive to pressure in the circuit) and may operate in tandem using interconnected valve closure members such that when one is open the other is closed and vice versa. In some embodiments, such a circuit may employ two active valves, one on the inspiratory side and one on the expiratory side. Alternatively, the circuit may employ an active valve or passive valve on the inspiratory side and two passive valves on the expiratory including a one way expiratory valve and another valve associated with a by-pass limb through which SG can be drawn to by-pass the one way expiratory valve.

A virtual SGD circuit may use one way inspiratory and expiratory valves as exemplified in FIGS. 4 and 5, but it should be noted that the inspiratory valve 125 (FIG. 4, FIG. 5) and expiratory valve 140 (FIG. 4, FIG. 5) are not required to modulate the inspiratory gas. As an alternative shown in FIG. 6c, the patient may inspire a primary inspiratory gas 151 through a flow sensor 135 and gas analyzer 145 arranged in a single conduit 100, where the flow sensor 135 is part of a real-time gas blender (not shown) which is configured to add a gas X to a primary inspiratory gas 151 via a second conduit (not shown, 118 FIG. 4 and FIG. 5) connected to a port 110 to attain a desired amount of X in the inspiratory stream.

In one embodiment X is $CO_2$.

In another embodiment, the control system independently controls $PetX[i]^T$ for two or three gases e.g. $CO_2$ and $O_2$.

Figure 6B:
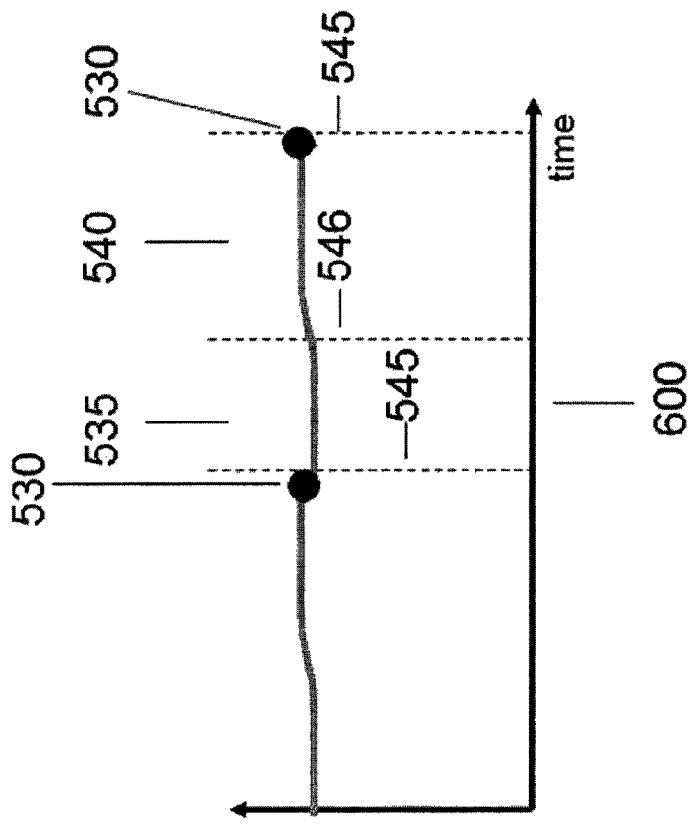
FIG. 6b is a graph of end tidal readings derived from the output of a capnograph that would be obtained using a system according to the invention referred to in FIG. 4 or 5. These results correspond to measured PetX values sampled from the expiratory limb after exhaled gas passes through a one way expiratory valve.
Figure 6A:
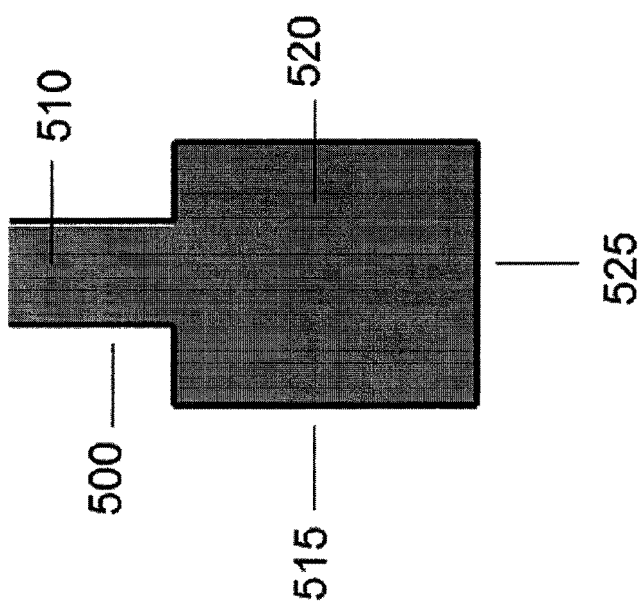
FIG. 6a is a diagrammatic representation of a model of a lung for illustrating the dead space and gas exchange portions of the lung pertinent to using a system according to the invention according to an embodiment of the invention depicted in FIG. 4 or 5. This model of the lung is further described with reference to FIG. 10 described below.
Figure 6C:
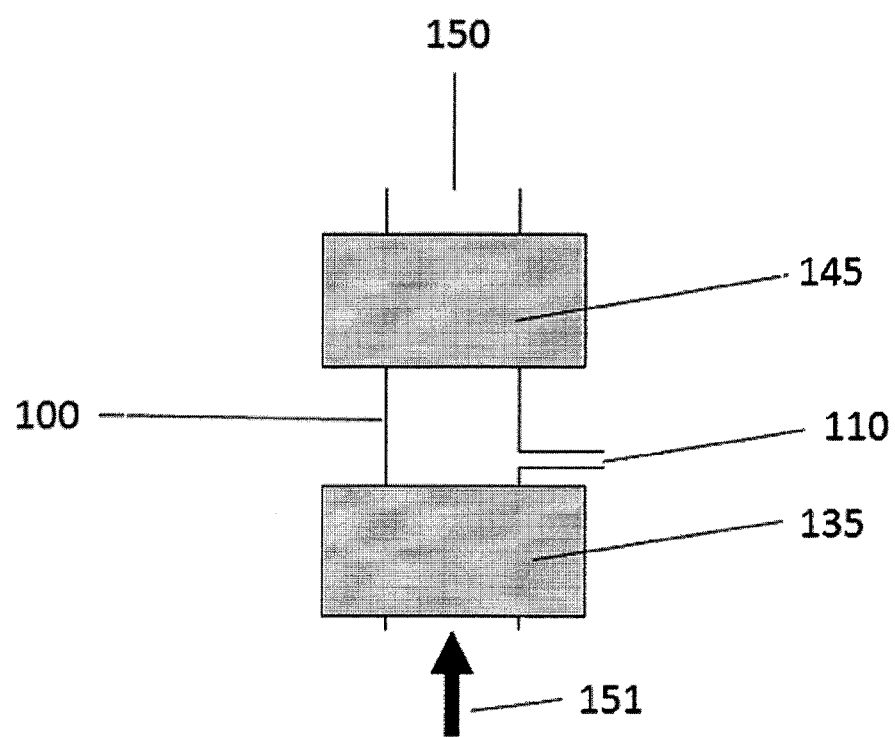
FIG. 6c is alternative configuration of the portion of the circuit shown in FIGS. 4 and 5 that is proximal to and includes one way inspiratory and expiratory valves; the alternative configuration obviating the need for these valves.

As seen in FIG. 6A, which diagrammatically depicts a subject's dead space 500 and alveolar 515 lung volumes, the respective gas compositions 510 and 520 of these volumes are similar when breathing on a sequential gas delivery circuit 101 (see FIG. 9) as a result of the subject inhaling an end tidal gas coming from the alveoli 520 at the end of an immediately preceding breath as opposed to the tail end of the gas composition tailored to the first portion a respective breath [i] in the previous breath which would otherwise occupy the dead space 500 (in the absence of an SGD circuit 101). FIG. 6b graphs end tidal $PCO_2$ readings (Y scale) derived from a capnograph (broken lines 545 demarcate transitions between exhalation cycles) illustrating the transition (demarcated by broken line 546) between values related to exhalation of dead space gas 535 and alveolar gas 540. These values are not that marked different so that an error in end tidal picking—values 530—will not radically alter the end tidal value.

Section A: Example 1—Present Invention

Figure 8A:
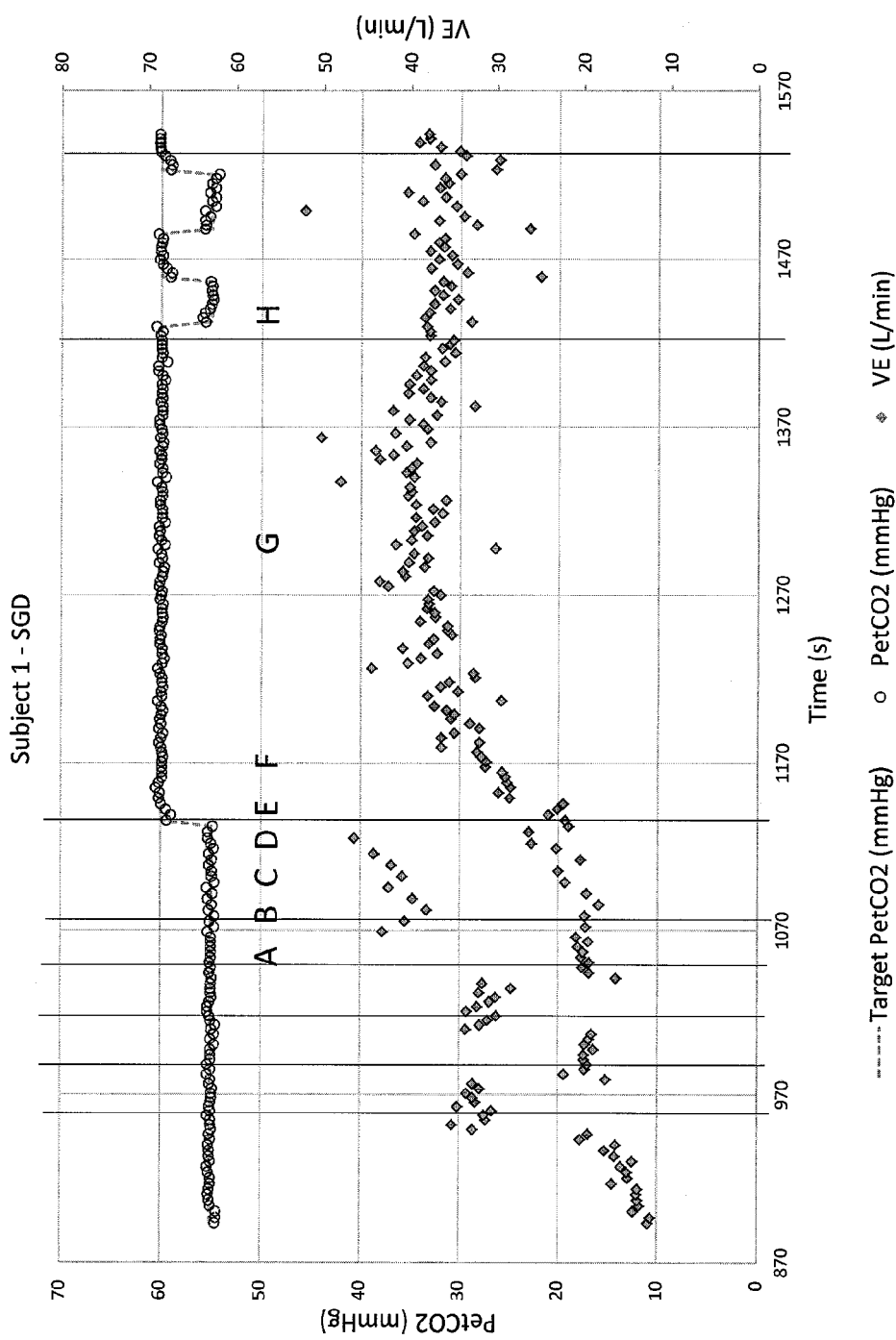
FIGS. 8a to 8f are graphs generated for Example 1 (for which the data is summarized in FIG. 7) organized to plot end tidal readings and minute volumes with respect to time. The graphs show the progression over time of three respective subjects' targeted and actual end tidal $PCO_2$s, as well as variations in their breath size quantified in terms of minute ventilation in L/min (plotted with respect to time on the y axis). End tidal gas X readings are shown corresponding to minute ventilation values on dual X-axes.
Figure 8B:
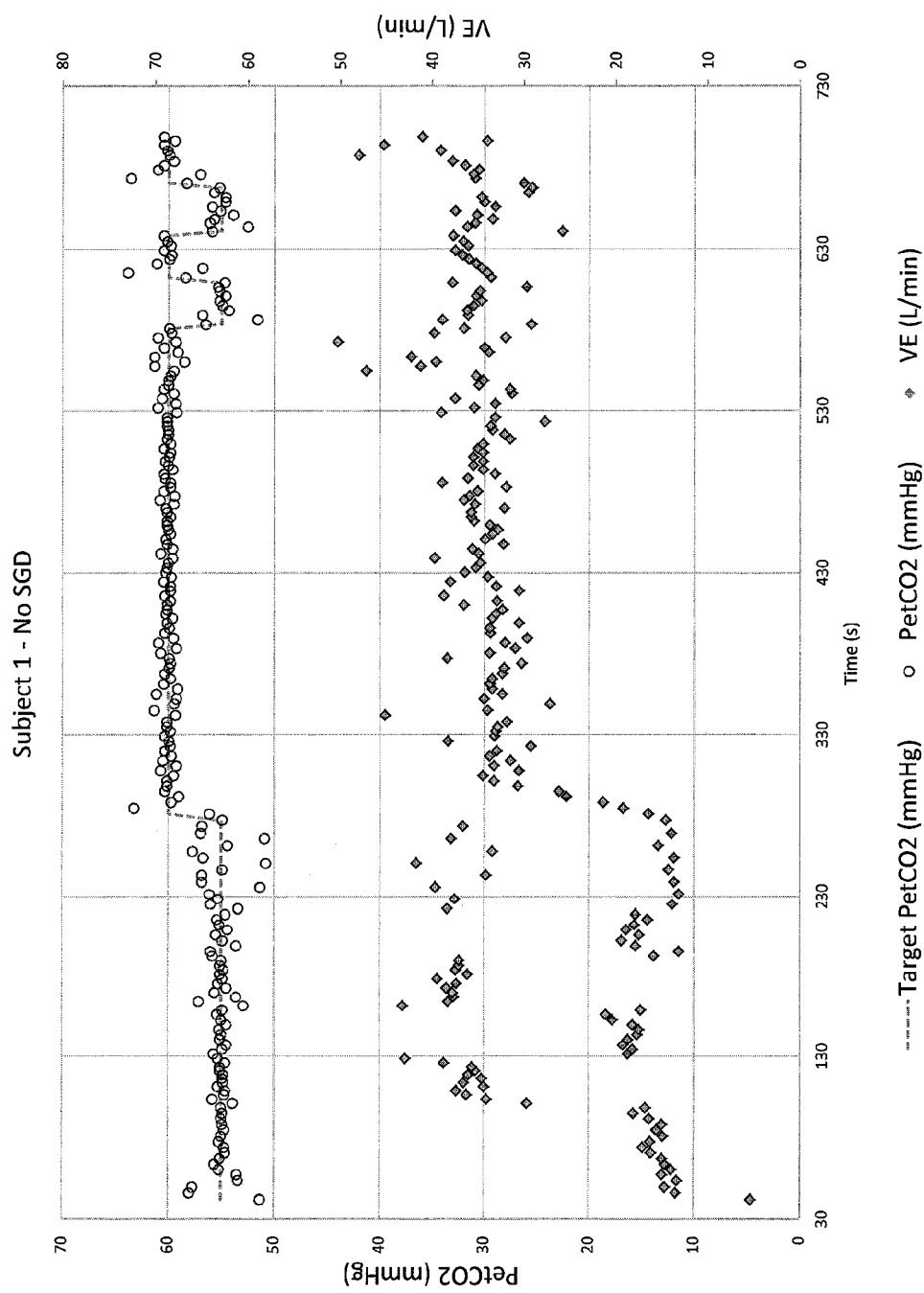
Figure 8C:
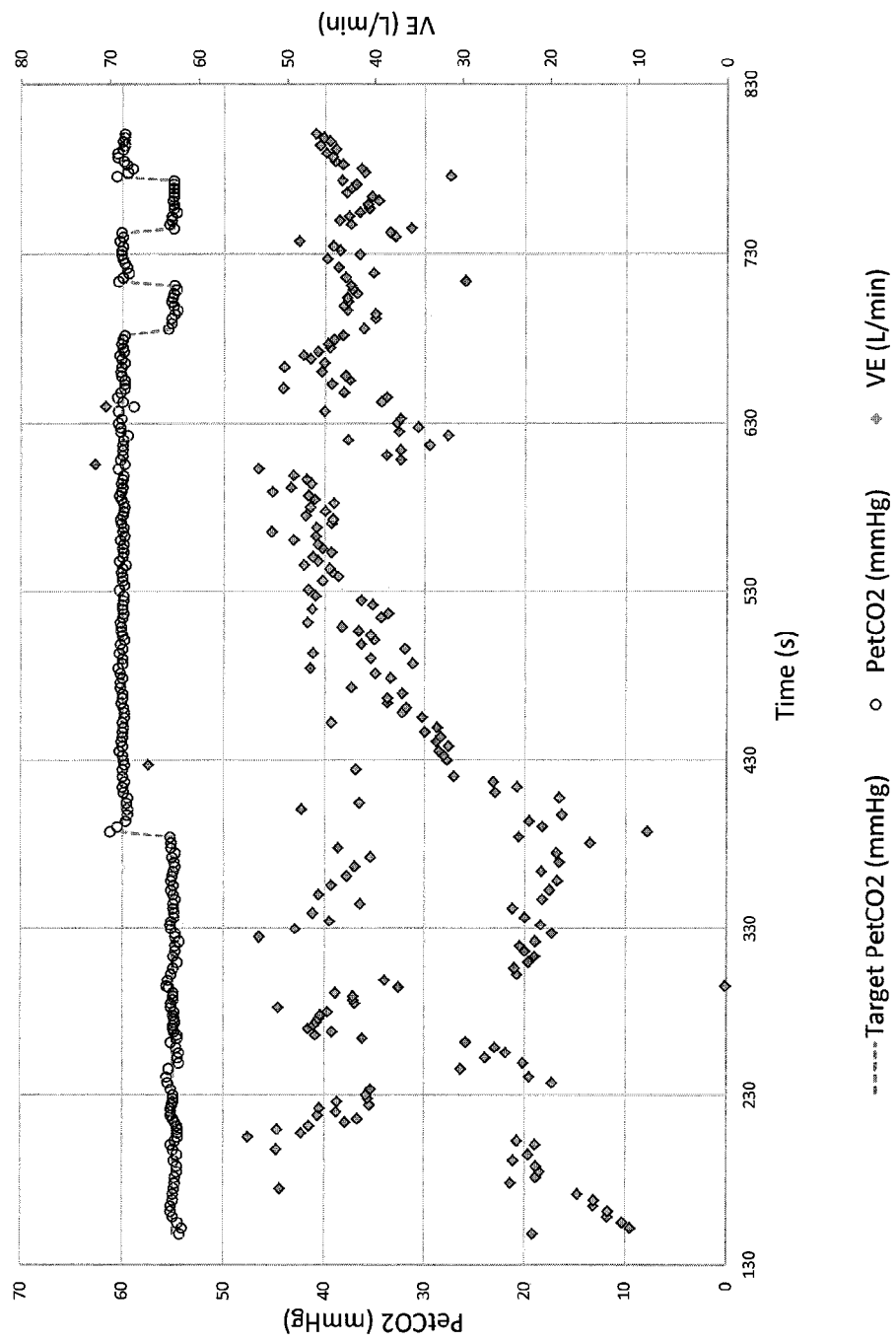
Figure 8D:
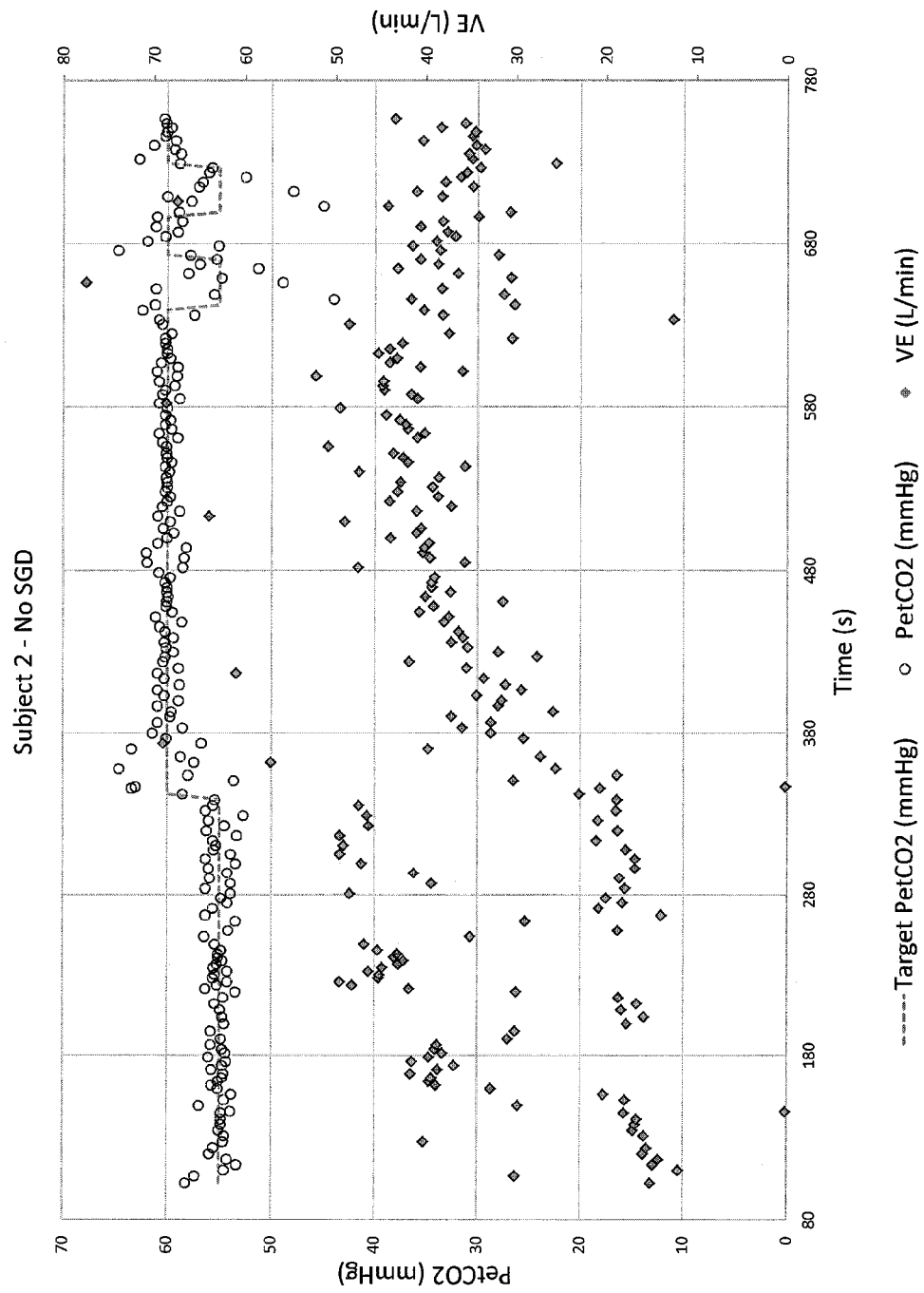
Figure 8E:
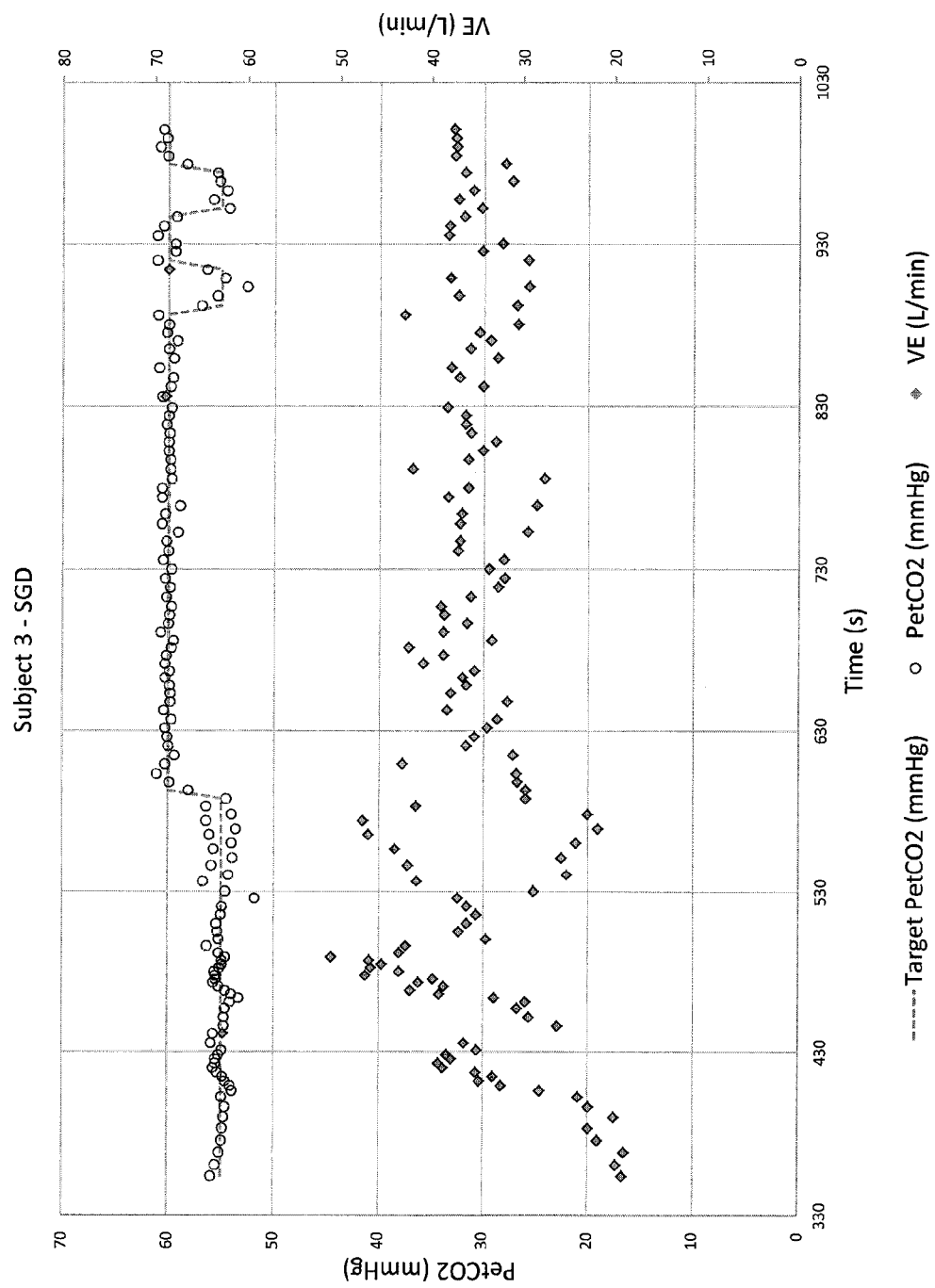
Figure 8F:
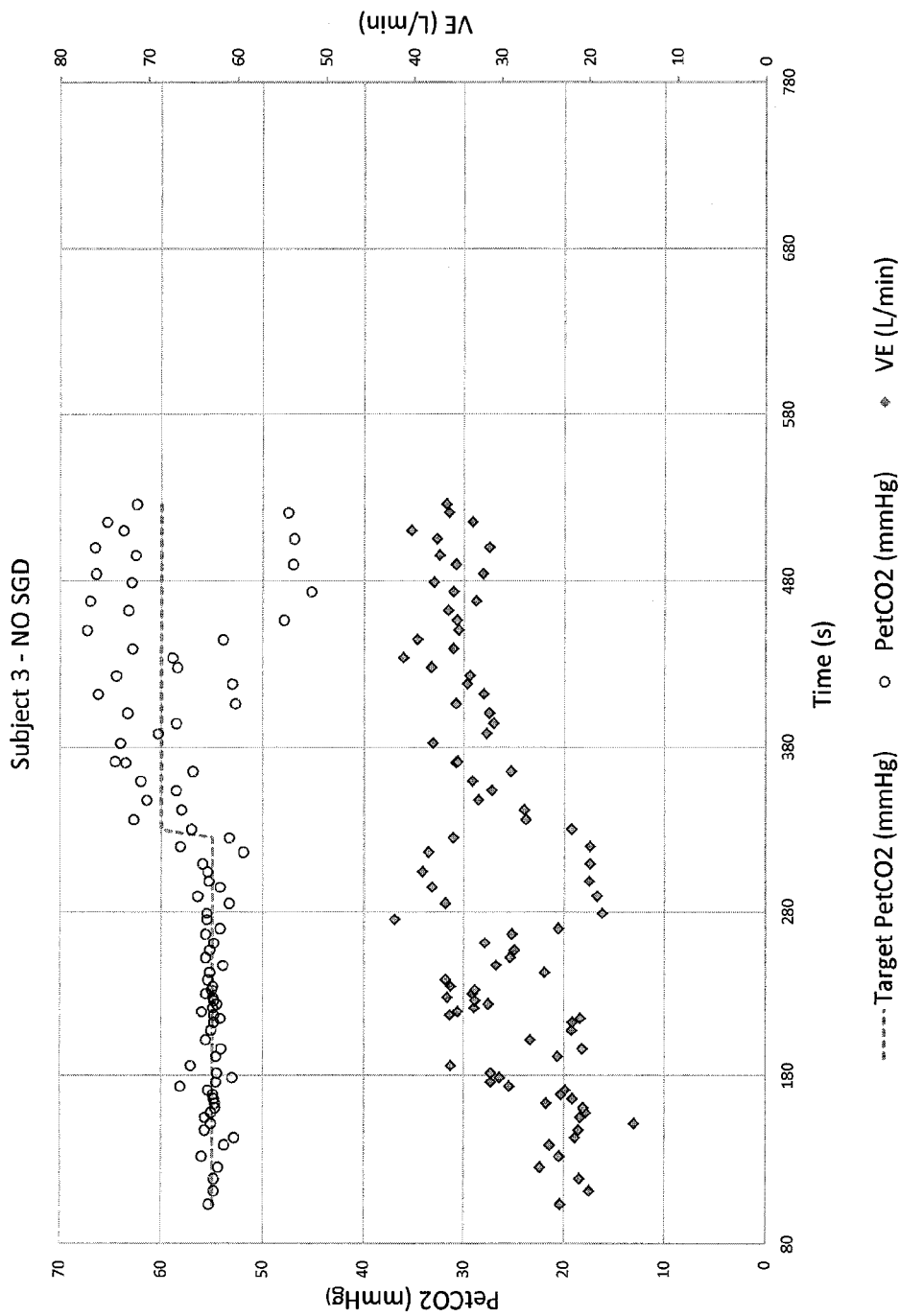

The system was used to control PetCO2 in spontaneously breathing subjects as described in the following table. This table is also reproduced for ease of reference as FIG. 8g.

| Stage | Ventilation | Target PetCO2 (mmHg) | Duration (min) |
|---|---|---|---|
| A | Natural | 55 | 1 |
| B | Hyperventilation | 55 | 0.5 |
| C | Natural | 55 | 0.5 |
| D | Hyperventilation | 55 | 0.5 |
| E | Natural | 55 | 0.5 |

-continued

| Stage | Ventilation | Target PetCO2 (mmHg) | Duration (min) |
|---|---|---|---|
| F | Alternating between hyperventilation and natural breathing each breath | 55 | 1 |
| G | Natural | 60 | 5 |
| H | Natural | Alternating between 55 and 60 every 0.5 min | 2 |

Three subjects were tested according to the above protocol. Hyperventilation implies that the subject was coached to double their minute ventilation; during natural breathing the subject was allowed to breathe as they felt comfortable. The test on the third subject without SGD had to be terminated early in stage G because of destabilization of the feedback system caused by a highly irregular natural breathing pattern. For each test, the error was calculated as the difference between the measured PetCO2 and target PetCO2, and the root mean square (RMS), standard deviation (SD), minimum (MIN), and maximum (MAX) error was computed.

The results are summarized in the FIG. 7 and FIGS. 8a-8f. As seen in FIG. 7 and FIGS. 8a to 8f a method and apparatus according to invention—implementing SGD—enabled the target end tidal values in each segment of the test to be approximated with reduced variability. Additionally, it is apparent that the difference between the target end tidal values and the actual values attained were higher without SGD that with SGD.

Section B: Description of Virtual Sequential Gas Delivery (VSGD) Invention

Virtual sequential gas delivery or virtual SGD (VSGD) is disclosed in our copending PCT application no. PCT/CA2013/000266 filed Mar. 19, 2013 and published under No. WO/2013/138910, the content of which is hereby incorporated by reference.

In many clinical and research situations, a subject is required to breathe through a breathing circuit. These circuits are normally designed to deliver different compositions of gases at different points throughout the breath cycle. In many cases, the breathing circuits are designed to minimize the use of an expensive component gas of the breathing mixture. These circuits, however, are normally designed with, and constructed from, components such as tubing, reservoir bags, and valves. These components are expensive, bulky, and prone to failure.

For example, the Hi-Ox 80 (CareFusion) breathing circuit is a breathing circuit designed to provide high inspired fractions of oxygen while minimizing the flow rate of oxygen to the patient. In this circuit, a constant flow rate of oxygen is provided to the circuit, the oxygen accumulating in a reservoir. The patient inspires through two one-way valves in parallel. The inlet side of the oxygen one-way valve is connected to the oxygen reservoir, while the inlet side of the air one-way valve is open to the atmosphere. The oxygen-supply one-way valve has negligible cracking pressure and so opens for any inspiratory effort. The air-supply one-way valve has a small cracking pressure which causes it to open only when a negative pressure is generated in the breathing circuit. In this way, during a typical inspiration, the patient inspires oxygen from the oxygen reservoir first. When the reservoir is empty, continued inspiration generates a negative pressure in the circuit thereby opening the air-supply one-way valve. Therefore, the balance of the breath is drawn from ambient air. Expiration is directed to the ambient atmosphere through a third expiratory one-way valve.

While this circuit is effective, it has a number of limitations. Firstly, the mechanical components are prone to failure. Failure of the one-way valves, such as a failure of the oxygen-supply one-way valve to open, may cause the subject to breath only ambient atmospheric air. Failure of the air-supply one-way valve to open will limit the subject's minute ventilation to the flow rate of oxygen to the circuit. On the other hand, if the oxygen-supply one-way valve does not effectively prevent back flow, the subject may expire into, and rebreathe from, the oxygen reservoir. Secondly, in addition to potential failures, the one-way valves increase the resistance to flow in the breathing circuit thereby increasing the work of breathing. This is uncomfortable for most patients, and may be a significant limitation to use in elderly patients or those with pulmonary disease. Thirdly, the size of the manifold which houses all the valves together with the reservoir can be quite large and cumbersome for some situations. For example, in an emergency medical resuscitation situation where access is required to the subject's chest, the oxygen reservoir may be in the way. Here, the physicians must remove the breathing circuit to access the chest.

According to one aspect, the VSGD invention is directed to a respiratory gas delivery system adapted to deliver an inspiratory gas of variable composition comprising:
A. a gas delivery apparatus operatively connected to a processor;
B. a flow sensor adapted to monitor in real time the rate of inspiration of a gas;
wherein, for a plurality of respective inspiratory cycles $[i]_1$ to $[i]_n$ and a plurality of time points $[t]_1$ to $[t]_n$, over the course of a respective inspiratory cycle $[i]$, the processor is configured to:
(a) use output from the flow sensor to monitor the cumulative volume of gas inspired in the respective inspiratory cycle at any given time point $[t]_1$ to $[t]_n$;
(b) execute an algorithm to determine a desired composition of the inspired gas based on whether or not at least one threshold cumulative volume of a desired gas composition has been inspired in the respective inspiratory cycle, the desired composition including a composition selected from a first composition selected for delivery for a first portion of a breath and at least one alternate nth composition; and
(c) generate a control signal effective to signal the gas delivery apparatus to deliver the first composition in the first part of breath and the nth composition during the course of a breath based on whether or not the at least one threshold cumulative volume has been reached.

Optionally, the first composition corresponding to a first portion of a breath is determined using at least one first criterion and the at least one alternate nth composition is determined using at least one different criterion.

Optionally, the at least one pre-determined cumulative volume is set to be less than a subject's tidal volume minus anatomic dead space volume such that the entire volume of the first composition is destined to enter a subject's alveolar space.

Optionally, the alternate composition is a neutral gas.

Optionally, the alternative composition is a percentage composition of a constituent gas as low as 0%, wherein the constituent gas is of a type determined by a user to warrant conservation by reducing delivery to the anatomical dead space.

Optionally, a threshold cumulative volume for a respective breath [i] may be set to deliver a target total inspiratory volume of a first gas composition over a series of inspiratory cycles $[i]_1$ of $[i]_n$.

By way of example only, n may be 7 and the series may include a current inspiratory cycle [i]. Delivering 500 ml of a gas over 7 breaths: If after 6 breaths, 470 ml of the gas has been delivered, in the $7^{th}$ breath the threshold volume is computed and set to be 30 ml.

Optionally, the processor is configured to simulate gas delivery from at least a virtual first gas reservoir and a second gas source, optionally a virtual second gas reservoir, wherein:

(a) the first gas reservoir and the second gas source e.g. gas reservoir contain a gas of at least specifiable or specified composition;

(b) at least the first gas reservoir is assumed to contain a gas corresponding to a first portion of a breath, the processor configured to send a control signal to signal to the gas delivery apparatus to deliver a gas of a specified composition of the first gas reservoir for the first part of a respective inspiratory cycle [i], the first gas reservoir set to contain a volume of gas adapted to be depleted in each inspiratory cycle at a reservoir specific depletion rate which tracks the inspiratory flow rate measured by the flow sensor; and (c) the processor generates a control signal effective to signal the gas delivery apparatus to deliver a gas of composition substantially equal to the specifiable or specified composition of the at least second gas reservoir for a second part of a respective inspiratory cycle [i] when the first gas reservoir is depleted.

Optionally, the volume of the at least first gas reservoir is set based on an assumption that the first gas reservoir is continually filled with a gas of a specified composition at a specifiable or specified reservoir-specific fill rate which is less than the reservoir specific depletion rate.

Optionally, the volume of the at least first gas reservoir is set based on an assumption that the first gas reservoir is full at the start of an inspiratory cycle, the volume selected to be a volume that can be predicted to be depleted at a reservoir specific depletion rate which tracks the inspiratory flow rate measured by the flow sensor.

Optionally, the apparatus is configured to deliver a first gas of a first composition for a first part of each inspiratory cycle [i] and a second gas of a second composition for a second part of each inspiratory cycle [i].

Optionally, the apparatus is configured to simulate gas delivery from two gas sources e.g. gas reservoirs, wherein the first gas source e.g. reservoir is exclusively depleted in a first part of each inspiratory cycle [i], and the second gas source e.g. reservoir is exclusively delivered in a second part of each inspiratory cycle [i]. The second gas source e.g. gas reservoir is optionally associated with a parameter such as volume or fill rate, however especially if the second gas source is set to have no volume limit, for example where the second gas source is drawn upon for the remainder of any given inspiratory cycle, whether or not it is depleted may be moot.

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

According to another aspect, the VSGD invention is directed to a computer program product or a programmable IC chip comprising program code for controlling a gas delivery apparatus which is adapted to deliver an inspiratory gas of variable composition comprising:

Program code for obtaining input from a flow sensor adapted to monitor in real time the rate of inspiration of a gas;

Program code for configuring a processor, for a plurality of respective inspiratory cycles $[i]^1$ to $[i]^n$, throughout each inspiratory cycle [i], to (a) use output from the flow sensor to monitor the volume of inspired gas in the respective inspiratory cycle; (b) execute an algorithm to compute, specify or obtain input of a desired composition of the inspired gas using as input at least the cumulative volume of inspired gas in the respective inspiratory cycle;

(c) generate a control signal effective to signal the gas delivery apparatus to deliver a gas of composition substantially equal to the computed composition.

Optionally, the program code configures the processor to simulate gas delivery from a plurality of gas reservoirs, wherein:

(a) each reservoir contains a gas of specifiable or specified composition;

(b) at least one reservoir (the one containing gas adapted to be delivered in a first portion of a breath), optionally each reservoir, is continually filled with a gas of the associated composition at a specifiable or specified reservoir specific fill rate;

(c) at least the one and optionally each reservoir is continually depleted at a specifiable reservoir specific depletion rate. Optionally, the sum of the individual depletion rates equal to the inspiratory flow rate measured by the flow sensor;

(d) wherein the program code configures the processor to generate a control signal effective to signal the gas delivery apparatus to deliver a gas of composition substantially equal to a blend of the reservoir gases weighted by their associated depletion rates.

Where a depletion rate is specified only for the gas reservoir containing a gas adapted to be delivered in a first portion of a breath the second reservoir may assumed never to be depleted, depleted over a time course corresponding to the duration of the remainder of a cycle of inspiration or depleted after consumption of a particular constituent gas over a period of use. Hence this model may be interchangeable with a model in which only one reservoir is present and depleted, the at least one gas of an alternative composition delivered only the remaining portion of an inspiratory cycle.

Optionally, the patient is a spontaneously breathing patient. Depletion of at least the first delivered gas represents an embodiment of an algorithm adapted to send a control signal to signal the gas delivery apparatus to deliver a gas of second composition which is specifiable or specified based on a different criteria which demarcates a juncture at or preceding the juncture at which inspired gas has already filled the alveoli and begins to fill the anatomical dead space, Accounting for the fact that some not all of an inspired gas will enter a subject's alveolar space is useful for a variety of purposes including enabling an expensive gas to be conserved or enabling a neutral gas or air to be delivered in each inspiratory cycle.

Optionally, the program code adapts the apparatus to deliver a first gas of a first composition for a first part of each inspiratory cycle [i] and a second gas of a second composition for a second part of each inspiratory cycle [i].

Optionally, the program code adapts the apparatus to simulate gas delivery from two gas reservoirs, wherein the first reservoir is exclusively depleted in a first part of a each inspiratory cycle [i], and the second reservoir is exclusively delivered in a second part of each inspiratory cycle [i].

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

According to one aspect, the VSGD invention is directed to a method using a gas delivery apparatus for delivering an inspiratory gas of variable composition and a computer program product or programmable IC chip adapted to implement the method, the gas delivery apparatus operatively connected to a processor, comprising A. obtaining output from a flow sensor adapted to monitor in real time the rate of inspiration of a gas;
B. using output from the flow sensor to monitor the cumulative volume of gas inspired in the respective inspiratory cycle at any given time point $[t]_1$ to $[t]_n$ over the course of a respective inspiratory cycle [i];
C. executing an algorithm to determine a desired composition of the inspired gas based on whether or not at least one threshold cumulative volume of a gas composition has been inspired in the respective inspiratory cycle, the desired composition including a composition selected from a first composition corresponding to a first portion of a breath and at least one alternate nth composition;
D. generating a control signal effective to signal the gas delivery apparatus to deliver the first composition in the first part of a respective inspiratory cycle [i] and at least one alternate nth composition during the course of the inspiratory cycle based on whether or not the at least one pre-determined threshold cumulative volume has been reached.

Optionally, the composition corresponding to a first portion of a inspiratory cycle is determined using at least one first criterion and wherein the at least one alternate composition is determined using at least one different criterion.

Optionally, the at least one pre-determined cumulative volume is set to be less than a subject's tidal volume minus anatomic dead space volume such that the entire volume of the composition corresponding to a first portion of a inspiratory cycle is destined to enter a subject's alveolar space.

Optionally, the alternative composition is a neutral gas.

Optionally, the alternative composition is a percentage composition of a constituent gas as low as 0%, wherein the constituent gas is of a type determined by a user to warrant conservation by reducing delivery to the anatomical dead space.

Optionally, the method and the computer program product simulate gas delivery from at least a virtual first gas reservoir and a virtual second gas reservoir, wherein:
(a) the first gas reservoir and the second gas reservoir contain a gas of specifiable or specified composition;
(b) at least the first gas reservoir is assumed to contain a gas corresponding to a first portion of a inspiratory cycle, the method comprising sending a control signal to signal to the gas delivery apparatus to deliver a gas of a specified composition of the first gas reservoir for the first part of a respective inspiratory cycle [i], the first gas reservoir programmed to contain a volume of gas adapted to be depleted in each inspiratory cycle at a reservoir specific depletion rate which tracks the inspiratory flow rate measured by the flow sensor;
(c) generating a control signal effective to signal the gas delivery apparatus to deliver a gas of composition substantially equal to the specifiable or specified composition of the at least second gas reservoir for a second part of a respective inspiratory cycle [i] when the first gas reservoir is depleted.

To carry out the method, the computer program product includes program code which specifies or enables specification of the composition of the first gas reservoir and the second gas reservoir, program code for sending a control signal to signal to the gas delivery apparatus to deliver a gas of a specified composition of the first gas reservoir for the first part of a respective inspiratory cycle [i]; program code for specifying the volume and/or fill rate of the first gas reservoir, wherein the first gas reservoir contains a volume of gas adapted to be depleted in each inspiratory cycle at a reservoir specific depletion rate which tracks the inspiratory flow rate measured by the flow sensor; and program code for generating a control signal effective to signal the gas delivery apparatus to deliver a gas of composition substantially equal to the specified composition of the at least second gas reservoir for a second part of a respective inspiratory cycle [i] when the first gas reservoir is depleted.

Optionally, the volume of the at least first gas reservoir is set based on an assumption that the first gas reservoir is continually filled with a gas of an associated composition at a specifiable or specified reservoir-specific fill rate which is less than the reservoir specific depletion rate.

Optionally, the volume of the at least first gas reservoir is set based on an assumption that the first gas reservoir is full at the start of an inspiratory cycle, the volume selected a volume that can be predicted to be depleted the reservoir specific depletion rate which tracks the inspiratory flow rate measured by the flow sensor.

Optionally, the method is adapted to deliver a first gas of a first composition for a first part of each inspiratory cycle [i] and a second gas of a second composition for a second part of each inspiratory cycle [i].

Optionally, the method is adapted to simulate gas delivery from two gas reservoirs, wherein the first reservoir is exclusively depleted in a first part of each inspiratory cycle [i], and the second reservoir is exclusively drawn upon e.g. depleted in a second part of each inspiratory cycle [i].

Optionally, the fill rate of the first reservoir is less than the subject's total inspired volume minus the total volume of gas inspired into the anatomic dead space volume over a measurement interval.

Optionally, the measurement interval is one minute.

Optionally, the composition of gas delivered in the second part of each inspiratory cycle [i] is neutral with respect to at least one constituent gas of the inspiratory gas.

Optionally, the cumulative volume in a respective inspiratory cycle [i] is computed to achieve a target total inspiratory volume of a gas of a first gas composition over a series of inspiratory cycles, the series optionally at least including the current inspiratory cycle [i].

For example, if a volume X (e.g. 500 ml) is set to be delivered over Y inspiratory cycles (e.g. 7 inspiratory cycles), the processor is programmed, e.g. after (Y−1) inspiratory cycles have delivered a volume Z (e.g. 470 ml of the gas) to compute the threshold volume for the last inspiratory cycle to be X−Z (i.e. 30 ml.).

According to one aspect, the VSGD invention is directed to a respiratory gas delivery system adapted to deliver an inspiratory gas of variable composition comprising:
A. a gas delivery apparatus operatively connected to a processor;

B. at least one device adapted to monitor at least one condition representing a juncture in a respective inspiratory cycle [i] which satisfies at least one the following criteria:
   a) a specifiable or specified volume of a desired gas composition has already been inspired in the respective inspiratory cycle;
   b) a specifiable or specified amount of at least one constituent gas X has been inspired in the respective inspiratory cycle;
   c) a volume of gas yet to be inspired in the respective inspiratory cycle exceeds a subject's anatomical dead space volume;
wherein, for a plurality of respective inspiratory cycles $[i]_1$ to $[i]_n$, the processor is configured to:
(a) use output from the at least one device to monitor the at least one condition based on the at least one criteria;
(b) execute an algorithm to determine a desired composition of the inspired gas based on whether or not the condition is satisfied, the desired composition including a composition selected from a first composition selected for delivery for a first portion of a inspiratory cycle and at least one alternate nth composition;
(c) generate a control signal effective to signal the gas delivery apparatus to deliver the first composition during a first portion of an inspiratory cycle at least one alternate composition during the course of a inspiratory cycle based on whether the condition is satisfied.

The device may include at least one of a measurement device such as a flow sensor, gas analyzer or a pressure sensor, a device adapted to control the tidal volume of a subject (e.g. a ventilator), a subject operated input device or a prompting device. A subject operated input device may be of any time in which enables a subject to signify the commencement of an end of an inspiratory cycle (i.e. winding down of the subject's inspiratory effort). A prompting device may include a device which enables a subject to readily target a value within range of values of a parameter that is correlated to volume of or duration of an inspiratory effort. Optionally, the system includes at least one measurement device that monitors in real time the cumulative volume of gas inspired in at least a first portion of an inspiratory cycle. Optionally, the system includes at least one measurement device that monitors in real time the pressure in a patient airway interface or conduit leading to patient airway interface, for example to monitor the progression, commencement and/or completion of an inspiratory and/or expiratory effort. Optionally, the system includes at least one measurement device that monitors in real time the concentration of at least one constituent gas.

According to one embodiment, the VSGD invention is directed to simulating a breathing circuit of a respiratory gas delivery system (a reference circuit and a reference system) using an alternative system so that the gas delivered to the patient—at least one of flow and composition—is substantially the same when using the alternate system and the reference circuit (i.e. with respect to a given output—flow or composition or both—the two circuits are functionally interchangeable at least in the sense that the alternate system performs the function of the reference system, albeit, optionally, in at least one respect, in a relatively advantageous manner. For example, the alternative system may be safer (e.g. less prone to failure), more robust, less bulky from the standpoint of making caregiver access to the patient easier, etc.

Functional equivalence, in term of flow, means that the pattern of flow. In at least one aspect, this alternate system of the invention virtualizes components of the reference breathing circuit in the sense that a control algorithm of the alternative system supplants structural features (e.g. at least one structural component) of the reference circuit, for example, a physical gas reservoir with an accumulator in computer memory.

Thus, according to one aspect, the VSGD invention is directed to a respiratory gas delivery system adapted for use with a first breathing circuit, the first breathing circuit optionally having at least one gas conduit leading to a patient airway interface, characterized in that the respiratory gas delivery system virtualizes at least one structural feature, optionally at least one structural component, optionally at least one set of structural parts of a reference, second breathing circuit, the respiratory gas delivery system including:
   a) at least one device adapted for selecting a juncture during an inspiratory cycle for switching between a first gas composition and at least one alternate, nth gas composition, optionally a juncture that demarcates a juncture preceding a point at which inspired gas has already filled the alveoli and begins to fill the anatomical dead space, optionally a juncture identified by monitoring at least one parameter in real time, optionally a parameter selected from at least one of volume, pressure and gas concentration, optionally volume, optionally a flow sensor, positioned in relation to the first breathing circuit, for at least determining the volume gas inhaled via the patient airway interface;
   b) a gas delivery apparatus for delivering a gas comprising a plurality of component or constituent gases into the patient airway interface, the gas delivery apparatus operatively connected to a computer; and optionally
   c) a gas analyzer for analyzing the gas concentration of one or more gases inhaled and/or exhaled by the subject;
wherein the computer is optionally configured to supplant the at least structural component, optionally at least one set of structural parts of the reference breathing circuit, the set of structural parts optionally including at least one part selected from a gas reservoir, a valve and a conduit, by using at least one of an algorithmic and a mathematical model of the at least one set of structural parts to generate gas delivery characteristics that simulate the functions of said set of structural parts. Optionally, the at least one set of structural parts simulated by a respiratory gas delivery system according to the invention comprises or consists of a set of structural parts adapted to direct gas flow from a first circuit flow path, optionally adapted to be open at the start of each inspiratory cycle, to at least one alternate, nth (e.g. second) circuit flow path during the course of a given inspiratory cycle. Optionally, the first circuit flow path is adapted to provide a gas of a first gas composition and the at least one alternate flow path is adapted to provide gas of at least one alternate nth gas composition. Optionally the first circuit flow path is operatively connected to a first gas source (the system simulates gas flow characteristics of the first gas source, optionally a maximum volume or rate of flow and/or a composition) optionally a first gas reservoir and the respiratory gas delivery system of the invention simulates cyclical replenishment and depletion of at least first gas reservoir. Optionally, the at least one alternate nth circuit flow path of the reference breathing circuit is a second gas source and the system of the invention simulates the gas flow characteristics of at least one second gas source, optionally the composition of the at least one second gas source. Optionally, the at least one second gas source is a reservoir, optionally a reservoir that holds a subject's exhaled gas, the at least one alternate circuit flow path of the reference breathing circuit optionally adapted to deliver the subjects last expired gas from the immediately preceding breath first.

According to one embodiment, the respiratory gas delivery system of the VSGD invention accounts for how the supplanted component(s) of a reference breathing circuit work within a reference respiratory gas delivery system which the system of the invention simulates qualitatively and/or quantitatively, for example so that the respiratory gas delivery system of the invention is functionally equivalent (able to perform the same functions), to the extent desired (a system of the invention can be considered to function equivalently to a reference system if it performs the same general function without one or more limitations or inessential attributes), to the reference system.

As exemplified herein, at least one principal physical difference between two systems, apart from the computer control system, lies in differences between the first breathing circuit and the reference (second) breathing circuit. Implicitly, if the first breathing circuit and a reference breathing circuit (denoted for convenience as a "second" breathing circuit) are different, the respiratory gas delivery system of the VSGD invention, having regard to its operation within any reference respiratory gas delivery system, can be made compensatorily equivalent to the extent that the two systems are to intended to generally function equivalently. For example, features of the system of the invention and reference gas delivery system that may be made equivalent by simulating the features of the reference system may include a rate of flow from the gas delivery apparatus, cessation of flow e.g. to a patient airway interface (such as a breathing mask) to simulate cessation of flow upon expiration or a change of composition (e.g. volume triggered, for example, depletion of a volume of gas in a gas reservoir that is cyclically replenished, and depleted by inspiration) to simulate switching access between a gas reservoir and another flow path leading from an alternate gas source, optionally a reservoir or inlet, that may be used to introduce gas of a potentially different composition.

Accordingly, the VSGD invention is also directed to a respiratory gas delivery system including, or adapted for use with, a first breathing circuit optionally having at least one gas conduit leading to a patient airway interface, characterized in that the respiratory gas delivery system virtualizes gas flow characteristics of a reference respiratory gas delivery system that includes a reference breathing circuit, the gas flow characteristics of the reference respiratory gas system dictated at least in part by structural features, for example components or parts, of the reference breathing circuit, the respiratory gas delivery system including:
  a) a flow sensor, optionally positioned in or proximal to the patient airway interface; for determining, for example, the volume of gas entering the patient airway interface in a given breath or breath segment e.g. an inspiratory cycle or any portion thereof);
  b) a gas delivery apparatus adapted to deliver a gas (the gas optionally comprising a plurality of component or constituent gases) into the patient airway interface, optionally into the gas conduit (the gas delivery apparatus may include an on-board computer for controlling the gas delivery apparatus and/or may adapted to receive input from an external computer); and optionally
  c) a gas analyzer, for determining, for example, the composition of gas exhaled by a subject, optionally at the end of exhalation, wherein the gas analyzer is optionally positioned in or proximal to the patient airway interface; and optionally
  d) a pressure transducer, optionally positioned in or proximal to the patient airway interface for determining, for example the beginning and end of each inspiratory cycle
wherein the computer is programmed to control the gas delivery characteristics, particularly the gas output characteristics of the gas delivery apparatus such that the gas output characteristics of the gas delivery apparatus supplant structural features of the reference breathing circuit that dictate, at least in part, delivery characteristics of the reference respiratory gas delivery system.

The term "gas delivery characteristics" means any characteristic of a reference breathing circuit that affects gas flow to a subject that is dictated at least in part by a component of the circuit that is absent in the first breathing circuit. Optionally, the gas flow characteristic is dictated by one or more components or parts selected from a valve and a gas container such a reservoir, a conduit or compliance. Gas "delivery characteristics" or "flow characteristics" may include circuit pressure, the concentration of a gas constituent in a gas or in a component of a gas (for example as dictated by a change in the source or path of flow from a first circuit flow path to an alternate circuit flow path from which a gas of different composition emanates,) a rate or volume of flow of a gas or gas component or constituent, flow generation or restriction (e.g. via a valve such as a one-way valve, a proportional control valve, a PID control valve or an on/off type) or release of a flow restriction (e.g. via a valve) including the chronology of same (for example, the order/timing of delivery of component gases, for example from alternative sources or flow paths, such as imposed by a passive valve (which may have a predetermined opening pressure) or active valve (e.g. a balloon valve), and the capacity, qualitative and optionally quantitative, to accumulate a gas such as in a compliance, conduit or reservoir. In one embodiment, as described below, the respiratory gas delivery system virtualizes the gas delivery characteristics of a reference delivery system employing a sequential gas delivery circuit, for example, of the type having an inspiratory gas reservoir (which may be replenished—e.g. filled at a selected rate), an expiratory gas reservoir or ambient air inlet, and a flow control system which allows gas to flow to the patient from the expiratory gas reservoir or ambient air inlet, only when the inspiratory reservoir is temporarily emptied (it may be refilled, for example by the gas delivery apparatus e.g. in the form of a gas blender before each next inspiratory cycle).

The term "reservoir" means a containment chamber, optionally of defined volume and may include a bag, tubing etc. The term "flow control system" or "air flow control system" means a system in which components or parts such as valve(s) and conduit(s) control the origin and/or destination of flow when alternative airflow pathways are exploitable.

The term "component" used in the context of the phrase structural component of a breathing circuit means any portion of a breathing circuit and includes an assembly of interacting parts designed to perform a function, for example an inspiratory limb of a breathing circuit, an expiratory limb of a breathing circuit, a reservoir with an inlet and outlet portion etc. The term part is used interchangeably with the proviso that the term part in this connection denotes any part, but in contrast to component is not intended to denote an assembly of parts if any part is of the type that would typically be produced or sold as an indivisible unit i.e. a part is exemplified by a part of a valve or a valve typically produced or sold as a unit but not a valve connected between two independent air conduits.

The term "computer" is used broadly to refer to any device (constituted by one or any suitable combination of components) which may be used in conjunction with discrete electronic components and/or parts e.g. valves to perform the functions contemplated herein, including computing and obtaining input signals and providing output signals, and optionally storing data for computation, for example inputs/outputs to and from electronic components and application specific device components as contemplated herein. As contemplated herein a signal processor or processing device in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a pressure transducer, a gas analyzer, any type of input device for inputting parameters or values (for example, a knob, dial, keyboard, keypad, mouse, touch screen etc.), input from a computer readable memory etc. Key outputs may include output to a flow controller (e.g. PI control or PID control etc.). The term "processor" and "computer" are used interchangeably.

Excluded from the VSGD invention are respiratory gas delivery systems used to monitor pressure in a system to control active valves leading to two physical reservoirs containing gases of differing compositions. The system of the invention obviates reliance on two circuit flow path leading to two gas reservoirs, and the related requirement to coordinate flow between the paths, for example, if desired to avoid any interruption in flow or conjoining of different sources of gas flow.

The term "virtualizes" refers to programmed gas delivery in accordance with a model of a practical or "theoretical" circuit, the virtual circuit of the model replacing or obviating completely ("supplanting") structural features of a reference gas delivery system, particularly at least one component of a reference breathing circuit, which the reference delivery system is adapted to operate with. The structural component(s) is thereby supplanted by delivery apparatus output characteristics.

The term "sequential gas delivery (SGD for short) valve" means any valve that enables two gases to be delivered in sequence when a physical or virtual criterion is met. For example, the criterion may be depletion of a reservoir set to contain a limited amount (e.g. expressed as volume) of a gas so that at least one other gas is delivered in the same breath. Such a physical valve may be an active valve (e.g. a balloon valve) or a passive valve with an elevated opening pressure which provides for gas flow e.g. in the context of a rebreathing circuit, responsive only to depletion of a first gas source which is accessible at a lower pressure e.g. via a valve with a lower opening pressure (see FIGS. 2 and 3 and WO/2004/073779 which discloses examples of such valves and related circuits).

According to one embodiment of the VSGD invention, a theoretical circuit is exemplified by a circuit can be idealized to function free of a particular limitation that is hard to realize to a near ideal extent in practice, but for the invention which simulates the circuit functioning close to ideally (e.g. in at least one manner selected from less complex, less bulky, less prone to failure, capable of instantaneous changes in composition to simulate switching between different gas sources e.g. where cessation of flow from one source and commencement of flow from another source is hard to synchronize when the sources are switched physically as opposed to virtually e.g. by modeling the sources and the criteria for switching e.g. temporary depletion of a source which is alternately replenished and depleted at a selectable or ascertainable rate, triggering flow from an alternate source when depleted (in virtual terms—a change in composition upon depletion where the criterion for specifying the composition, if variable, from that alternate source, so dictates). Such a virtual circuit can be seen to do away with the switching apparatus of a breathing circuit (optionally including the physical source itself e.g. a gas reservoir, as well as associated gas conduits and valves e.g. an SGD valve) and the need for multiple physical sources of the breathing circuit. Modeling of the sources can be accomplished in terms of at least one parameter selected from composition and pattern of flow including at least one of rate of flow, volume of flow, duration of flow, flow pressure.

Optionally, the gas delivery characteristics of the reference breathing circuit are dictated in part by an inspiratory limb of the circuit including an inspiratory gas reservoir. The inspiratory gas reservoir may be supplanted in the first breathing circuit by control of the gas delivery apparatus so as to simulate replenishment e.g. filling (simulated by flow to the patient of a component gas of first composition) and depletion (for example, as measured by a flow sensor positioned to measure the actual inspiratory flow rate of a subject) of the inspiratory gas reservoir (arrest of flow of the component gas of first composition). The term "inspiratory gas reservoir" is used to refer to a reservoir for a gas composition that provides the first part of the gas content of each breath, for example: (1) the patient's primary respiratory requirements or (2) a gas that is primarily intended to create a concentration gradient to promote gas exchange with the pulmonary circulation. By contrast, the goal of delivering an exhaled gas or gas of similar composition (a neutral gas) is on the contrary (intended to avoid creating such a concentration gradient) except, optionally, in so far as its delivery is also secondarily intended to conserve a gas e.g. oxygen, an anesthetic or other therapeutic/diagnostic gas.

The term "delivery" or "deliver" is used to refer to making a gas available to a subject for inspiration and does not imply that a pressurized source is opened to a subject. For example, a gas may be made available from a reservoir or conduit (passively) when no resistance exists to its inhalation or such resistance is able to be overcome by an inspiratory effort of a subject with or without mechanical assistance.

Optionally the flow characteristics of the reference breathing circuit are dictated in part by a flow control system which directs gas flow from a first source or circuit flow path for a first gas component, for example an inspiratory reservoir of the reference breathing circuit, to an alternate source or circuit flow path for a second gas component, for example, an air intake port or a second gas reservoir (for example an expiratory gas reservoir) when structural features of the reference breathing circuit arrest flow from the first gas source, for example when the volume of the inspiratory reservoir is depleted or when a valve is set to restrict flow from the first gas source. The flow control system is optionally supplanted in the first breathing circuit by programmed gas output characteristics which first match those of the first gas source or circuit flow path, and subsequently, corresponding to when flow switches to the alternate gas source or circuit flow path, match those of the alternate gas source or circuit flow path. For example, the gas flow characteristics may include concentration and/or volume of at least one constituent of gas emanating from the first gas source or circuit flow path (a constituent of the first gas component) and the concentration of at least one constituent gas of the gas emanating from the second gas source or circuit flow path (a constituent of the second gas component).

According to one aspect, the VSGD invention is directed to a respiratory gas delivery system including or adapted for use with a first breathing circuit optionally comprising or consisting of at least one gas conduit leading to a patient airway interface, characterized in that the respiratory gas delivery system is adapted to virtualize, for example, simulate the function, for example selected gas flow (delivery) characteristics, of a reference respiratory gas delivery system which includes or is adapted for use with a second, reference breathing circuit, that is structurally different (e.g. less wasteful of gas and/or less complex (e.g. fewer parts or parts more easy to assemble, integrate or coordinate) and/or less bulky, and/or less expensive and/or less prone to failure or physical limitations), the respiratory gas delivery system including:
  a) a flow sensor, optionally positioned in or proximal to the patient airway interface;
  b) a gas delivery apparatus adapted to deliver a gas comprising a plurality of component or constituent gases into the patient airway interface, optionally into the gas conduit (the gas delivery apparatus may include an on-board computer for controlling the gas delivery apparatus and/or may adapted to receive input from an external computer); and optionally
  c) a gas analyzer, wherein the gas analyzer is optionally positioned in or proximal to the patient airway interface;
wherein control of the gas delivery apparatus simulates selected flow characteristics of the reference gas respiratory gas delivery system that:
  1. are defined at least in part by structural features, for example, structural parts of the reference breathing circuit;
  2. define the source or circuit flow path and/or order of delivery of one or more component gases, and/or the composition and volume of the gas or a component or constituent of the gas made available for inspiration in a breath, series of breaths, breath segment or series of breath segments, or time period;
and wherein the computer is programmed provide inputs to the gas delivery apparatus to:
  A) control the gas delivery apparatus by executing an algorithm that employs as inputs data obtained from the flow sensor (and optionally the gas analyzer) and at least a mathematical model of the second, reference breathing circuit, including parameters that describe supplanted structural features e.g. structural parts of the second, reference breathing circuit, the supplanted features e.g. structural parts:
    a. defining at least in part the selected gas delivery characteristics;
    b. absent in the first breathing circuit; and
  B) generate an output signal to the gas delivery apparatus that accounts for the supplanted structural features of the second, reference breathing circuit, such that when the respiratory gas delivery system outputs gas to the first breathing circuit the selected gas output characteristics of the respiratory gas delivery system simulate portions of the reference respiratory gas delivery system defined by the supplanted parts of the second reference breathing circuit.

In one embodiment of the VSGD invention, the reference breathing circuit is a rebreathing circuit including an inspiratory gas reservoir that is absent in the first breathing circuit, the computer programmed to obtain input of at least one rate at which the inspiratory gas reservoir is filled and at least one rate at which the inspiratory gas reservoir is emptied and to control the gas delivery apparatus to deliver a carbon dioxide containing gas after simulated depletion of the inspiratory gas reservoir.

In one embodiment of the VSGD invention, the reference breathing circuit is a rebreathing circuit including an inspiratory gas reservoir and an expiratory gas reservoir that are absent in the first breathing circuit, the computer supplanting the inspiratory and expiratory gas reservoirs, optionally by obtaining input of at least one rate at which the inspiratory gas reservoir is filled (this is optional since a first gas reservoir of a selected volume can simply be assumed to be replenished at beginning of each inspiratory cycle) and at least one rate at which the inspiratory gas reservoir is emptied, and controlling the gas delivery apparatus to deliver a carbon dioxide containing gas after each simulated depletion of the inspiratory gas reservoir. A rebreathing circuit may be a sequential gas delivery circuit if component gases are delivered in sequence. A sequential gas delivery circuit does not imply that the gas delivered after the first gas composition is or has the composition of at least one component e.g. $CO_2$ of an exhaled gas in an amount corresponding to a last exhaled end tidal gas, or a target concentration of an end tidal gas if the respiratory gas delivery system is adapted to control same.

In one embodiment, the respiratory gas delivery system includes a gas analyzer and the reference breathing circuit is a sequential gas delivery circuit. The first delivered gas may be of a composition that primarily corresponds to the patient's physiological and/or therapeutic gas requirements while the second delivered gas may be exhaled gas or a gas formulated by the gas delivery apparatus e.g. a gas blender containing at least those constituents of the exhaled gas in amounts that justify its delivery e.g. delivery of carbon dioxide in amount that represents its intended function as a "neutral gas" as defined below.

In one embodiment, the respiratory gas delivery system includes a gas analyzer, and the reference breathing circuit comprises an inspiratory gas reservoir, an expiratory gas reservoir and air flow control system for directing the flow of gas to the patient only when the inspiratory gas reservoir is depleted. The airflow control system may typically include one or more active and/or passive valves (activated when a threshold pressure is reached, e.g. negative pressure resulting from depletion of the inspiratory gas reservoir). The reference breathing circuit may include a flow control system including a by-pass limb interconnecting an inspiratory and expiratory limb of the circuit or a by-pass limb located exclusively within an expiratory limb of the circuit and therefore functioning to utilize negative inspiratory pressure to draw on the expiratory gas flow path when gas sourced from inspiratory flow path is depleted. Alternatively, one or more active valves can be used to effect sequential gas delivery (see US Patent Publication No. 2007/0062534). The inspiratory reservoir, expiratory gas reservoir and/or flow control system may absent from the first breathing circuit. The gas delivery apparatus may be programmed to control the concentration and rate of flow of the gas to simulate one or more cycles of filling and depletion of the inspiratory gas reservoir, optionally based on at least one rate of flow of gas into the inspiratory gas reservoir and at least one rate at which the inspiratory gas reservoir is depleted, and where input of at least one constituent of the gas exhaled by the subject is obtained from the gas analyzer for setting the gas delivery apparatus to (e.g. subsequently or contemporaneously) deliver a gas containing the at least one constituent in a selected concentration, for example a concentration that matches or approximates the concentration measured by the gas analyzer (optionally carbon dioxide).

With reference to any aspect of the VSGD invention, in one embodiment, the second, reference breathing circuit is a rebreathing circuit, and the gas delivery apparatus optionally simulates filling of an inspiratory gas reservoir at a rate of flow that is less that the subject's minute ventilation minus anatomic dead space ventilation. In this manner, the entirety of a first delivered gas of selected composition makes its way into the alveolar volume of the lung (as opposed to the anatomic dead space). A gas that has a composition that corresponds to that of subject's exhaled gas from a breath n−1 may then be delivered in each breath n, for example, upon simulated depletion of the inspiratory gas reservoir. In a broader sense, the second delivered gas may a "neutral gas" (defined below), for example, in the sense that its composition, in terms of at least one of its constituents e.g. carbon dioxide, contributes minimally to establishing a partial pressure gradient between the lung and pulmonary circulation. In one embodiment, the selected gas output characteristics comprise at least one of the following:

(i) the order or timing of delivery of two components of the gas, for example, wherein delivery of one component of the gas is first, followed by, a second component of the gas, optionally, delivery of the first component ceasing pending delivery of second component of the gas and vice versa, in cycles. Preferably the respiratory gas delivery system simulates a reference respiratory gas delivery system in which the rate of flow of the first component is less than the subject's minute ventilation minus anatomic dead space ventilation such the entire volume of the first delivered component enters the alveolar space, in each cycle, the second component being a neutral gas;

(ii) the volume and composition per breath or breath segment of the gas or at least one constituent of the gas;

(iii) the volume of a component or constituent of the gas relative to a total delivered volume of the gas, over a plurality of breaths or breath segments or over any time period [t];

(iv) a concentration of at least one component or constituent of the gas in each incremental unit of volume of the gas output from the gas delivery apparatus;

(v) a subject's effective alveolar ventilation in a breath [i] or over a plurality of breaths [n] or over a selected time period [t]. The term "effective alveolar ventilation" means the part of the volume of delivered gas that reaches the alveoli and establishes a concentration gradient for gas exchange (excludes the "neutral gas" component).

According to one aspect, the VSGD invention is directed to a respiratory gas delivery system adapted for use with a first breathing circuit having at least one gas conduit leading to a patient airway interface, characterized in that the respiratory gas delivery system virtualizes structural components a reference breathing circuit, the respiratory gas delivery system including:

a) a flow sensor, positioned for at least determining the volume gas inhaled via the patient airway interface;

b) a gas delivery apparatus including or controlled by a computer for delivering a gas comprising a plurality of component or constituent gases into the patient airway interface; and optionally c) a gas analyzer for analyzing the gas concentration of one or more constituent gases inhaled and/or exhaled by the subject;

wherein the computer is programmed to supplant one or more components of the reference breathing circuit by using a mathematical model of the supplanted structural components to generate gas delivery characteristics that supplant said components.

As suggested, the term supplants includes making one or more components superfluous (unnecessary to have a physical counterpart in the first breathing circuit) or replacing it/them with another/other component(s), for example, such that the supplanted circuit needs fewer, and/or less bulky and/or less complex or costly and/or components less prone to failure.

Optionally, the respiratory gas delivery system comprises virtual components which simulate components of a reference breathing system.

For example, in one embodiment, the supplanted component is an inspiratory gas reservoir which may be superfluous in the first breathing circuit. For example, the respiratory gas delivery system may be programmed to deliver a gas which, in effect, repeatedly (cyclically) provides the composition of the inspiratory gas reservoir in volumes which match the virtual content of inspiratory gas reservoir as it filled and refilled virtually having regard to the timing rate of flow in and out of the virtual reservoir, so that a counterpart physical reservoir is obviated in the first breathing circuit and accordingly in the design of the respiratory gas delivery system as a whole.

For example, in one embodiment, the supplanted component is a sequential gas delivery valve or valve set which may be superfluous in the first breathing circuit. A sequential gas delivery valve or valve set means a valve or valve set that alternately directs flow from a first flow path to a second flow path, for example so that differently constituted and/or sourced gases may be delivered, for example a first gas that supplies some part of the content requirements of the gas inspired in a given inspiratory cycle and a second gas that supplies the other part of that content (for example a "neutral" gas e.g. an end tidal gas. For example, the respiratory gas delivery system may be programmed to first deliver a gas which, in effect, repeatedly (cyclically) provides the composition of an inspiratory gas reservoir, and then ambient air inlet or the putative content of a virtual second gas reservoir. Accordingly, in terms of physical components of the first breathing circuit a single conduit leading to the patient airway interface may replace the aforementioned valves and optionally a second gas reservoir e.g. an expiratory gas reservoir.

The term "component" used with reference to delivery of a portion of a gas refers to a distinct functional subset of the gas that may, if desired, be delivered separately by the respiratory gas delivered system (and conventionally is delivered separately in the reference respiratory gas delivery system), for example over a different time frame e.g. in sequence with another component as in a sequential gas delivery (SGD) circuit, whereas a "constituent" of the gas is considered by definition already part of a blend of gases of different chemical composition (even in the reference system) that can no longer be delivered separately unless first separated. Typically, constituents include individual or blended gases stored in a tanks for use in conjunction with a gas delivery apparatus in the form a gas blender for example as disclosed, in WO/2007/012197, for example to target an end tidal concentration of a gas X which is present alone or in a blend of gases from a particular tank or source (preferably stored or deliverable under pressure). An end tidal concentration of gas X may be controlled by methods well known to those skilled in the art including the method disclosed in WO/2007/012197 and Slessarev M. et al., J Physiol 581.3 (2007) p. 1207. A constituent gas is therefore considered indivisible without forced separation of its component parts. For example, to deliver a gas composition that targets a partial pressure of carbon dioxide of 50 mm. Hg a gas composition that empirically causes an increase in the partial pressure of CO2 to the desired partial pressure e.g. 8% $CO_2$ and the algorithm disclosed in WO/2007/012197 can be used to maintain this partial pressure.

The term "mathematical model" is used broadly to refer to any model in which any form of a mathematical relationship or computation underlies or is involved in a process executed by a computer and for greater certainty includes a model embodied in a look up table.

The term "algorithm" or related terms such as "algorithmic" (e.g. algorithmic model") refers to any process or set of rules to be followed by a computer in performing a function of the computer, in particular, simulation of one or more components of a reference breathing circuit.

As used in this Section B, in the context of simulating structural features of a reference breathing circuit, and in particular, a sequential gas delivery circuit, simulation could not be carried without at least one if not both of a "mathematical model" and an "algorithmic model" and each may be understood to encompass the other.

As used herein the term "specifiable" implies that a convenient input means is available to a user to specify a parameter or value whereas the term "specified" implies that some parameter or value is set, regardless of whether it is pre-set or obtained by such convenient input. Hence unless used in the phrase "specifiable or specified" the term "specified" does not imply that a value or parameter was not specifiable. The phrase "specifiable or specified" is used herein for convenience to imply that the facility for user input either is or is not readily available without commenting on whether a facility to make a parameter or value "specifiable" is necessary. The convenience of having the facility of a specifiable input can generally be understood to be optional and generally preferred (for potential non-immediate or anticipated or unanticipated future uses, or testing) regardless of whether this facility is needed for using the invention to the most advantageous or most practical extent of its capability, redundant or of no foreseen value provided that the invention can be used only for very narrow purposes or to only modest advantage without this facility.

The term "gas delivery apparatus" as used throughout the specification is any apparatus that is capable of modulating the composition of an inspiratory gas, for example any device that can make a gas of variable/selectable composition available for inspiration.

The gas delivery apparatus may be used in conjunction with a ventilator or any other respiratory assistance device associated with a breathing circuit from which the subject is able to inspire a gas of variable/controllable composition.

Preferably, the composition of the gas and/or flow rate is under computer control. For example, a gas delivery apparatus may be adapted to deliver at least one gas (pure or pre-blended) at a suitable pre-defined rate of flow. The rate of flow may be selectable using a form of input device such a dial, lever, mouse, key board, touch pad or touch screen. Preferably the gas delivery apparatus provides for one or more pure or blended gases to be combined i.e. "a gas blender".

A "gas blender" means a device that combines one or more stored (optionally stored under pressure or delivered by a pump) gases in a pre-defined or selectable proportion for delivery a selectable rate of flow, preferably under computer control. For example one or more stored gases may be combined with pumped room air or a combination of pure or blended (each blended gas may have at least 10% oxygen for safety) gases respectively contain one of carbon dioxide, oxygen and nitrogen as the sole or predominant component. Optionally, the selectable proportion is controlled automatically using an input device, optionally by variably controlling the flow of each stored gas (pure or pre-blended) separately, preferably using rapid flow controllers, to enable various concentrations or partial pressures of a gas X to be selected at will within a pre-defined narrow or broad range. For example, the gas blender may be a high flow blender which blows gas past the mouth (i.e. in which gas that is not inspired is vented to the room) or the gas blender may be adapted to conserve gas by delivering gas in volumes that closely match the patient's volume requirements of a breath.

Optionally, the respiratory gas delivery apparatus contains the basic structural or specialized algorithmic features described in WO/2012/139204.

The term "reached" when used to describe reaching a threshold volume means attained or exceeded.

The term "criterion" means any state or condition for which input needed to determine whether or not the condition is satisfied or the state is present is usable by a processor operatively associated with a respiratory gas delivery system of the invention, optionally input from a measurement device of any kind (e.g. pressure, flow, concentration) that is operatively associated with the respiratory gas delivery system, optionally a measurement device operatively associated a breathing circuit within or proximal to a patient airway interface.

A "rebreathing circuit" or "partial rebreathing circuit" is any breathing circuit in which a subject's gas requirements for an inspiratory cycle are made up in part by a first gas of a selectable composition and a rebreathed gas to the extent that the first gas does not fully satisfy the subject's volume gas requirements for the breath. The first gas must be selectable in at least one of composition or amount. Preferably the amount and composition of the first gas is selectable. The rebreathed gas composition optionally consists of previously exhaled gas that has been stored or a gas formulated to have the same concentration of gas X as previously exhaled gas or a second gas has a gas X concentration that is selected to correspond (i.e. has the same concentration) to that of the targeted end tidal gas composition for a respective breath [i]. Aspects of invention related to the sequential delivery of such components may not apply where the subject's requirements for a breath are over-estimated or where it otherwise not necessary that the entirety of the first gas component make it the alveolar portion of the lung.

Preferably the circuit is designed or employable so that the subject receives the entirety of or a known amount of the first gas in every breath or in a consecutive series of breaths forming part of gas delivery regimen. In a general sense a re-breathed gas serves a key role in that it does not contribute significantly to the partial pressure gradient for gas flow between the lung and the pulmonary circulation when intake of the gas at least fills the entirety of the anatomic dead space. Therefore, in the case of a spontaneously breathing subject (whose tidal volume is not controlled e.g. via a ventilator) the subject's unpredictable tidal volume does not defeat prospective computation of the controlled gas composition required to attain or target an end tidal partial pressure of a gas x (PetX[i]) for a respective breath [i].

Optionally, the "rebreathed gas" may be constituted by or substituted by a prepared gas (in terms of its gas X content). Thus, according to one embodiment of the invention, the second gas has a gas X concentration that is selected to correspond to that of the targeted end tidal gas composition for a respective breath [i]. The volume of the first inspired gas may also be adjusted (e.g. reduced) to target PetX[i]T for a respective breath [i] such that the subject receives an optimal amount of a gas having a gas X concentration that corresponds to a target PetX[i]T. Target end tidal concentrations of gas x may be achieved with a device called a Respiract™ (see WO/2007/012197).

As alluded to above, it will be appreciated that the gas X content of a prepared gas can be formulated to represent a gas of a "neutral" composition. Thus the total inspired gas for a respective breath [i] will comprise a first inspired gas having a controlled volume and gas X concentration (FIX) and a second gas which has a gas X content whose contribution to establishing a partial pressure gradient between the lung and pulmonary circulation is optionally minimized. In a broader sense, the second inspired gas content of gas X can be optimized to attain a targeted end tidal concentration (for a universal set of circumstances) and in a sub-optimal sense this concentration at least does not defeat the ability to prospectively compute an FIX for the purposes of attaining or targeting a PetX[i] for a respective breath [i] (i.e. not knowing the subject's tidal volume for a respective breath [i] will not preclude such computation).

The term "sequential gas delivery circuit" means a breathing circuit in which a first gas, optionally of selectable first composition (e.g. using a gas blender) is delivered first, and a second gas of second composition is delivered later than, optionally after delivery of the first gas, optionally when the first gas is depleted. A sequential gas delivery circuit optionally comprises first and second gas reservoirs and optionally a flow control system (e.g. a valve or series of valves and conduits) for switching repeatedly, optionally in each inspiration cycle, between a first circuit flow path in which the first gas reservoir is drawn upon and a second circuit flow path in which the second gas reservoir is drawn upon. Optionally, the trigger for switching between first and second flow paths is circuit pressure, for example the trigger is generated by an increase in circuit negative pressure when the first gas reservoir is depleted (opening a passive valve leading to second circuit flow path) or for example, a pressure transducer serves as input to alternatively open and close the first and second flow paths. The elapse of time, a gas analyzer reading etc. may also be a trigger.

Figure 10:
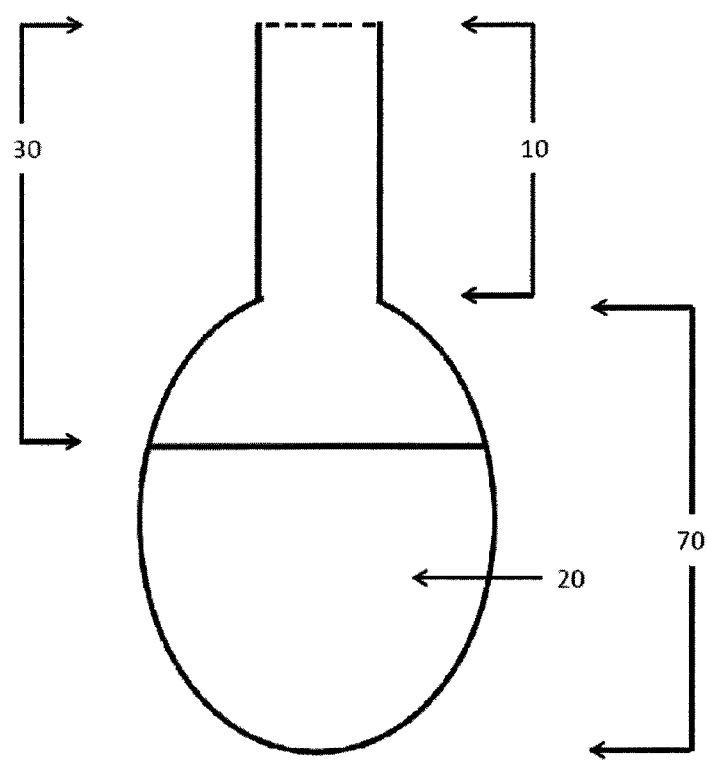
FIGS. 10-14 relate to features of the invention described above that are particularly related to a system for virtual gas delivery, and in particular, a virtual sequential gas delivery (VSGD) system. Immediately below, in the figure descriptions, and in the related description under the heading "Virtual Sequential Gas Delivery" reference to the invention is to virtual gas delivery and reference numerals appearing in FIGS. 10-14 are tied only to the description under this heading.

As seen in FIG. 10, the gas entering the lung may be schematically divided into the alveolar portion 70 which contributes to gas exchange with the pulmonary circulation and the anatomical dead space portion 10, which includes the trachea, bronchi, and bronchioles, namely portions of the lung which carry gas to and from the alveoli, but do not directly contribute to gas exchange. According to one example of a reference breathing circuit, a sequential gas delivery circuit, best seen in FIG. 12, by setting the rate of flow of gas into an inspiratory reservoir to be less than the minute ventilation, optionally less than the minute ventilation minus anatomical dead space ventilation. Gas sourced from a freshly filled inspiratory gas reservoir, when delivered first, occupies a portion of alveolar space 20 which therefore defines the effective alveolar ventilation, since the remainder of the gas making up the subject's inspiratory requirements 30 may be a second delivered gas which is an end tidal gas or a gas of the same approximate composition, which is "neutral" from the standpoint of gas exchange (i.e. it is already equilibrated with the partial pressure of those gases in the pulmonary circulation).

Accordingly, during any inspiration, the gas that is inspired first reaches the alveoli, while the gas inspired towards the end of the inspiratory cycle remains in the anatomical dead space. Many gases administered in clinical or research situations must enter the blood through the alveoli to exert the intended physiological effect. Inhalational anaesthetics such as nitrous oxide or isoflurane are a common example. The portion of such a gas that remains in the anatomical dead space does not enter the blood and do not produce any physiological effect. This portion of the gas is therefore wasted. It would be advantageous to deliver these gases only during the first part of inspiration that enters the alveoli.

This invention can accomplish this by signalling the gas delivery device to provide the gas of interest for a first defined volume of every inspiration, and then turning off delivery of the gas of interest only (setting its concentration in the inspired gas mixture to zero) in any volume inspired beyond the first volume.

Figure 11:
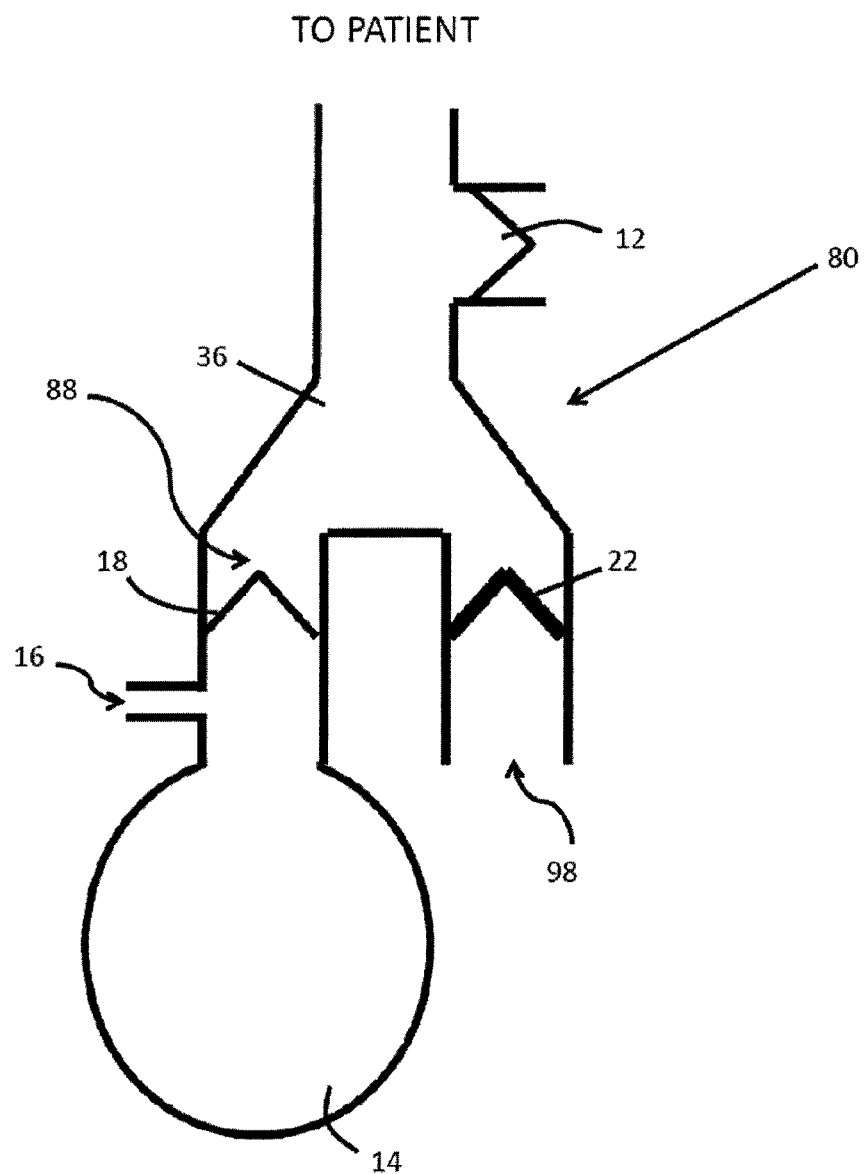
Figure 12:
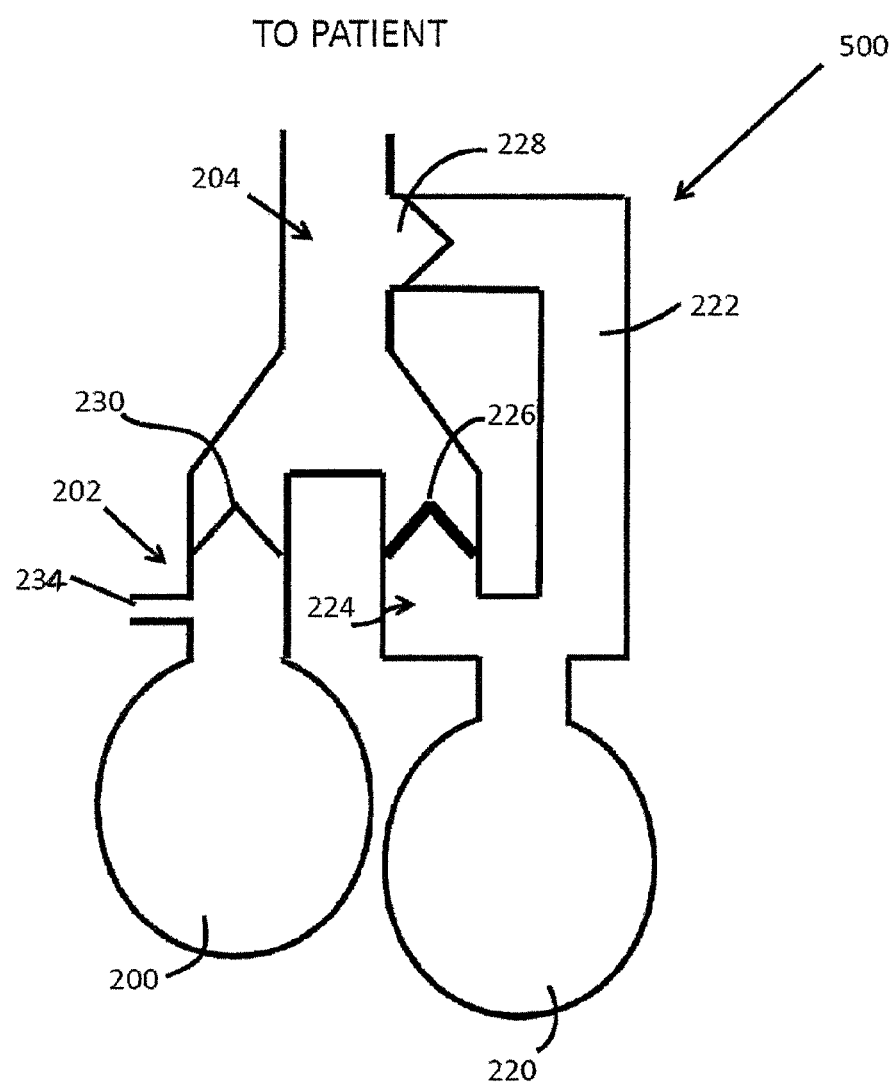

In one aspect the invention, is directed to a gas delivery apparatus programmed to modulate the composition of the inspiratory gas throughout the inspiratory phase of the breath. The composition of the inspiratory gas may optionally be changed according to the cumulative volume of gas inspired. The invention may be used to provide inspiratory gases to a subject, which are equivalent to those that would have been inspired through a particular physical breathing circuit, for example as illustrated in FIGS. 11 and 12. Alternatively, the invention simulates a breathing circuit for which there is no practical physical embodiment. It will be appreciated that certain features of a reference breathing circuit that would be impractical to construct owing to technical challenges (for example, an SGD manifold that is small enough not to be obstructive, flexible gas tubing which does not expand under pressure etc.) may be able to be sufficiently "simulated" by the respiratory gas delivery system of the invention to obviate or minimize such technical challenges. Hence, the terms "respiratory gas delivery system" and "first breathing circuit" encompass virtual systems and circuits which are limited only by the physical limitations of any necessary components selected from at least one of flow sensors, gas analyzers, gas delivery devices (e.g. valves) and flow controllers (e.g. response time, volumetric capability, sensitivity and precision) associated with implementing gas blending and delivery into a simple conduit connected to a patient airway interface.

Similarly the term "simulated" broadly refers to any algorithm which models a practical or "only theoretically" feasible system/circuit, which system/circuit is susceptible of algorithmic modelling, graphical representation and/or mathematical definition to implement a physical system which uses the simulation algorithm as input. For greater certainty, it is to be understood that while at least one component of the reference system of interest (including at least one component of the reference breathing circuit) is being simulated, inputs to the simulation algorithm (e.g. inspiratory flow) may be obtained from a real (i.e. not simulated) system (e.g. a flow sensor connected to a real patient) and the outputs from the simulation algorithm directed to a real (i.e. not simulated) system (e.g. a gas delivery apparatus which may then deliver gas to a real subject). Accordingly, the at least one component of the breathing is circuit may "simulated" in order to replace at least one component of an otherwise embodied ("real") system usable for therapeutic and/or diagnostic or experimental gas delivery, not to be confused with an in silico system that resides solely on a computer for teaching, training or other modelling purposes. In the result, a breathing circuit may be "simulated" at least in part in order to provide the same physical function as that provided by, or postulated for, a reference circuit, for example, using a mathematical function (equation) or a look-up table such that real physical measurements may be obtained and used to calculate and then control a matching output of gas from a gas controller.

The term "matches" and related terms and "tracks" and related terms (implying an equivalent amount or rate) imply a substantial identity which is substantially functionally equivalent qualitatively and quantitatively (subject to only optional correction or avoidance of inferior or inconsequential features).

The subject breathes from gas delivered by a gas delivery apparatus. According to one embodiment, the invention contemplates that a flow sensor is positioned proximal to the subject's airway to measure the flow of inspired gas. The apparatus also comprises a computer in the form of a microprocessor or other computing means. The microprocessor reads the output of the flow sensor. The flow signal may be integrated to compute inspired volume. The microprocessor signals the gas delivery apparatus to deliver specific compositions of inspired gas based on the cumulative inspired volume.

For example, according to one embodiment, illustrated in FIG. 11, the function of the reference Hi-Ox 80 circuit may be approximated by this respiratory gas delivery system according to the present invention. As seen in FIG. 11, one example of a reference breathing circuit is a sequential gas delivery circuit 80 including an inspiratory limb of the circuit 88 comprising a first gas inlet 16 that fills a gas reservoir 14 in the form of an inspiratory gas reservoir. A one-way inspiratory valve 18 enables, for example, a spontaneously breathing subject, to draw on gas in the inspiratory gas reservoir 14 so that gas enters a bifurcated portion of the circuit 36 (optionally a y-piece) to the patient. The patient exhales through one-way expiratory valve 12. When the inspiratory gas reservoir 14 is depleted, valve 22, which opens at a higher pressure than one-way valve 18, responds to the increase in negative pressure, enabling a subject to draw fresh air from the ambient air port 98 for the remainder of that inspiration.

Figure 13:
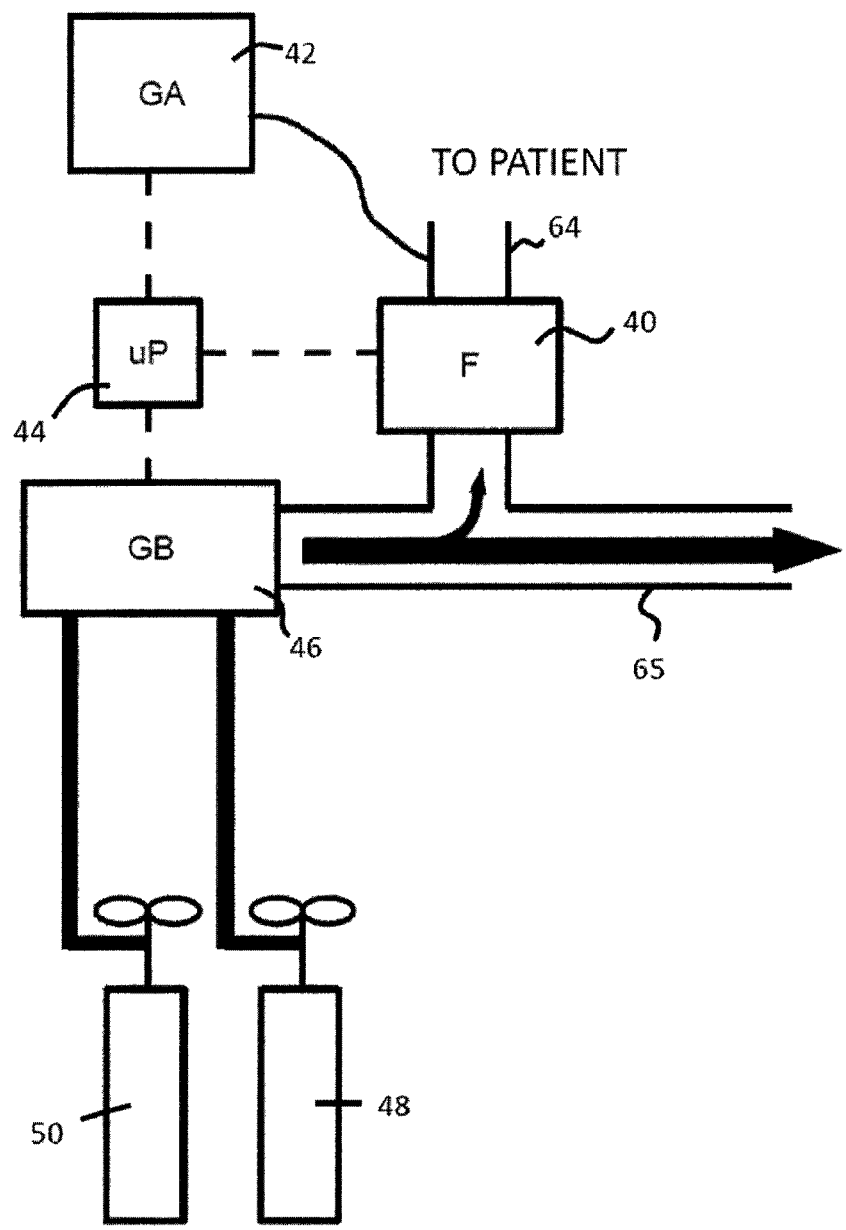

As seen in FIG. 13, according to one embodiment of a respiratory gas delivery system according to the invention, a reference breathing circuit is virtualized using a gas blender 46 to control gas delivery characteristics (at least one of flow rate and composition) of the gas flowing through conduit 65. Gas inspired by the patient is drawn from the stream flowing though conduit 65 via conduit 64. The flow rate though conduit 65 is greater than the maximum inspiratory flow of the patient. The flow sensor 40 associated with conduit 64 determines the volume of gas inspired by the patient. One or more gas analyzers 42 may be used to analyze gas in conduit 64. For example gas exhaled by the patient may be analyzed in conduit 64, for example, depending on the gas of interest, via an NO2 analyzer and/or a CO2 analyzer. Gas blender 46 blends gas from two pressurized sources 50 and 48 and is controlled by microprocessor 44 which receives input from the gas analyzer 42 and flow sensor 40. The microprocessor signals the gas delivery apparatus to provide oxygen for a first predefined volume of any inspiration, and air for any volume inspired beyond the first volume.

This is an only approximation of the Hi-Ox 80 since the volume of high oxygen gas inspired during the first part of the inspiratory cycle is fixed, while with the Hi-Ox 80 it is dependent on the volume accumulated in the reservoir.

Alternatively, the function of the Hi-Ox 80 may be more exactly simulated by the device by accounting for the filling of the reservoir. Here, the microprocessor can be programmed to calculate the volume of oxygen that would be in the reservoir of a Hi-Ox 80, and switch the composition of the inspired gas to air when the calculated volume in the virtual reservoir is zero. In this embodiment, the operator programs the microprocessor with a virtual rate at which the virtual reservoir is to fill. The microprocessor continually increases the volume in the virtual reservoir at the specified virtual flow rate throughout the entire breath. For the first part of any inspiration, the microprocessor signals the gas delivery device to deliver oxygen to the subject. While the subject inspires oxygen, the volume in the virtual reservoir is decreased at the inspiratory flow rate measured by the flow sensor. When the virtual reservoir is empty, the microprocessor signals the gas delivery device to deliver air for the remainder of the current inspiration. While the subject inspires air, the volume of the virtual reservoir is not decreased at the inspiratory flow rate. In this way, the invention allows a subject to inspire the exact same gases as with a physical Hi-Ox 80 circuit with an oxygen reservoir that is being filled at a constant flow rate.

Figure 14:
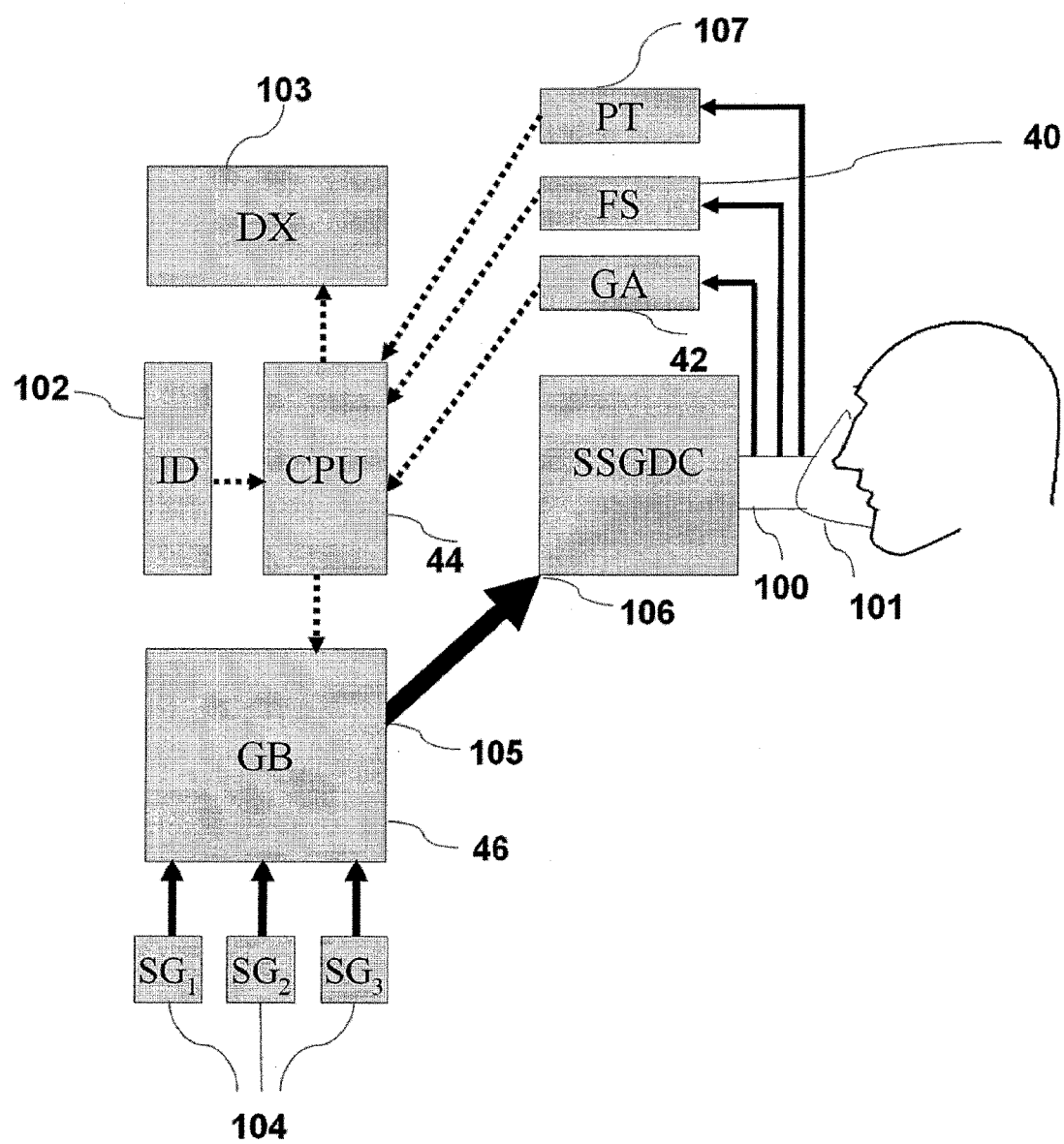

As shown in FIG. 14, according to one embodiment of a respiratory gas delivery system according to the invention, the gas delivery apparatus consists of a gas blender (GB) 46, a simulated sequential gas delivery circuit (SSGDC) 200 optionally comprising a gas conduit 100 and a patient airway interface optionally in the form of mask 101 (alternatives include an endotracheal tube), one or more gas analyzers (GA), a flow sensor (FS) 40, a computer (CPU) 44 (optionally a microprocessor), an input device (ID) 102, and a display (DX) 103. The gas blender 46 optionally contains three rapid flow controllers (not shown) which are capable of delivering accurate mixes of three source gases 104 (SG1, SG2, SG3) to the circuit 200. The gases are delivered to the circuit via a gas delivery tube connecting the outlet of the gas blender 105 to the inlet 106 of the simulated sequential gas delivery circuit 200 which comprises or consists of a gas conduit 100 operatively connected to the flow sensor 40, gas analyzer(s) 42 and patient airway interface. The gas analyzer(s) 42 measures the partial pressures of gases at the airway throughout the breath. The analyzer(s) samples gas for analysis proximal to the subject's airway via a sampling catheter (not shown). A small pump (not shown) is used to draw gases from the subject's airway through the gas analyzers. Optionally, a pressure transducer 107 is used for measurement of the breath period (BP) and end-tidal detection, and also connected by a sampling catheter proximal to the subject's airway. The gas analyzers 42, flow sensor 40 and pressure transducer 107 communicate with the computer 44 via analog or digital electrical signals. The computer 44 optionally runs a software implementation of a simulation algorithm and demands the required mixtures from the blender via analog or digital electrical signals. The operator optionally enters reference breathing circuit parameters, for example the composition and flow rate into an inspiratory gas reservoir of a simulated reference SGD circuit 200 and any subject parameters. The display 103 optionally displays data/fields for inputs and outputs with respect to fixed or alterable input parameters and fixed or variable output parameters.

The respiratory gas delivery system according to the invention may be directed to supplant, in whole or part, a reference breathing circuit in the form of an SGD circuit 500 similar to the Hi-Ox 80. As seen in FIG. 12, an inspiratory limb at the 202 reference circuit 500 comprises a first gas inlet 234. Inlet 234 fills a gas reservoir 200 in the form of an inspiratory gas reservoir. A one way inspiratory valve 230 enables, for example a spontaneously breathing subject, to draw on gas in the inspiratory gas reservoir 200, so that gas enters a bifurcated portion of the circuit (optionally a y-piece) leading to the patient. The patient exhales through one-way expiratory valve 228. When the inspiratory gas reservoir 200 is depleted, valve 226 which opens at a higher pressure than one-way valve 230 responds to the increase in negative pressure, enabling a subject to draw on a second expiratory gas reservoir 220. The subject's expired air is collected in the second reservoir 220 and the inlet side 224 of the valve 226 is connected to reservoir 220. Therefore, this circuit is similar to the Hi-Ox 80 except that upon depletion of the first gas reservoir 200, the subject draws the remainder of the inspiratory cycle from the reservoir 220 containing previously expired gas as opposed to air.

This circuit may be simulated by the invention in the same way as the Hi-Ox 80 except that upon depletion of the virtual reservoir, instead of air, the microprocessor signals the gas delivery device to deliver gas with a fractional concentration of at least one gas e.g. oxygen and carbon dioxide equal to that in the gas expired in the previous breath. Optionally, the oxygen content of the gas expired in the previous breath is analyzed with an oxygen analyzer and carbon dioxide analyzer whose output is read by a microprocessor.

According to one embodiment, a virtual circuit simulates any breathing circuit, or part thereof, which operates to vary the composition and/or pattern of flow of the gas inspired by the subject by:
1. Developing a mathematical or algorithmic formulation of the behavior of the circuit, and
in real-time:
2. Obtaining the inputs required to use the mathematical or algorithmic formulation to compute the composition and/or pattern of flow of the gas that would be delivered by the circuit
3. Compute the composition and/or pattern of flow of the gas that would be delivered by the circuit using the mathematical or algorithmic formulation
4. Direct an apparatus capable of controlling the composition and/or pattern of flow of inspired gas to deliver gas of a composition and/or pattern of flow equal to that the gas that would be delivered by the circuit as determined using the obtained inputs and mathematical formulation.
For example simulating SGD to vary composition only:
1. Develop mathematical formulation BagVol=BagVol+G1Flow;

If(Insp)
   if(Bag=1)
   BagVol=BagVol−InspFlow;
   If(BagVol==0)
   Bag=2;
   If(Bag=1)
   Composition=G1 Composition
   If(Bag=2)
   Composition=Last PetCO2 or TargetPetCO2

If(Exp)
   Bag=1;
2. Obtain inputs

From the formulation, it is obvious that the required inputs are G1 Flow (input by user), G1 Composition (input by user), Last PetCO2 (CO2 sensor), InspFlow (Flow sensors)
3. Use the algorithm in 1 and the inputs in 2 to compute composition
4. Direct the real-time gas-blender to deliver composition Example: Simulating a ventilator with a mechanical pop-off valve. In this case, the ventilator will deliver some desired insp flow to the subject, and if the airway pressure exceeds the mechanical pop-off, all the delivered flow is vented and subject gets 0 flow. This can easily be simulated with a pressure sensor and control of the blower.
1. Develop mathematical formulation of behavior
if(AirwayPressure<PressureLimit)
   BlowerFlow=Desired Insp Flow
else
   BlowerFlow=0
2. Obtain inputs From the formulation, it is obvious that the required inputs are Desired Insp Flow (ventilator setting), Airway-Pressure (pressure sensor), PressureLimit (input by user=mechanical pop-off limit).
3. Use the algorithm in 1 and the inputs in 2 to compute BlowerFlow
4. Direct the blower to deliver BlowerFlow Theoretically the invention can be applied to any circuit, but preferably the simulated circuit is advantageous in at least one of the following ways: less expensive, more robust, more efficient, etc. (see above) that the original circuit. In the case of SGD, this is certain.

Example 1

In one embodiment the respiratory gas delivery system is programmed to obtain the inputs related to the volume, rate of fill and depletion of an inspiratory reservoir, inspiration v. expiration, concentration of gas in inspiratory reservoir, concentration of gas in expiratory reservoir, which bag is being accessed, outputs including signaling the gas delivery device to turn off during expiration, switch concentrations when the inspiratory reservoir is depleted, switch to inspiratory reservoir concentration when inspiration is over etc. as further exemplified below:

```
// Variables
numeric inspiratory_flow;    // Inspiratory flow in ml/min
numeric g1_bag_volume;       // Volume in the g1 bag in ml
numeric g1_bag_flow;         // Fill rate of the g1 bag in ml/min
numeric last_time;           // Last time the main loop was
                             // executed in ms
numeric delta_t;             // Time elapsed since last execution
                             // of the main loop in ms
numeric desired_conc_x;      // Concentration of gas x to be delivered
                             // to the subject for inspiration
numeric conc_x_g1;           // Concentration of gas x in the g1 bag
numeric conc_x_g2;           // Concentration of gas x in the g2 bag
boolean is_inspiration;      // Indicates inspiration or expiration
                             // Inspiration = true, Expiration = false
boolean is_bag_1;            // Indicates bag being inspired from
                             // Inspiring from g1 bag = true,
                             // otherwise = false
// Main loop
do(forever)
{
    // Determine amount of time that has elapsed in ms
```

```
// get_time( ) is a function that returns time
// with ms resolution
delta_t = get_time( ) - last_time;
last_time = get_time( );
// Determine instantaneous flow in ml/min
// read_inspiratory_flow_sensor( ) returns the
// latest flow measurement in ml/min
inspiratory_flow = read_inspiratory_flow_sensor( );
// Determine bag parameters:
// - Fill rate of g1 bag
// - Concentration of gas x in g1 bag
// - Concentration of gas x in g2 bag
// These parameters may be sent to the device running
// this code by the operator or another device. For example,
// this code may be run on a micro-processor and these
// parameters sent to this micro-processor by a PC.
// The function read_in( ) is assumed to populate the values
// of these parameters.
read_in(g1_bag_flow,conc_x_g1, conc_x_g1);
// Determine if inspiration or expiration:
// Switch to inspiration if currently expiring and
// inspiratory flow exceeds a threshold. Switch
// to expiration if currently inspiring and flow
// drops below a threshold. In this case, the threshold
// is 500 ml/min but could be set depending on the size of
// the subject and the resolution/noise of the flow sensor.
if(is_inspiration = false AND inspiratory_flow > 500 ml/min)
{
    is_inspiration = true;
}
else if(is_inspiration = true AND inspiratory_flow < 500 ml/min)
{
    is_inspiration = false;
}
// Increase the volume in the g1 bag by the gas
// flow that has accumulated since the last time
// the main loop was executed
// 60000 converts ml/min to ml/ms
g1_bag_volume += g1_bag_flow * delta_t * 60000;
// Inspiring from the g1 bag
if(is_inspiration = true AND is_bag_1 = true)
{
    // Decrease the volume in the g1 bag by the
    // gas that has been inspired since the last
    // time the main loop was executed
    // 60000 converts ml/min to ml/ms
    g1_bag_volume -= inspiratory_flow * delta_t * 60000;
    // Signal the gas delivery device to
    // deliver the concentration of gas x
    // in the g1 bag
    desired_conc_x = conc_x_g1;
    // If the g1 bag is empty switch to the g2 bag
    if(g1_bag_volume <= 0)
    {
        bag = 2;
    }
}
// Inspiring from the g2 bag
else if(is_inspiration = true AND is_bag_1 = false)
{
    // Signal the gas delivery device to
    // deliver the concentration of gas x
    // in the g2 bag
    desired_conc_x = conc_x_g2;
}
// Expiration
else
{
    // Signal the gas delivery device to
    // turn off during expiration
    desired_conc_x = 0;
    // When the inspiration is over, switch
    // bag to the g1 bag for the next breath
    is_bag_1 = true;
}
// Signal the gas delivery device to
// deliver the desired concentration
// of gas x:
// set_inspired_concentration_of_gas_x( )
// is a function which accepts the desired
// concentration of gas x, and signals
// the gas delivery device to deliver the
// desired concentration
set_inspired_concentration_of_gas_x(desired_conc_x);
} // End of main loop
```

Section C: Description of Invention

Prospective Model For End Tidal Targeting, Targeting Sequences and Various Applications of End Tidal Targeting Algorithms (hereinafter optionally referred to as the Prospective Model Based Targeting invention of PMBT invention, for ease of reference)

The following description is contained in PCT application no. PCT/CA2013/000427 filed Apr. 30, 2013 (published as WO/2013/163735) which claims priority from U.S. application No. 61/640,570 filed Apr. 30, 2012. This application, the content of which is hereby incorporated by reference, references a prospective model for end tidal targeting, and also particular sequences which are ramp target sequences in contrast to steps up or down in relatively large steps (e.g. jumps up or down in PetX of at least 5 or 10 mm Hg in a particular breath as logistically feasible). Importantly, it will be additionally appreciated that the present invention facilitates use of a negative feedback algorithm to ramp up or down end $PetX^T$ in relatively fine increments.

Techniques for controlling end-tidal partial pressures of carbon dioxide, oxygen and other gases are gaining increasing importance for a variety of research, diagnostic and medicinal purposes. Methods for controlling end tidal pressures of gases have gained particular importance as a means for manipulating arterial levels of carbon dioxide (and also oxygen), for example to provide a controlled vasoactive stimulus to enable the measurement of cerebrovascular reactivity (CVR) e.g. by MRI.

Conventional methods of manipulating arterial carbon dioxide levels such as breath holding, hyperventilation and inhalation of fixed concentration of carbon dioxide balanced with medical air or oxygen are deficient in their ability to rapidly and accurately attain targeted arterial carbon dioxide partial pressures for the purposes of routinely measuring vascular reactivity in a rapid and reliable manner.

The end-tidal partial pressures of gases are determined by the gases inspired into the lungs, the mixed venous partial pressures of gases in the pulmonary circulation, and the exchange of gases between the alveolar space and the blood in transit through the pulmonary capillaries. Changes in the end-tidal partial pressures of gases are reflected in the pulmonary end-capillary partial pressures of gases, which in turn flow into the arterial circulation. The gases in the mixed-venous blood are determined by the arterial inflow of gases to the tissues and the exchange of gases between the tissue stores and the blood, while the blood is in transit through the tissue capillary beds.

Robust control of the end-tidal partial pressures of gases therefore requires precise determination of the gas storage, transport, and exchange dynamics at the lungs and throughout the body. Previous attempts at controlling the end-tidal partial pressures of gases have failed to account for these complex dynamics, and have therefore produced mediocre results.

In the simplest approaches, manipulation of the end-tidal partial pressures of gases has been attempted with fixed changes to the composition of the inspired gas. However, without any additional intervention, the end-tidal partial pressures of gases vary slowly and irregularly as exchange occurs at the lungs and tissues. Furthermore, the ventilatory response to perturbations in the end-tidal partial pressures of gases is generally unpredictable and potentially unstable. Often, the ventilatory response acts to restore the condition of the blood to homeostatic norms. Therefore, any changes in the end-tidal partial pressures of gases are immediately challenged by a disruptive response in the alveolar ventilation. Consequently, fixed changes in the inspired gas composition provoke only slow, irregular, and transient changes in blood gas partial pressures.

In more complex approaches, manipulation of the end-tidal partial pressures of gases has been attempted with negative feedback control. These approaches continuously vary the composition of the inspired gas so as to minimize error between measured and desired end-tidal partial pressures of gases. Technically, such a system suffers from the same limitations as all negative feedback control systems— an inherent trade-off between response time and stability.

Consequently, there is a need to overcome previous limitations in end-tidal gas control, allowing for more precise and rapid execution of end tidal gas targeting sequences in a wide range of subjects and environments.

According to one aspect the instant invention is directed to a method for attaining a target partial pressure of at least one gas X ($PetX^T$) in a spontaneously breathing mammal's (subject's) blood by integrating into a control algorithm a sequential gas delivery algorithm, preferably as hereinabove defined, and a negative feedback control algorithm, for example as more particularly described above. Optionally, a predictive algorithm is also contemporaneously employed to attain a target partial pressure of at least one gas X ($PetX^T$), optionally a predictive algorithm as described with reference to the PMBT invention hereafter.

According to one aspect the PMBT invention is directed to a method of controlling an amount of at least one gas X in a subject's lung to attain at least one targeted end tidal partial pressure of the at least one gas X, comprising the steps of:
  a. Obtaining input of a logistically attainable end tidal partial pressure of gas X ($PetX[i]^T$) for one or more respective breaths [i];
  b. Obtaining input of a prospective computation of an amount of gas X required to be inspired by the subject in an inspired gas to target the $PetX[i]^T$ for a respective breath [i] using inputs required to compute a mass balance equation, wherein one or more values required to control the amount of gas X in a volume of gas delivered to the subject is output from the mass balance equation; and optionally
  c. Controlling the amount gas X in a volume of gas delivered to the subject in a respective breath [i] to target the respective $PetX[i]^T$ based on the prospective computation.

For present purposes a mass balance equation is understood to be a mathematical relationship that applies the law of conservation of mass (i.e. the amount of at least one gas X) to the analysis of movement of at least one gas X, in and out of the lung, for the purpose of prospectively targeting an end tidal partial pressure of gas X. Optionally, where an end tidal partial pressure of gas X is sought to be changed from a baseline steady state value or controlled for a sequence of respective breaths [i] the mass balance equation will account for the transfer of a mass of gas X between a subject's lung and pulmonary circulation (i.e. the mixed venous blood entering the pulmonary capillaries ($C_{MV}X[i]$)); so that this key source of flux affecting the end tidal partial pressure of gas X in the breath(s) of interest, is accounted for.

Preferably the mass balance equation is computed based on a tidal model of the lung as described hereafter.

In one approach, a concentration of gas X ($F_IX$), for example in a first inspired gas (the first inspired gas also referred to, in one embodiment of the PMBT invention, as a controlled gas mixture) is computed to target or attain $PetX[i]^T$ in a respective breath [i].

Optionally, the mass balance equation is solved for $F_IX$.

It will be appreciated that $F_IX$ may be output from the mass balance equation by testing iterations of its value without directly solving for $F_IX$.

Optionally, the volume of gas delivered to the subject is a fixed tidal volume controlled by a ventilator.

Optionally, the volume of gas delivered to the subject in a respective breath [i] comprises a first inspired gas of known volume and a second inspired neutral gas.

In accordance with a tidal model of the lung, in one embodiment of the PMBT invention, the mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i].

According to another aspect, the PMBT invention is directed to a method of controlling an amount of at least one gas X in a subject's lung to attain a targeted end tidal partial pressure of the at least one gas X, comprising the steps of:
  a. Obtaining input of a concentration of gas X in the mixed venous blood entering the subject's pulmonary circulation for gas exchange in one or more respective breaths [i] ($C_{MV}X[i]$);
  b. Obtaining input of a logistically attainable end tidal partial pressure of gas X ($PetX[i]^T$) for a respective breath [i];
  c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and optionally
  d. Controlling the amount gas X in a volume of gas delivered to the subject in a respective breath [i] to target the respective $PetX[i]^T$ based on the prospective computation.

Optionally, a concentration of gas X ($F_IX$) is computed to target or attain $PetX[i]^T$ in a respective breath [i].

Optionally, the mass balance equation is solved for $F_IX$.

According to one embodiment of the method, the mass balance equation is computed based on a tidal model of the lung.

In accordance with a tidal model of the lung, in one embodiment of the invention, the mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i].

According to another embodiment of the method, the method comprises the step of tuning one or more inputs required for computation of $F_IX$, for example, with respect to any terms and/or by any methods described in this application.

According to another embodiment of the method, the volume of inspired gas entering the subject's alveoli is controlled by fixing a tidal volume of an inspired gas containing gas X using a ventilator and subtracting a volume of gas corresponding to an estimated or measured value for the subject's anatomic dead space volume.

According to another embodiment of the method, the gas inspired by the subject is inspired via a sequential gas delivery circuit (as defined below). Optionally, the rate of flow of gas into the sequential gas delivery circuit is used to compute the volume of inspired gas entering the subject's alveoli in a respective breath [i].

Optionally, the gas inspired by the subject in each respective breath [i] comprises a first inspired gas and a second inspired optionally neutral gas, wherein the first inspired gas is delivered in the first part of a respective breath [i] followed by a second inspired neutral gas for the remainder of the respective breath [i], the volume of the first inspired gas selected so that intake of the second inspired neutral gas at least fills the entirety of the anatomic dead space. $F_IX$ is computed prospectively from a mass balance equation expressed in terms which correspond to all or an application-specific subset of the terms in equation 1 and the first inspired gas has a concentration of gas X which corresponds to $F_IX$ for the respective breath [i]

A "tidal model of the lung" means any model of the movement of gases into and out of the lung that acknowledges that inspiration of gas into, and the expiration of gas from the lung, occurs in distinct phases, each inspiration-expiration cycle comprising a discrete breath, and that gases are inspired in to, and expired from, the lungs via the same conduit.

In terms of computing a mass balance equation and capturing relevant aspects of movement of gases into and out of the lung, a tidal model of lung is preferably understood to yield a value of $F_IX$ on a breath by breath basis from a mass balance equation. The mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i]. Optionally, the mass balance equation is solved for $F_IX$.

Preferably for optimal prospective model accuracy in a universal set of circumstances, all these discrete volumes are accounted for in the mass balance equation. However, it is possible for the invention to be exploited sub-optimally or for individual circumstances in which the relative sizes of certain of these respective volumes (e.g. anatomic dead space, volume of gas X transferred between the pulmonary circulation and lung and even tidal volume (shallow breaths) may be relatively small (compared to other volumes) depending on the circumstances and hence failing to account for all of these volumes may affect achievement of a target end tidal partial pressure to an acceptable extent particularly where less accuracy is demanded.

In one embodiment of the PMBT invention, the mass balance equation (optionally written in terms of one or more concentration of gas X in one or more discrete volumes of gas):

a. Preferably accounts for the total amount of gas X in the lung following inhalation of the inspired gas in a respective breath [i] ($M_LX[i]$) including transfer of gas X between the lung and the pulmonary circulation;

b. Assumes distribution of $M_LX[i]$ into compartments including the subject's FRC ($M_LX[i]_{FRC}$), a fixed or spontaneously inspired tidal volume ($M_LX[i]_{VT}$) and preferably the subject's anatomic dead space volume ($M_LX[i]_{VD}$);

c. Assumes uniform distribution of the $M_LX[i]_{FRC}$ a and $M_LX[i]_{VT}$ in the cumulative volume $FRC+V_T$;

d. Preferably includes a term that accounts for re-inspiration in a respective breath [i] of an amount of gas X left in the dead space volume after exhalation in a previous breath [i−1].

As detailed below, according to one embodiment, in which the PMBT invention is implemented via sequential gas delivery, the individual respective tidal volume for a breath [i] may consist of a first inspired gas having a concentration of gas X corresponding to $F_IX$ and second inspired neutral gas. The volume of the first inspired gas may be fixed, for example by controlling the rate of flow of first inspired gas into a sequential gas delivery circuit.

In one embodiment of the PMBT invention the mass balance equation comprises terms corresponding to all or an application-specific subset of the terms in equations 1 or 2 forth below as described hereafter. An "application-specific subset" means a subset tailored to either a minimum, intermediate or logistically optimal standard of accuracy having regard to the medical or diagnostic application of the invention in question or the sequence of $PetX[i]^T$ values targeted. Optional terms and mandatory inclusions in the subset may be considered application-specific as a function of the sequence of $PetX[i]^T$ values targeted in terms of the absolute size of the target value and/or the relative size of the target value going from one breath to the next as discussed below. For example, in most cases, the $O_2$ or $CO_2$ re-inspired from the anatomical dead space ($V_D$) is small compared to the $O_2$ or $CO_2$ in the other volumes that contribute to the end-tidal partial pressures. For example, where the volume of $O_2$ or $CO_2$ in the first inspired gas is very large, in trying to induce a large increase in the target end-tidal partial pressures, the $O_2$ or $CO_2$ transferred into the lung from the circulation may be comparatively small and neglected. Neglecting any terms of the mass balance equations will decrease computational complexity at the expense of the accuracy of the induced end-tidal partial pressures of gases.

The demands of a diagnostic application may be ascertained empirically or from the literature. For example, a measure of short response times of brain blood vessels to hypercapnic stimulus can be determined to require a square wave change in the stimulus such as a change of 10 mmHg $P_{ET}CO_2$ from one breath to the next. Another example is when measuring response of BOLD signal with MRI to changes in partial pressure of $CO_2$ in the blood, the changes needed may be determined to be abrupt as the BOLD signal has considerable random drift over time.

Optionally, one or more inputs for computation of $PetX[i]^T$ are "tuned" as defined below to adjust, as necessary or desirable, estimated or measured values for FRC and/or total metabolic production/consumption of gas X so as to reduce the discrepancy between targeted and measured end tidal partial pressures of gas X i.e. an actual value, optionally measured at the mouth. Tuning can be done when a measured baseline steady state value of $PetX[i]$ is defined for a series of test breaths.

According to another aspect, the PMBT invention is directed to an apparatus for controlling an amount of at least one gas X in a subject's lung to attain a targeted end tidal partial pressure of the at least one gas X, comprising:

(1) a gas delivery device;
(2) a control system for controlling the gas delivery device including means for:
  a. Obtaining input of a concentration of gas X in the mixed venous blood entering the subject's pulmonary circulation for gas exchange in one or more respective breaths [i] ($C_{MV}X[i]$);
  b. Obtaining input of a logistically attainable end tidal partial pressure of gas X ($PetX[i]^T$) for a respective breath [i];
  c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
  d. Controlling the amount of gas X in a volume of gas delivered to the subject in a respective breath [i] to target the respective $PetX[i]^T$ solely based on the prospective computation.

In one embodiment of the method, a concentration of gas X ($F_IX$) is computed to target or attain $PetX[i]^T$ in a respective breath [i].

Optionally, the mass balance equation is solved for $F_IX$.

It will be appreciated the control system may implement one or more embodiments of the method described in this section C.

In one embodiment of such an apparatus the gas delivery device is a sequential gas delivery device.

In one embodiment of the apparatus, the control system is implemented by a computer.

In one embodiment of the apparatus, the computer provides output signals to one or more rapid flow controllers.

In one embodiment of the apparatus, the apparatus is connected to a sequential gas delivery circuit.

In one embodiment of the apparatus, the computer receives input from a gas analyzer and an input device adapted for providing input of one or more logistically attainable target end tidal partial pressure of gas X ($PetX[i]^T$) for a series of respective breaths [i].

In one embodiment of the apparatus, the control system, in each respective breath [i], controls the delivery of at least a first inspired gas and wherein delivery of the first inspired gas is coordinated with delivery a second inspired neutral gas, wherein a selected volume of the first inspired gas is delivered in the first part of a respective breath [i] followed by the second inspired neutral gas for the remainder of the respective breath [i], wherein volume of the first inspired gas is fixed or selected for one or more sequential breaths by way of user input so that intake of the second inspired neutral gas at least fill the entirety of the anatomic dead space.

In one embodiment of the apparatus, the apparatus is connected to a sequential gas delivery circuit.

In one embodiment of the apparatus, the gas delivery device is a gas blender.

In one embodiment of the apparatus, the control system implements program code stored in a computer readable memory or comprises a signal processor embodied in one or more programmable IC chips.

A prospective model may be embodied in a computer program product for use in conjunction with a gas delivery device to control an amount of at least one gas X in a subject's lung to attain a target end tidal partial pressure of a gas X in the subject's lung, comprising program code for:
  a. Obtaining input of a concentration of gas X in the mixed venous blood entering the subject's pulmonary circulation for gas exchange in one or more respective breaths [i] ($C_{MV}X[i]$);
  b. Obtaining input of a logistically attainable end tidal partial pressure of gas X ($PetX[i]^T$) for a respective breath [i];
  c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
  d. Controlling the amount in a volume of gas delivered to the subject in a respective breath [i] to target the respective $PetX[i]^T$ based on the prospective computation.

In one embodiment of the method, a concentration of gas X ($F_IX$) is computed to target or attain $PetX[i]^T$ in a respective breath [i].

Optionally, the mass balance equation is solved for $F_IX$.

It will be appreciated the computer program product may be used in conjunction with a gas delivery device, to at least partially implement a control system for carrying out one or more embodiments of the method described herein.

The program code may be stored in a computer readable memory or embodied in one or more programmable IC chips.

The present invention is also directed to the use of an aforementioned method, apparatus or computer program product to:
  a) Provide a controlled vasoactive stimulus for measurement of vascular reactivity;
  b) Provide a controlled vasoactive stimulus for measurement of cerebrovascular reactivity;
  c) Provide a controlled vasoactive stimulus for measurement of liver, kidney, heart or eye vascular reactivity; or
  d) Simultaneously change the subject's end tidal partial pressures of oxygen and carbon dioxide to selected values, for example to potentiate a diagnosis or treat cancer.

According to another aspect, the present invention is directed to a method of controlling an amount of at least one gas X in a subject's lung to attain a targeted end tidal partial pressure of the at least one gas X, comprising the steps of:
  a. Obtaining input of a concentration of gas X in the mixed venous blood entering the subject's pulmonary circulation for gas exchange in one or more respective breaths [i] ($C_{MV}X[i]$);
  b. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation, the mass balance equation comprising terms corresponding to all or an application-specific subset of the terms set forth in:

$$F_I X[i] = \frac{\begin{array}{c}(P_{ET}X[i]^T - P_{ET}X[i-T]^T) \cdot \\ (FRC + V_T) + P_{ET}X[i-1]^T \cdot \\ (FG_1 \cdot T_B) - PB \cdot Q \cdot (1-s) \cdot T_B \cdot \\ (C_{MV}X[i] - C_P X[i])\end{array}}{FG_1 \cdot T_B \cdot PB} \quad \text{eq. 1}$$

$$F_I X[i] = \frac{\begin{array}{c}P_{ET}X[i]^T \cdot (FRC + V_T) - \\ P_{ET}X[i-1]^T \cdot (FRC + V_D) - \\ PB \cdot Q \cdot (1-s) \cdot T_B \cdot \\ (C_{MV}X[i] - C_P X[i])\end{array}}{(V_T - V_D) \cdot PB} \quad \text{eq. 2}$$

c. Controlling the amount of gas X in a volume of gas delivered to the subject in a respective breath [i] to target the respective PetX[i]$^T$ based on the prospective computation.

The terms referred to the equations are defined herein.

In one embodiment of the method, a concentration of gas X ($F_I X$) is computed to target or attain PetX[i]$^T$ in a respective breath [i].

Optionally, the mass balance equation is solved for $F_I X$.

According to one embodiment, the gas inspired by the subject in each respective breath [i] comprises a first inspired gas and a second inspired neutral gas (as define hereafter), wherein a selected volume of the first inspired gas is delivered in the first part of a respective breath [i] followed by a second inspired neutral gas for the remainder of the respective breath [i], the volume of the first inspired gas selected so that intake of the second inspired neutral gas at least fills the entirety of the anatomic dead space.

The verb "target" used with reference to achieving a logistically attainable PetX[i]$^T$ value for a respective breath [i] means "attain" with the relative precision pragmatically demanded by the particular therapeutic or diagnostic application in question or the sequence of targets sought to be attained in both absolute and relative (between contiguous breaths) terms. For example, as discussed below, by "tuning" values for certain inputs into equation 1 or 2 (particularly functional residual capacity and total metabolic consumption or production of gas X) a logistically attainable end tidal partial pressure of gas X could be attained with relative precision in one breath. The logistically attainable PetX[i]$^T$ value could theoretically be attained with a clinically acceptable reduced precision by not tuning those values or foregoing other optimizations, as described herein, for example, by tuning total metabolic production or consumption of gas X without tuning FRC, which would be expected to delay getting to the target value more precisely by several breaths.

For purposes herein, it is understood that limitations of a physiological or other nature may impinge on attaining a PetX[i]$^T$. Given a logistically attainable target for which parameters known to impinge on accuracy, that can be optimized (described herein e.g. tuning FRC and total metabolic consumption/production of gas X) are optimized, we have found that a PetX[i]$^T$ can be considered to be "attained" as a function of the difference between the targeted value and a steady state value measured for an individual. For example, assuming a measurement error of +/−2 mm. of Hg, in the case of $CO_2$, for a PetX[i]$^T$ between 30 and 50 mmHg, a measured PetCO$_2$ value that is within 1 to 3 mm. of Hg of PetX[i]$^T$ can be considered to be "attained". Tuning to an extent that achieves a measured value within this range will serve as an indicator as to whether tuning has been successfully completed or should be continued. However in principle, tuning may be iterated until the difference between the measured and targeted PetX is minimized. However, for a PetCO$_2$[i]$^T$ between 51 and 65 mmHg, a measured PetX value that is within (i.e +/−) 1 to 5 mm. of Hg of PetCO$_2$[i]$^T$ can be considered to be "attained" and the success of a given tuning sequence can be judged accordingly.

In the case of oxygen, a measured PetO$_2$ value that is within 5-10% of PetO$_2$[i]$^T$ can be considered to be one which has "attained" PetO$_2$[i]$^T$. For example, if the target PetO$_2$ value is between 75 mm of Hg and 150 mm of Hg a range of measured values that proportionately is within (i.e. +/−) 4 mm and 8 mm of Hg (5 and 10% of 75 respectively) to +/−8 mm to 15 mm of Hg (5-10% of 150) can be considered to be attained (similarly for a target of 100 mm of Hg, +/−5-10 mm of Hg; and for a PetO2[i]$^T$ of 200 mm Hg, +/−10-20 mm of Hg).

However, as described above, depending on the demands of the application and the circumstances, a PetX[i]$^T$ can be considered to be "targeted" with a deliberately reduced precision (as opposed to "attained" as a goal) if parameters known to impinge on accuracy, that can be optimized (described herein e.g. tuning FRC and total metabolic consumption/production of gas X) are deliberately not optimized. The invention as defined herein (not to the exclusion of variations apparent to those skilled in the art) is nevertheless exploited inasmuch as various aspects of the invention described herein provide for a prospective targeting system, a system that can be judiciously optimized (or not) to accommodate a variety of circumstances and sub-optimal uses thereof. A PetX[i]$^T$ can be considered to have been "targeted" by exploiting the invention as defined, in one embodiment, after executing a sequence of tuning breaths, wherein the tuning sequence optionally establishes that the optimizations defined herein make the target "attainable".

According to another aspect, the present invention is also directed to a preparatory method for using a gas delivery device to control an amount of at least one gas X in a subject's lung to attain a targeted end tidal partial pressure of the at least one gas X, comprising the step of executing a sequence of "tuning" breaths as described hereafter.

Optionally, one or more inputs for computation of PetX [i]$^T$ are "tuned" as defined below to adjust, as necessary or desirable, estimated or measured values for FRC and/or total metabolic production/consumption of gas X so as to reduce the discrepancy between targeted and measured end tidal partial pressure of gas X i.e. an actual value, optionally measured at the mouth. Tuning is preferably done when a measured baseline steady state value of PetX[i] is ascertained for a series of ensuing test breaths.

According to one embodiment of the invention, an estimated or measured value for the subject's functional residual capacity (FRC) is tuned.

Optionally, FRC is tuned in a series of tuning breaths by:
a. changing the targeted end tidal partial pressure of gas X between a tuning breath [i+x] and a previous tuning breath [i+x−1];
b. comparing the magnitude of the difference between the targeted end tidal partial pressure of gas X for said tuning breaths [i+x] and [i+x−1] with the magnitude of the difference between the measured end tidal partial pressure of gas X for the same tuning breaths to quantify any discrepancy in relative magnitude; and
c. adjusting the value of FRC in proportion to the discrepancy to reduce the discrepancy in any subsequent prospective computation of $F_I X$.

Optionally, FRC is tuned in a series of tuning breaths in which a sequence of end tidal partial pressures of gas X is targeted at least once by:

(a) obtaining input of a measured baseline steady state value for PetX[i] for computing $F_IX$ at start of a sequence;

(b) selecting a target end tidal partial pressure of gas X (PetX[i]$^T$) for at least one tuning breath [i+x] wherein PetX[i+x]$^T$ differs from PetX[i+x−1]$^T$; and (c) comparing the magnitude of the difference between the targeted end tidal partial pressure of gas X for said tuning breaths [i+x] and [i+x−1] with the magnitude of the difference between the measured end tidal partial pressure of gas X for the same tuning breaths to quantify any discrepancy in relative magnitude;

(d) adjusting the value of FRC in proportion to any discrepancy in magnitude to reduce the discrepancy in a subsequent prospective computation of $F_IX$ including in any subsequent corresponding tuning breaths [i+x−1] and [i+x] forming part of an iteration of the sequence.

According to one embodiment of the invention, an estimated or measured value of the subject's total metabolic production or consumption of gas X is tuned.

Optionally, the total metabolic production or consumption of gas X is tuned in a series of tuning breaths by comparing a targeted end tidal partial pressure of gas X (PetX[i+x]$^T$) for the at least one tuning breath [i+x] with a corresponding measured end tidal partial pressure of gas X for the corresponding breath [i+x] to quantify any discrepancy and adjusting the value of the total metabolic production or consumption of gas X in proportion to any discrepancy to reduce the discrepancy in any subsequent prospective computation of $F_IX$.

Optionally, the total metabolic consumption or production of gas X is tuned in a series of tuning breaths in which a sequence of end tidal partial pressures of gas X is targeted at least once by:

(a) obtaining input of a measured baseline steady state value for PetX[i] for computing $F_IX$ at start of a sequence;

(b) targeting a selected target end tidal partial pressure of gas X (PetX[i]$^T$) for each of a series of tuning breaths [i+1 . . . i+n], wherein PetX[i]$^T$ differs from the baseline steady state value for PetX[i];

(c) comparing the targeted end tidal partial pressure of gas X (PetX[i+x]$^T$) for at least one tuning breath [i+x] in which the targeted end tidal gas concentration of gas X has been achieved without drift in a plurality of prior breaths [1+x−1, 1+x−2 . . . ] with a corresponding measured end tidal partial pressure of gas X for a corresponding breath [i+x] to quantify any discrepancy and adjusting the value of the total metabolic consumption or production of gas X in proportion to the discrepancy to reduce the discrepancy in a subsequent prospective computation of $F_IX$ including in any subsequent corresponding tuning breath [i+x] forming part of an iteration of the sequence.

All key inputs for computing $F_IX$ are itemized below.

We have found that a prospective model which predicts an $F_IX$ that is required to target a logistically attainable end tidal partial pressure of a gas X is simplified and enhanced by using a sequential gas delivery system (alternatively called a sequential gas delivery device, or sequential rebreathing).

According to another embodiment, the apparatus according to the invention is a "sequential gas delivery device" as defined hereafter. The sequential gas delivery device optionally comprises a partial rebreathing circuit or a sequential gas delivery circuit as defined hereafter.

The rate of gas exchange between the subject's mixed venous blood and alveoli for a respective breath [i] may be controlled by providing a partial re-breathing circuit through which the subject inspires a first gas in which the concentration of gas X is $F_IX$ and a second gas having a partial pressure of gas X which is substantially equivalent to the partial pressure of gas X in the subject's end tidal expired gas prior to gas exchange in the current respective breath [i] (the subject's last expired gas which is made available for re-breathing) or a gas formulated in situ to match a concentration of gas X which would have been exhaled in a prior breath. Practically, this may be accomplished by setting the rate of gas flow into the partial rebreathing circuit for a respective breath [i] to be less than the patient's minute ventilation or minute ventilation minus anatomic dead space ventilation (i.e. such that the last inspired second gas at least fills the anatomical dead space if not also part of the alveolar space) and using this rate or the volume of inspired gas it represents in a current breath to compute $F_IX$ for a respective breath [i].

With reference to parameters used to compute terms in equation 1 or 2, it is understood that phrases like "obtaining input" and similar expressions are intended to be understood broadly to encompass, without limitation, input obtained by or provided by an operator of a gas delivery device through any form of suitable hardware input device or via programming or any form of communication or recordation that is translatable into an electronic signal capable of controlling the gas delivery device.

According to another aspect, the invention is also directed to a method of controlling an amount of at least one gas X in a subject's lung to attain, preliminary to or during the course of a diagnostic or therapeutic procedure, at least one target end tidal partial pressure of a gas X.

A PetX[i] attained for any immediately previous breath [i−1] is:

a. alterable, prospectively, to any other logistically attainable value, in one breath, using a method or apparatus according to the invention;

b. maintainable, prospectively, without drift, in a respective breath [i] or in breath [i] and in one or more subsequent breaths [i+1] . . . [i+n] using a method or apparatus according to the invention.

According to one embodiment of the invention, a input of a concentration of gas X in the mixed venous blood entering the subject's lung for gas exchange in the respective breath [i]($C_{MV}X[i]$) can be obtained (e.g. predicted) by a compartmental modelling of gas dynamics. "Compartmental modeling of gas dynamics" means a method in which body tissues are modeled as system of one or more compartments characterized in terms of parameters from which the mixed-venous return of gas X can be predicted. These parameters include the total number of compartments, the fraction of the total cardiac output received by the respective compartment, the respective compartment's storage capacity for gas X and the fraction of the overall production/consumption of gas X that can be assigned to the compartment.

The total number of compartments (ncomp) in the model must be known or selected, and then each compartment (k) is assigned a fraction of the total cardiac output (qk), a storage capacity for gas X (dXk), and a fraction of the overall production/consumption rate of gas X (vXk). In general, the storage capacity for any gas X in a compartment is known for an average subject of a particular weight, and then scaled proportional to the actual weight of the subject under test.

Modeling/predicting the mixed-venous return can be done for any gas X using the following information:

1. A formula for conversion of end-tidal partial pressures to blood content of gas X (i.e. determining the content of the gas X in the pulmonary end-capillary blood based on data with respect to partial pressures).
2. the fraction of the overall production/consumption of the gas X which occurs in the compartment;
3. the storage capacity of the compartment for gas X;
4. blood flow to/from the compartment.

Some examples of gas X include isoflorane, carbon dioxide and oxygen.

Compartmental modeling of gas dynamics may be simplified using a single compartment model.

Means for controlling gas delivery typically include suitable gas flow controllers for controlling the rate of flow of one or more component gases. The gas delivery may be controlled by a computer for example an integrated computer chip or an external computer running specialized computer readable instructions via which inputs, computations and other determinations of parameter and controls are made/handled. The computer readable instructions may be embodied in non-transitory computer readable medium which be distributed as a computer program product.

It will be appreciated that logistically attainable target values for end tidal partial pressures of gas X may be set for respective breaths within a series breaths which are taken preliminary to or as part of a diagnostic or therapeutic procedure. Typically these values are defined in advance for the series or for at least part of the series of breaths. As described below, these individually logistically attainable values may be used to attain values in multiple breaths that are not logistically attainable in one breath.

The term "tuning" and related terms (e.g. tune, tuned etc.) means that a value for an estimated or measured parameter that is required to compute $F_IX$ is adjusted, as necessary or desirable, to enable more precise computation of the $F_IX$ required to achieve a $PetX[i]^T$, preferably based on observed differences between the target $PetX[i]^T$ set for one or more respective breaths and actual $PetX[i]$ value(s) obtained for the respective breath(s), if any, such that post-adjustment observed value(s) more closely match the respective target value(s). The tuned parameter(s) can be understood to fall into two categories: lung and non-lung related parameters. Preferably, the lung related parameter is FRC. A step change in the end tidal partial pressure of gas X is required to tune this parameter. Non-lung related parameters are preferably tissue related parameters, preferably those required for computing a compartmental model of gas dynamics, preferably parameters governing total metabolic production or consumption of gas X in the body or the overall cardiac output, optionally parameters affecting assessment of the contribution of a respective compartment to the mixed venous content of gas X, preferably as a function of the production or consumption of gas X in the respective compartment, the assigned storage capacity for gas X in the respective compartment and the contribution of blood flow from the respective compartment to the total cardiac output, for example, by observing that a repeatedly targeted value does not drift when attained. Drift can be defined in the negative or considered to have been corrected for, for example, if an adjusted value for a tissue related parameter results in a variation of no greater than 1 to 2 mm of Hg (ideally approximately 1 mm of Hg or less) between observed and targeted end tidal values of gas X for a series of 5 consecutive breaths (i.e. where the end tidal partial pressure of gas X is sought to be maintained for a series of breaths e.g. 30 breaths and observed drift is corrected).

Tuning FRC is important for transitioning accurately between end-tidal values. Tuning non-lung related parameters e.g. VCO2 is important so that the steady state error between end-tidal values is small. The tuning requirements depend on the goals of the targeting sequence. For example, in the case of inducing a step increase in the end-tidal partial pressure of CO2 from 40 mmHg to 50 mmHg, if attaining 50 mmHg in the first breath is important, FRC is preferably tuned. If achieving 50 mmHg in the first breath is not vital, but achieving this target in 20 breaths is all that may matter, a non-lung related parameter such as VCO2 should be tuned. If the goal of the end tidal targeting sequence is to achieve 50 mmHg in one breath, and then maintain 50 mmHg for the ensuing 20 breaths, both FRC and a non-lung related parameter should be tuned. If you don't care if you get to 50 mmHg in the first breath, and then drift to 55 after 20 breaths, don't tune either.

The following are examples of end tidal values that would be achieved for each combination. Assume transition is made on the second breath (bold):

Tuned FRC (good transition), untuned VCO2 (bad steady state error)—40, 50, 51, 52, 53, 54, 55, 55, 55, 55, 55, 55

Untuned FRC (bad transition), tuned VCO2 (no steady state error)—40, 59, 56, 53, 52, 51, 50, 50, 50, 50, 50

Tuned FRC (good transition), tuned VCO2 (no steady state error)—40, 50, 50, 50, 50, 50, 50, 50, 50

Untuned FRC (bad transition), untuned VCO2 (bad steady state error)—40, 62, 60, 58, 57, 56, 55, 55, 55, 55.

For example, to achieve a progressively increasing end tidal partial pressure of gas X where the actual or absolute values are not of concern, only that the values keep increasing in each breath, it would not be necessary to tune FRC or VCO2. However, to transition from 40 to 50 mmHg (for example, where gas X is CO2), though not necessarily in one breath, it would be preferable to tune a non-lung related parameter e.g. VCO2 but not FRC. If it were important to transition from 40 mmHg to 50 mmHg in one breath, but not so important if the end tidal values drifted away from 50 mmHg after the first breath, it would be important to tune FRC but not VCO2 etc. Nevertheless, a target would be set for each respective breath [i] and that target would be effectively attained with a degree of accuracy and immediacy necessary for the application in question. Accordingly, a tidal based model for targeting end tidal partial pressure of a gas X provides a tunable flexible system for attaining those targets in line with a wide variety of objectives of the user.

It is to be understood that this tuning can be applied independently to each of the gases that are being targeted, as each gas can be targeted independently of the other gases.

An attainable target may be maintained in one or more subsequent breaths by setting the target end tidal value for the respective breath to be the same as $PetX[i-1]$. A target that is not attainable in one breath may be obtained in a series of breaths [i] . . . [i+n].

As suggested above and discussed below, it is possible that a particular end tidal partial pressure is not logistically attainable in one breath. If logistically attainable at all, such a target may be logistically attained only after multiple breaths. In contrast to methods requiring negative feedback, such as dynamic end tidal forcing, in one aspect of the method of the present invention this number of breaths may be pre-defined prospectively. This number of breaths may also be minimized so that the ultimate end tidal target is attained as rapidly as logistically feasible, for example by simple computational trial and error with respect to an incremented series of target. As described below, logistic constraints could be seen as limitations to inhaling the amount of the gas X that needs to be inhaled to reach a target concentration on the next breath; this could be because of limitations of available concentration X, or volume of inspired gas or both. Mandatory constraints are at least those inherent in any method of controlling the end tidal partial pressure of a gas X by way of inhalation of concentrations of gas X in that $F_IX$ cannot be less 0% and greater than 100% for any given breath. Constraints may also be selected as a matter of operational necessity or efficiency—so called "operational constraints" which may be self-imposed but not mandatory in all cases. For example, practically speaking, it may be inadvisable for safety reasons to administer a gas X (especially where gas X is not oxygen) in the highest feasible concentrations due to patient safety risks accompanying failure of the system. Accordingly, for safety reasons it may be advisable for a component gas comprising gas X to have at least 10% oxygen thereby defining an optional logistical limit of the method. Therefore what is logistically achievable is understood to be operationally limited by the composition of all the gas sources to which the apparatus is connected at any point in time. Furthermore, as described below, sequential gas delivery is typically effected by delivering a gas of a first composition followed by a neutral gas. The rate of flow and hence volume of the first gas generally controlled to within certain parameters so that the second gas at least fills the anatomic dead space. This is operationally mandatory in the sense that not all values for this parameter are workable, especially if a medically relevant target end tidal partial pressure of gas X is sought to be achieved in one breath as opposed to incrementally over several breaths. What is logistically attainable will be dictated by the extant rate of flow, if unvaried, or if varied, by the range of logistically practicable rates of flow. Hence, what is logistically attainable may be tied to independently controlled parameters which may or may not be varied. Hence, some of these operational parameters may be mandatory in a particular context or in a universal sense (running the system so that it always works without reset e.g. recalculation of prospectively calculated $F_IX$ values for a dynamic set of breaths of interest if the tidal volume falls outside established controls.

According to one embodiment of the method, the model of gas dynamics that is used to predict $C_{MV}X[i]$ in the mixed venous blood entering the subject's lung for gas exchange in the respective breath [i] estimates a value of $C_{MV}X[i]$) by: (a) dividing tissues to which the subject's arterial blood circulates into one or more compartments (k); and (b) determining the contribution of a respective compartment to the mixed venous content of gas X as a function of the production or consumption of gas X in the respective compartment, the assigned storage capacity for gas X in the respective compartment and the contribution of blood flow from the respective compartment to the total cardiac output or pulmonary blood flow. For example, where gas X is carbon dioxide the content of carbon dioxide in the mixed venous blood leaving a compartment $C_VCO2_k[i]$ is determined by assigning to a compartment a fraction of the overall metabolic carbon dioxide production ($vco2_k$), a fraction of the total cardiac output ($q_k$) and a storage capacity for carbon dioxide ($dCO2_k$).

In contrast to a negative feedback system, the afore-described system is a prospective end-tidal targeting system. Prior to execution of an end-tidal targeting sequence, the tissue model is used to predict the time course of the mixed-venous blood gases that will result from ideal execution of the sequence.

The time course of predicted mixed-venous gases is used to compute the series of inspired gas mixtures required to realize the target end-tidal partial pressures of gases. In this way, assuming that the end-tidal partial pressures of gases adhere to the targets allows prediction of the mixed-venous gases, and prediction of the mixed-venous gases allows a priori calculation of the inspired gas mixtures required to accurately implement the end-tidal targets. There is no requirement to modify the series of the inspired gas mixtures calculated before execution of the sequence based on deviations of the measured end-tidal partial pressures of gases from the targets during execution of the sequence.

Instead, the system is tuned to obtain tuned values for certain parameters before execution of the sequence so that the end-tidal partial pressures of gases induced during sequence execution closely adhere to the target functions without the need for any feedback control.

Optionally, the program code includes code for directing a suitable gas delivery device such as a rapid flow controller to deliver a gas X containing gas having an $F_IX$ output from a mass balance equation. The term "gas delivery means" by contrast to gas delivery device refers to a discrete component of a gas delivery device that is used to control the volume of gas delivered at a particular increment in time such as a rapid flow controller.

It will be appreciated that each of the key method steps for carrying out the invention can be functionally apportioned to different physical components or different computer programs and combinations of both. Furthermore a device according to the invention will optionally comprise one or more physical components in the form of a gas analyzer, a pressure transducer, a display, a computer, a gas delivery device such as a rapid flow controller, a gas channeling means (gas conduits/tubes), standard electronic components making up a PCB, input devices for setting parameters etc. The various means for carrying out these steps include without limitation one in the same physical means, or different physical means on different devices, the same device or the same device component. Depending on the number of added gases these components may multiplied or where possible shared.

In another aspect, the present invention is also directed to a device comprising an integrated circuit chip configured for carrying out the method, or a printed circuit board (comprising discrete or integrated electronic components). The device optionally includes at least one gas delivery means such as a rapid flow controller. The device optionally includes an input device for inputting various parameters described herein. The parameters can be input via a variety of means including, but not limited to, a keyboard, mouse, dial, knob, touch screen, button, or set of buttons.

It is understood that any input, computation, output, etc. described herein can be accomplished by a variety of signal processing means including, but not limited to, a programmable processor, a programmable microcontroller, a dedicated integrated circuit, a programmable integrated circuit, discrete analog or digital circuitry, mechanical components, optical components, or electrical components. For example, the signal processing steps needed for executing the inputs, computations and outputs can physically embodied in a field programmable gate array or an application specific integrated circuit.

The term "blending" may be used to describe the act of organizing delivery of one gas in conjunction with at least one other and hence the term blending optionally encompasses physical blending and coordinated release of individual gas components.

The term "computer" is used broadly to refer to any device (constituted by one or any suitable combination of components) which may be employed in conjunction with discrete electronic components to perform the functions contemplated herein, including computing and obtaining input signals and providing output signals, and optionally storing data for computation, for example inputs/outputs to and from electronic components and application specific device components as contemplated herein. As contemplated herein a signal processor or processing device in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a pressure transducer, a gas analyzer, any type of input device for inputting a target end tidal partial pressure of gas X (for example, a knob, dial, keyboard, keypad, mouse, touch screen etc.), input from a computer readable memory etc. Key outputs include output of the flow and/or composition of gas required to a flow controller.

For example of a compartmental model for mixed venous blood carbon dioxide dynamics may assign body tissues to k compartments e.g. 5 compartments and assign the contribution of a respective compartment to the mixed venous content of carbon dioxide as a function of the production of carbon dioxide in the respective compartment, the assigned storage capacity for carbon dioxide in the respective compartment and the contribution of blood flow from the respective compartment to the total cardiac output.

In one aspect, the present invention is directed to a non-transitory computer readable memory device having recorded thereon computer executable instructions for carrying out one or more embodiments of the above-identified method. The invention is not limited by a particular physical memory format on which such instructions are recorded for access by a computer. Non-volatile memory exists in a number of physical forms including non-erasable and erasable types. Hard drives, DVDs/CDs and various types of flash memory may be mentioned. The invention, in one broad aspect, is directed to a non-transitory computer readable medium comprising computer executable instructions for carrying out one or more embodiments of the above-identified method. The instructions may take the form of program code for controlling operation of an electronic device, the program code including code for carrying out the various steps of a method or control of an apparatus as defined above.

A "gas delivery device" means any device that can make a gas of variable/selectable composition available for inspiration. The gas delivery apparatus may be used in conjunction with a ventilator or any other device associated with a breathing circuit from which the subject is able to inspire a gas of variable/controllable composition without substantial resistance. Preferably, the composition of the gas and/or flow rate is under computer control. For example, such a device may be adapted to deliver at least one gas (pure or pre-blended) at a suitable pre-defined rate of flow. The rate of flow may be selectable using a form of input device such a dial, lever, mouse, key board, touch pad or touch screen. Preferably the device provides for one or more pure or blended gases to be combined i.e. "a gas blender".

A "gas blender" means a device that combines one or more stored (optionally stored under pressure or delivered by a pump) gases in a pre-defined or selectable proportion for delivery a selectable rate of flow, preferably under computer control. For example or more stored gases may be combined with pumped room air or a combination of pure or blended (each blended gas may have at least 10% oxygen for safety) gases respectively contain one of carbon dioxide, oxygen and nitrogen as the sole or predominant component. Optionally, the selectable proportion is controlled automatically using an input device, optionally by variably controlling the flow of each stored gas (pure or pre-blended) separately, preferably using rapid flow controllers, to enable various concentrations or partial pressures of a gas X to be selected at will within a pre-defined narrow or broad range. For example, a suitable blender may employ one or more gas reservoirs, or may be a high flow blender which blows gas past the mouth i.e. in which gas that is not inspired is vented to the room.

A "partial rebreathing circuit" is any breathing circuit in which a subject's gas requirements for a breath are made up in part by a first gas of a selectable composition, and a rebreathed gas to the extent that the first gas does not fully satisfy the subject's volume gas requirements for the breath. The first gas must be selectable in at least one of composition or amount. Preferably the amount and composition of the first gas is selectable. The rebreathed gas composition optionally consists of previously exhaled gas that has been stored or a gas formulated to have the same concentration of gas X as previously exhaled gas or a second gas has a gas X concentration that is selected to correspond (i.e. has the same concentration) as that of the targeted end tidal gas composition for a respective breath [i].

Preferably the circuit is designed or employable so that the subject receives the entirety of or a known amount of the first gas in every breath or in a consecutive series of breaths forming part of gas delivery regimen. In a general sense a re-breathed gas serves a key role in that it does not contribute significantly to the partial pressure gradient for gas flow between the lung and the pulmonary circulation when intake of the gas at least fills the entirety of the anatomic dead space. Therefore, in the case of a spontaneously breathing subject (whose tidal volume is not controlled e.g. via a ventilator) the subject's unpredictable tidal volume does not defeat prospective computation of the controlled gas composition required to attain or target PetX[i] for a respective breath [i].

Optionally, the "rebreathed gas" may be constituted by or substituted by a prepared gas (in terms of its gas X content). Thus, according to one embodiment of the invention, the second gas has a gas X concentration that is selected to correspond to that of the targeted end tidal gas composition for a respective breath [i]. The volume of the first inspired gas may also be adjusted (e.g. reduced) to target $PetX[i]^T$ for a respective breath [i] such that the subject receives an optimal amount of a gas having a gas X concentration that corresponds to $PetX[i]^T$.

As alluded to above, it will be appreciated that the gas X content of a prepared gas can be formulated to represent a gas of a "neutral" composition. Thus the total inspired gas for a respective breath [i] will comprise a first inspired gas having a controlled volume and gas X concentration ($F_IX$) and a second gas which has a gas X content whose contribution to establishing a partial pressure gradient between the lung and pulmonary circulation is optionally minimized. In a broader sense, the second inspired gas content of gas X can be optimized to attain a targeted end tidal concentration (for a universal set of circumstances) and in a sub-optimal sense this concentration at least does not defeat the ability to prospectively compute an $F_IX$ for the purposes of attaining or targeting a PetX[i] for a respective breath [i] (i.e. not knowing the subject's tidal volume for a respective breath [i] will not preclude such computation).

"Prospectively" or a "prospective computation" means, with reference to a determination of an amount of gas X required to be inspired by the subject in an inspired gas to attain or target a $PetX[i]^T$ for a respective breath [i] (optionally computed in terms of $F_IX$), using inputs required to compute a mass balance equation (preferably including $C_{MV}X[i]$), without necessary recourse to feedback to attain rapidly and repeatably. In contrast, to a negative feedback system, which relies on ongoing measurements of PetX[i] to provide feedback for continually adjusting computed $F_IX$ values to minimize the discrepancy between target and measured PetX[i] values, the system of the present invention is adapted to attain logistically achievable end tidal values rapidly and accurately (as defined herein) without recourse to feedback. As discussed herein, a negative feedback system suffers from an inherent trade-off between response time and stability. According to the present invention, recourse to feedback is designed to be unnecessary for the purpose of attaining logistically achievable PetX targets rapidly and predictably.

Of further consideration are the delays associated with measurement of the end-tidal partial pressures of gases which are required for feedback into the system. Gas composition analysis is performed by continuously drawing gas from proximal to the subject's airway into a gas analyzer through a sampling catheter. The gas analyzer returns a time varying signal of gas composition which is, however, delayed from the actual ventilatory phase of the subject by the travel time through the sampling catheter and the response time of the gas analyzer. Therefore, at the start of any inspiration, the end-tidal partial pressures of gases from the immediately previous breath are not yet known. Where the sampling catheters are long, such as in an MRI environment where the patient is in the MRI scanner and the gas analyzers must be placed in the control room, this delay can reach three or more breaths. As in any negative feedback system, this delay in measuring the controlled parameter will further destabilize and limit the response time of the system.

A "sequential gas delivery device" means, with respect to delivering a gas in successive respective breaths [i], a device for delivery of a controlled gas mixture in the first part of a respective breath [i] followed by a "neutral" gas in the second part of the respective breath [i]. A controlled gas mixture is any gas that has a controllable composition with respect to one or more gases of interest used to compose it. Accordingly, where the gas of interest is a gas X, the controlled gas mixture has an amount of gas X, optionally defined in terms of a concentration of gas X denoted as $F_IX$. The controlled gas mixture may be referred to, for convenience, as a first inspired gas. Gas inspired in any breath is "neutral", inter alia, if it has the same composition as gas expired by the subject in a previous breath. The term "neutral" gas is used because the gas in question is one which has the same partial pressure of one or more gases of interest as the blood, in the alveoli, or in the pulmonary capillaries, and hence, upon inspiration into the alveolar space, in the second part of a respective breath, this gas does not exchange any gas with the pulmonary circulation. Unless otherwise defined explicitly or implicitly a gas of interest is generally one for which the end tidal partial pressure is sought to be controlled according to the invention.

A volume of gas that enters the alveolar space and exchanges gas with the pulmonary circulation for a breath [i] may be defined independently of a fixed tidal volume, for example by:
 a. setting the rate of flow of a controlled gas mixture (also termed fresh gas flow rate) in a rebreathing circuit to be less than the patient's minute ventilation or minute ventilation minus anatomic dead space ventilation (i.e. such that the last inspired second gas at least fills the anatomical dead space if not also part of the alveolar space);
 b. obtaining input of the rate of flow or volume of the controlled gas mixture into the circuit for the respective breath (this rate can be maintained from breath to breath or varied) and computing the effective volume of alveolar gas exchange for the respective breath based on the rate of fresh gas flow for the respective breath.

According to one embodiment, the rebreathing circuit is a sequential gas delivery circuit.

According to another embodiment, volume of gas that enters the alveolar space and exchanges gas with the pulmonary circulation is determined by utilizing a fixed tidal volume set for the respective breath (e.g. using a ventilator) and subtracting a volume corresponding to the subject's anatomic dead space volume.

The $F_IX$ may be set independently of the concentration of any other component of the inspiratory gas.

Optionally, a gas X and a gas Y are components of the inspired gas and a target arterial concentration of gas X and a target arterial concentration of a gas Y are selected for a respective breath, independently of each other, and, if present, independently of the concentration of any other component Z of the inspiratory gas.

A mass balance equation that comprises terms "corresponding to" all or an application-specific subset of the terms in equations 1 or 2 above means that the same underlying parameters are accounted for.

According to one aspect of the PMBT invention (which may be implemented in connection with any one or more of compatible embodiments of the invention defined hereinabove), the invention is directed to an apparatus for controlling an amount of at least one gas X in a subject's lung to attain a series of targeted end tidal partial pressures of at least one gas X ($PetX^T$), the series of targeted end tidal partial pressures of at least one gas X ($PetX^T$) adapted to stimulate a physiological response, the apparatus comprising:
(1) a gas delivery device;
(2) a control system for controlling the gas delivery device, wherein the control system is adapted to target a series of $PetX^T$ values for a respective series of intervals, the control system including means for:
 a. Obtaining input of a series of logistically attainable $PetX^T$ values for the series of respective intervals; and
 b. Determining an amount of gas X required to be inspired by the subject in an inspired gas to target the $PetX^T$ for a respective interval;
 c. Controlling the amount of gas X in a volume of gas delivered to the subject in a respective interval to target the respective $PetX^T$ for the interval.

The series of $PetX^T$ values preferably comprise at least one of a set of $PetX^T$ increments and a set of $PetX^T$ decrements.

The term "interval" is used broadly to mean a time interval of selected length, an interval defined by the duration of a respective inspiratory cycle and a previous or ensuing expiratory cycle, for example, a respective breath [i] defined by an inspiratory cycle and the expiratory cycle which follows it, and/or an interval defined by a pattern of a physiological response. The term 'pattern of a physiological response' means a pattern sufficient to define a dose-response (stimulus-response) relationship for a full range of the physiologic response or for at least a part thereof that reveals a pattern of interest, wherein the increments in dose or stimulus are selected to disclose the true shape of the dose response curve. A portion of interest may of diagnostic or medical interest to define a normal pattern of the response for example to differentiate between variations in a normal response for different groups e.g. ages, and optionally a differential response e.g. particular range or prevalence of a response or a different or pathologic response, associated with a condition or disease. For example, a pattern may disclose a linear, exponential or sigmoidal dose response curve for an individual or group of common individuals selected from at least one of persons having a 'normal' physiological response and persons disclosing a different or pathological physiological response. For example, a pattern may disclose that a response is sigmoidal and not linear (e.g. it is only linear over a certain range of the stimulus) when a fuller range of the response is probed using a suitable range and series of smaller changes in stimulus. For example, an interval of diagnostic interest may be a fraction of the amount of time required to observe the time course of the response wherein the fraction is sufficiently small to obtain a set of values defining the pattern of response. The ramp sequence may also be selected to determine a time course of a full or partial range of a physiological response by tracking signals signifying that a particular condition, associated with a direct or indirect measure of the response, has been met, the condition preferably of the type satisfied by attainment or projected attainment of a threshold amount change in a measurable parameter correlated with a physiologic response to a stimulus comprising or consisting of an increment or decrement in a subject's end tidal partial pressure of gas X. A fraction or proportionate amount of a time period required to observe a continuous time course of a physiological response or satisfy a set threshold amount of change in the response (attained or predicted to be attained based on a known or predictable mathematical relationship between the stimulus—an increment or decrement in PetX—and a measurable parameter that defines the time course of the response), is then defined to be sufficient to demarcate the end of a previous interval and the beginning of a next ensuing interval. The time course may be selected to grade individuals in terms of the overall appearance of the pattern (measurement of a continuous variable) or differentiate between populations with respect satisfying one or more individual criteria (e.g. a discontinuous variable eliciting a yes/no answer).

A gas delivery device can be controlled to attain a series of targeted end tidal partial pressures of at least one gas X ($PetX^T$) by the prospective model described herein; or by a combination of a prospective model and feedback control (known as dynamic end tidal forcing), for example, wherein the feedback loop (e.g. using a PID controller) adds a control signal to adjust a prospective determination of $F_IX$; the control signal generated based on the difference between the target and measured end tidal values. Computation of FIX can be accomplished using the tidal model equations herein by adapting the continuous flow equations published by Robbins and Swanson.

According to one aspect of the PMBT invention (which may be implemented in connection with any one or more of compatible embodiments of the invention defined hereinabove), the invention is directed to a method of controlling an amount of at least one gas X in a subject's lung to attain at least one targeted end tidal partial pressure of the at least one gas X, comprising the steps of:

a. Obtaining input of a logistically attainable end tidal partial pressure of gas X ($PetX[i]^T$) for a series of respective breaths [i];

b. Obtaining input of a prospective computation of an amount of gas X required to be inspired by the subject in an inspired gas to target the $PetX[i]^T$ for a respective breath [i] using inputs required to compute a mass balance equation, wherein one or more values required to control the amount of gas X in a volume of gas delivered to the subject is output from the mass balance equation; and optionally c. Controlling the amount gas X in a volume of gas delivered to the subject in a respective breath [i] to target the respective $PetX[i]^T$ based on the prospective computation;

and wherein the respective $PetX[i]^T$ for the series of breaths [i] increases or decreases from the start of the series to the end of the series (from $PetX[i^1]^T$ to $PetX[i^n]^T$) in accordance with a ramp sequence (as defined below).

Optionally, the respective $PetX[i]^T$ for the series of breaths [i] increases every Nth breath in respective selected increments ("Z") from the start of the series to the end of the series (from $PetX[i^1]^T$ to $PetX[i^n]^T$), wherein either N equals 1 and Z is greater than 0 in each breath in the series, or N is greater than 1 and Z may be zero in breaths which are not the Nth breath and Z is greater than 0 in every Nth breath.

Optionally, the respective $PetX[i]^T$ for the series of breaths [i] decreases every Nth breath in respective selected decrements ("Z") from the start of the series to the end of the series (from $PetX[i^1]^T$ to $PetX[i^n]^T$), wherein either N equals 1 and Z is greater than 0, or N is greater than 1 and Z may be zero in breaths which are not the Nth breath and Z is greater than 0 in every Nth breath Accordingly, $PetX[i]^T$ may change every Nth breath in respective selected increments or decrements ("Z") from the start of the series to the end of the series (from $PetX[i^1]^T$ to $PetX[i^n]^T$), wherein N equals 1 and Z is greater than 0. In another embodiment, N is greater than 1 and Z may be zero in breaths which are not the Nth breath.

Embodiments in which $PetX[i^1]^T$ increases include the following. In one embodiment, "Z" is greater 0 and is the same in each breath in the series (N=1). For example, N may equal 1 and "Z" may equal 8. Therefore, for example, a target end tidal oxygen concentration may increase every breath (N=1) from $[i]^1$ to $[i]^n$ from $PetX[i^1]^T$=100 mm Hg to $PetX[i^n]^T$=180 mm Hg over the course of the next 10 contiguous breaths (respective targets in mm of Hg=108, 116, 124, 132, 140, 148, 156, 164, 172, 180). As another example, N may equal 5 and same end tidal target value may be maintained at the same target for the 4 breaths in between each 5$^{th}$ breath such that it would take approximately 50 breath to span the same range of end tidal targets from $[i]^1=PetX[i^1]^T$=100 mm Hg to $[i]^{50}=PetX[i^{50}]^T$=180 mm Hg. This same sequence may be expressed another way i.e. Z is changing and for the series of fifty breaths as follows: Z equals, respectively 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8.

In one embodiment, Z is selected to correspond to a selected rate of change in a physiological response to a stimulus (the stimulus being a correlate of $PetX[i]^T$ such as the arterial partial pressure of gas X (PaX)). The selected rate of change corresponds to a rate wherein a targeted physiologic response is substantially realized for each increment/decrement before the next increment/decrement, such that successive measurements of the response are substantially matched to an increment/decrement in a change in stimulus. Accordingly, it is possible to plot the change in response with respect to the change in $PetX[i]^T$ with substantial accuracy. For example, where the time course of the response of a physiologic parameter is exponential, the rate of change in $PetX[i]^T$ may be selected such that three time constants in the progress of the response (approximately 95% response) are achieved before the next increment/decrement in $PetX[i]^T$ stimulus is given. A time interval for executing the range in stimulus "R" or the range (extent) of the expected response "r" may be selected and the target change per breath in stimulus readily mathematically determined. For example, with respect to ramping up $PetCO_2[i]^T$ from 35 to 50 mm of Hg over a selected time period (e.g. approx. 5 minutes) increasing $PetCO_2[i]^T$ approx. 0.25 mm Hg every breath may define a suitable ramp sequence. Optionally, this rate may be corroborated. Corroboratively, a greater than 95% CVR response to a change in $PaCO_2$ may be determined to be achieved in 16-18 seconds. Thus increments of 1 mm of Hg every 16 second would be suitable. Assuming a subject inhales 15 times per minute (1 breath every 4 seconds, this corresponds to 0.25 mm of Hg every breath. Accordingly, according to one embodiment of the invention, optionally, the time interval over which the response is measured and the range of change in stimulus range may be input to facilitate execution of a ramp sequence so that a series of $PetCO_2[i]^T$ targets for the intervening breaths may be correspondingly obtained.

Optionally, with respect to increases in $PetCO_2[i]^T$, N is advantageously 1, 2 or 3 breaths, optionally 1 breath, and Z is the optionally the same for each increase, depending on the total time interval for executing the range in stimulus Z or desired response range optionally ranging from 0.2 to 2 mm Hg. Optionally, with respect to increases in $PetO2[i]^T$ N is advantageously 1 to 5, optionally 1, and Z is the optionally the same for each increase, Z ranging from 1 to 20 mm Hg. Simply by way of example, $PetO_2[i]^T$ may be increased every Nth breath wherein N=1 and Z=8 for each successive breath in the series e.g. ranging from 100 mm Hg to 350 mm Hg) while $PetCO_2[i]^T$ is maintained constant. In another embodiment, $PetCO2[i]^T$ is increased each Nth breath e.g. from 35 mm Hg to 50 mm Hg (N=1, Z=0.25 for each successive breath in the series) while $PetO_2[i]^T$ is maintained constant.

Advantageously, as regards such sequences, where the targets are increased or decreased at a rate selected for observing a substantial response to an increment or decrement in stimulus (termed a "ramp sequence"); e.g. with respect to an exponential response, optionally at least a response corresponding to two time constants, optionally at least a 90-95% response or a response corresponding to three time constants, optionally approximately linearly with respect to time, the response (e.g. CVR) to a change in the end tidal concentration of gas X e.g. carbon dioxide, is substantially achieved within a given time increment e.g. spanning 4 breaths, and is optionally plotted (measurement may be more frequent) approximately every 4 breaths, in contrast to making the change in stimulus in one step, ideally, in one breath, in which case, the continuous plotting of the response reveals the time course of the response to the stimulus.

Accordingly the PMBT invention is also directed to an apparatus for controlling an amount of at least one gas X in a subject's lung to attain a targeted end tidal partial pressure of the at least one gas X, comprising:

(1) a gas delivery device;
(2) a control system for controlling the gas delivery device including means for:
a. Obtaining input of a concentration of gas X in the mixed venous blood entering the subject's pulmonary circulation for gas exchange in one or more respective breaths [i] ($C_{MV}X[i]$);
b. Obtaining input of a logistically attainable end tidal partial pressure of gas X ($PetX[i]^T$) for a respective breath [i];
c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
d. Controlling the amount of gas X in a volume of gas delivered to the subject in a respective breath [i] to target the respective $PetX[i]^T$ based on the prospective computation; and optionally
e. Inputting values for execution of a ramp sequence (optionally via means for setting a cumulative time interval for measuring the response and a range of the stimulus or response to be canvassed, or optionally an increment or decrement Z (in the example above 0.25 mm of Hg) for each a series of respective breaths $[i]^1$ to $[i]^n$, and optionally N.

N may be fixed at 1 in which case Z will be greater than 0 or N is greater than 1 and Z may be zero in breaths which are not the Nth breath and Z is greater than 0 in every Nth breath.

The PMBT invention is described hereafter in terms of one or more optional embodiments of a gas X, namely carbon dioxide and oxygen.

Prospective Modelling

Mass balance equations of gases in the lung are conventionally derived from a continuous flow model of the pulmonary ventilation. In this model, ventilation is represented as a continuous flow through the lungs, which enters and exits the lungs through separate conduits. As a consequence, for example, the anatomical dead space would not factor into the mass balance other than to reduce the overall ventilatory flow into the alveolar space. In reality, however, ventilation in humans is not continuous, but tidal. Gas does not flow through the lungs, but enters the lungs during a distinct inspiration phase of the breath and exits during a subsequent expiration phase of the breath. In each breath cycle, gas is inspired into the lungs via the airways and expired from the lungs via the same airways through which gas was inspired. One possible implication, for example, is that the first gas inspired into the alveolar space in any breath is residual gas which remains in the anatomical dead space following the previous expiration. Continuous flow models neglect the inspiration of residual gas from the anatomical dead space, and therefore, since accounting for such a factor is generally desirable, do not accurately represent the flux of gases in the lungs.

As continuous flow models of pulmonary ventilation do not correctly represent the flux of gases in the lungs, the end-tidal partial pressures of gases induced from the inspiration of gas mixtures computed from such a model will, necessarily, deviate from the targets.

By contrast, according to one aspect of the PMBT invention, a mass balance equation of gases in the lungs is preferably formulated in terms discrete respective breaths [i] including respective discrete volumes corresponding to one or more of the FRC, anatomic dead space, the volume of gas X transferred between the pulmonary circulation and the lung in a respective breath [i] and an individual tidal volume of a respective breath [i]) is adaptable to account, for example, for inspiration of residual gas from the anatomical dead space into the alveolar space in each breath. Inasmuch as a tidal model more faithfully represents the actual flux of gases in the lungs compared with the conventional model, the induced end-tidal partial pressures of gases, to an extent that the model is fully exploited, it will more closely adhere to the targets compared with results achieved using a continuous flow model.

Moreover, we have found that using a tidal model of pulmonary ventilation, can be synergistically employed with a sequential gas delivery system to facilitate closer adherence to targets in both ventilated and spontaneously breathing subjects without reliance on a negative feedback system.

According to the PMBT invention, a prospective determination of pulmonary ventilation and gas exchange with the blood can efficiently exploited even in spontaneously breathing subjects where the ventilatory parameters are highly variable and difficult to measure.

Where mechanical ventilation is employed, a prospective model of pulmonary ventilation and gas exchange with the blood envisages that the subject's ventilatory parameters can be estimated or measured to a level of accuracy sufficient to employ prospective control of the end-tidal partial pressures of one of more gases.

According to one embodiment of the PMBT invention, a technique of inspiratory gas delivery, sequential rebreathing, which, when using a tidal model of the pulmonary ventilation, significantly reduces or eliminates the dependence of the calculation of the inspired gas composition to be delivered in each breath, and therefore the actual end-tidal partial pressures of gases induced, on the subject's ventilatory parameters.

In parallel to what we have observed from studies with respect to the subject's ventilatory parameters, we have found that when we run a set of standardized tuning sequences, our model of the tissues more accurately reflects the actual dynamics of the gas stored in the subject's tissues. The model parameters may be refined until the end-tidal partial pressures of gases induced by execution of the tuning sequences sufficiently adhere to the targets without the use of any feedback control.

Sequential Gas Delivery

Sequential rebreathing is a technique whereby two different gases are inspired in each breath—a controlled gas mixture followed by a "neutral" gas. A controlled gas mixture is any gas that has a controllable composition. Gas inspired in any breath is neutral if it has the same composition as gas expired by the subject in a previous breath. Neutral gas is termed as such since it has substantially the same partial pressures of gases as the blood in the pulmonary capillaries, and hence, upon inspiration into the alveolar space, does not substantially exchange any gas with the pulmonary circulation. Optionally, the rebreathed gas has a composition that is selected to correspond (i.e. have the same gas X concentration as that of) the targeted end tidal gas composition for a respective breath [i]. It will be appreciated that a modified sequential gas delivery circuit in which the subject exhales via a port leading to atmosphere and draws on a second gas formulated by a second gas delivery device (e.g. a gas blender) could be used for this purpose, for example where the second gas is deposited in an open ended reservoir downstream of a sequential gas delivery valve, for example within a conduit of suitable volume as exemplified in FIG. 7 of U.S. Pat. No. 6,799,570.

Sequential rebreathing is implemented with a sequential gas delivery breathing circuit which controls the sequence and volumes of gases inspired by the subject. A sequential gas delivery circuit may be comprised of active or passive valves and/or a computer or other electronic means to control the volumes of, and/or switch the composition or source of, the gas inspired by the subject.

The controlled gas mixture is made available to the sequential gas delivery circuit for inspiration, optionally, at a fixed rate. On each inspiration, the sequential gas delivery circuit ensures the controlled gas mixture is inspired first, for example with active or passive valves that connect the subject's airway to a source of the controlled gas mixture. The supply of the controlled gas mixture is controlled so that it is reliably depleted in each breath.

Once the supply of the controlled gas mixture is exhausted, the sequential gas delivery circuit provides the balance of the tidal volume from a supply of neutral gas exclusively, for example with active or passive valves that connect the subject airway to the subject's exhaled gas from a previous breath.

Gas expired in previous breaths, collected in a reservoir, is re-inspired in a subsequent breath. Alternatively, the composition of gas expired by the subject can be measured with a gas analyzer and a gas with equal composition delivered to the subject as neutral gas.

During inspiration of the neutral gas and expiration, the supply of the controlled gas mixture for the next inspiration accumulates at the rate it is made available to the sequential gas delivery circuit. In this way, the subject inspires only a fixed minute volume of the controlled gas mixture, determined by the rate at which the controlled gas mixture is made available to the sequential gas delivery circuit, independent of the subject's total minute ventilation, and the balance of subject's the minute ventilation is made up of neutral gas.

Examples of suitable sequential gas delivery circuits are disclosed in US Patent Application No. 20070062534.

The fixed availability of the controlled gas mixture may be accomplished by delivering a fixed flow rate of the controlled mixture to a physical reservoir from which the subject inspires. Upon exhaustion of the reservoir, the source of inspiratory gas is switched, by active or passive means, to neutral gas from a second gas source, for example a second reservoir, from which the balance of the tidal volume is provided.

It is assumed that in each breath the volume of the neutral gas inspired at least fills the subject's anatomical dead space. Herein, all of the controlled gas mixture reaches the alveolar space and any of the neutral gas that reaches the alveolar space does not exchange gas with the circulation as it is already in equilibrium with the pulmonary capillary blood.

Sequential gas delivery circuits may be imperfect in the sense that a subject will inspire what is substantially entirely a controlled gas mixture first. However, upon exhaustion of the supply of the controlled gas mixture, when neutral gas is inspired, an amount of controlled gas mixture is continually inspired along with the neutral gas rather than being accumulated by the sequential gas delivery circuit for the next inspiration (2). The result is that the subject inspires exclusively controlled gas mixture, followed by a blend of neutral gas and controlled gas mixture. As a result of the imperfect switching of gases, a small amount of the controlled gas mixture is inspired at the end of inspiration and enters the anatomical dead space rather than reaching the alveolar space. In practise, the amount of controlled gas mixture lost to the anatomical dead space is small, and therefore, the amount of controlled gas mixture that reaches the alveolar space can still be assumed equal to the rate at which the controlled gas mixture is made available to the sequential gas delivery circuit for inspiration. Therefore, the method described herein can be executed, as described, with imperfect sequential gas delivery circuits.

A simple implementation of sequential rebreathing using a gas blender and passive sequential gas delivery circuit is described in references cited below (2; 3). Other implementations of sequential gas delivery are described in patents (4-8).

The contents of all references set forth below are hereby incorporated by reference.

Various implementations of sequential gas delivery have described by Joseph Fisher et al. in the scientific and patent literature.

Figure 15:
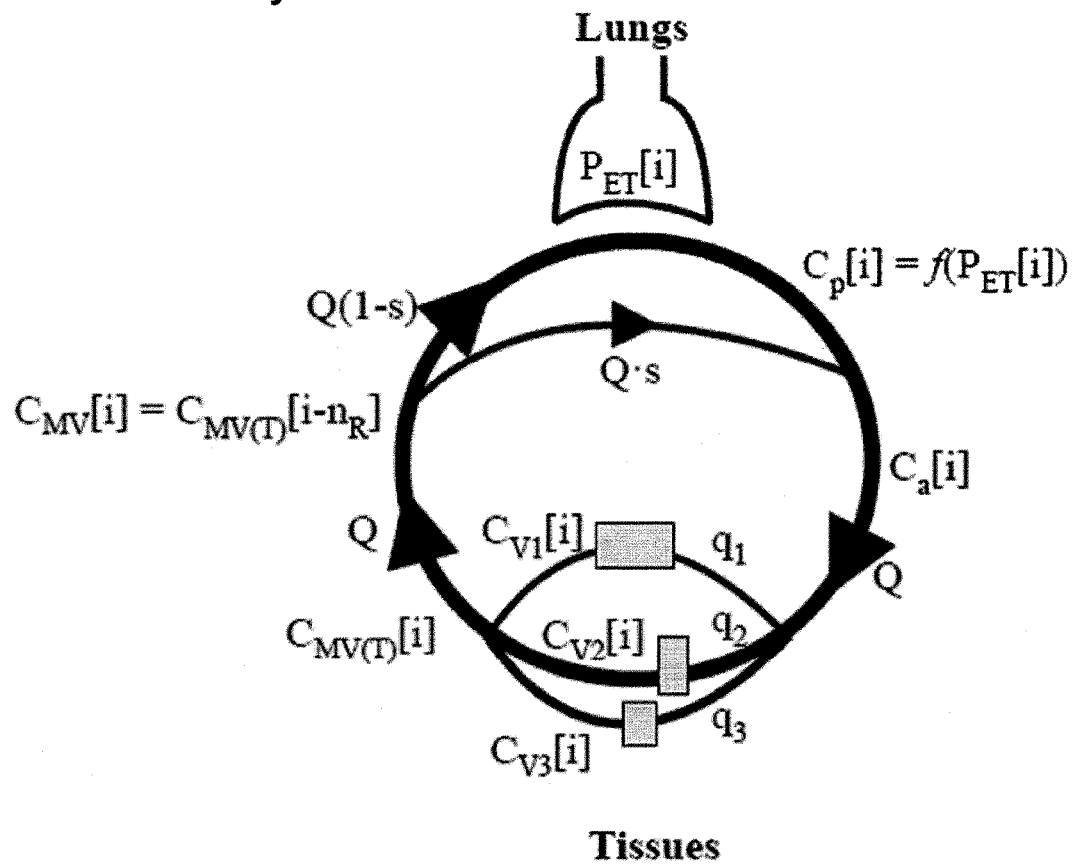

As seen FIG. 15, which shows a high level overview of the movement of blood and the exchange of gases throughout the entire system, the majority of the total blood flow (Q) passes through the pulmonary circulation. Upon transiting the pulmonary capillaries, the partial pressures of gases in the pulmonary blood equilibrate with the partial pressure of gases in the lungs ($P_{ET}[i]$)—the result is partial pressures of gases in the pulmonary end-capillary blood equal to the end-tidal partial pressures of gases in the lungs. The blood gas contents of this blood ($C_p[i]$) can then be determined from these partial pressures. The remaining fraction (s) of the total blood flow is shunted past the lungs and flows directly from the mixed-venous circulation into the arterial circulation without undergoing any gas exchange. Therefore, the gas contents of the arterial blood ($C_a[i]$) are a flow weighted average of the pulmonary end-capillary blood with gas contents equilibrated to that of the lungs, and the shunted blood with gas contents which are equal to the mixed-venous blood entering the pulmonary circulation ($C_{MV}[i]$). The arterial blood flows through the tissue capillary beds, where gases are exchanged between the blood and the tissues. There are one or more tissue capillary beds, each of which receives a fraction of the total blood flow (q) and has unique production, consumption, storage, and exchange characteristics for each gas. The gas contents in the venous blood leaving each tissue ($C_V[i]$) can be determined from these characteristics. The gas contents of the mixed-venous blood leaving the tissues ($C_{MV(T)}[i]$) are given by the flow weighted average of the gas contents in the venous blood leaving each tissue. The mixed-venous blood leaving the tissues enters the pulmonary circulation after the recirculation delay ($n_R$).

Figure 16:
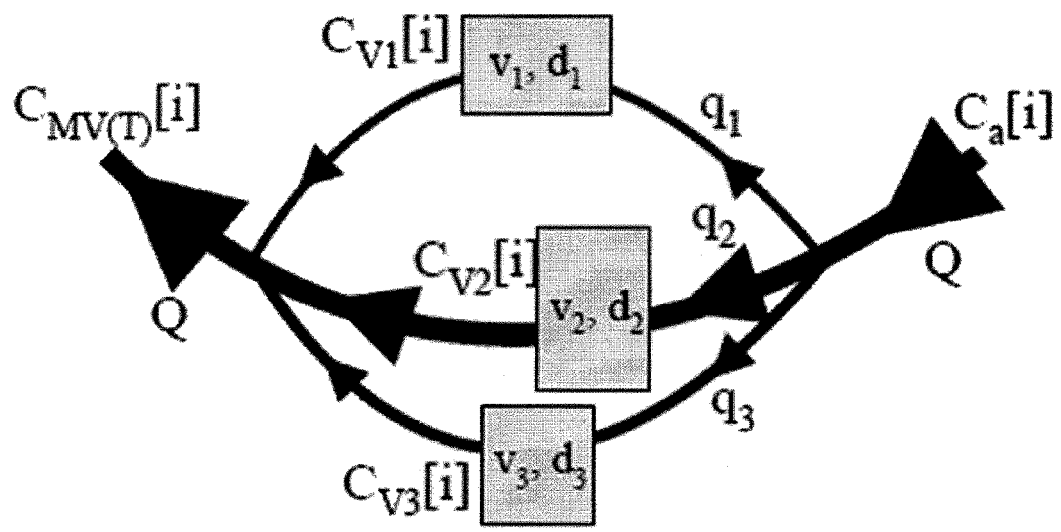

FIG. 16—The Tissues

As shown in FIG. 16, the total blood flow (Q) enters the tissue capillary beds from the arterial circulation, where the gas contents of the arterial blood ($C_a[i]$) are modified by gas exchange between the blood and the tissues. To obtain input of the gas contents of the mixed-venous blood, the flow of blood through the tissues is modelled as a system of one or more compartments where each compartment represents a single tissue or group of tissues. Each compartment is assumed to receive a fraction of the total blood flow (q) and has a unique production or consumption (v) of, and storage capacity (d) for, each gas. The content of gases in the venous blood leaving each compartment ($C_V[i]$) can be determined from the arterial inflow of gases, and the assumed production or consumption, and storage of the gas in the compartment. The blood flows leaving each compartment unite to form the mixed-venous circulation. Therefore, the gas contents of the mixed-venous blood leaving the tissues ($C_{MV(T)}[i]$) are given by the flow weighted average of the gas contents in the venous blood leaving each tissue.

Figure 17:
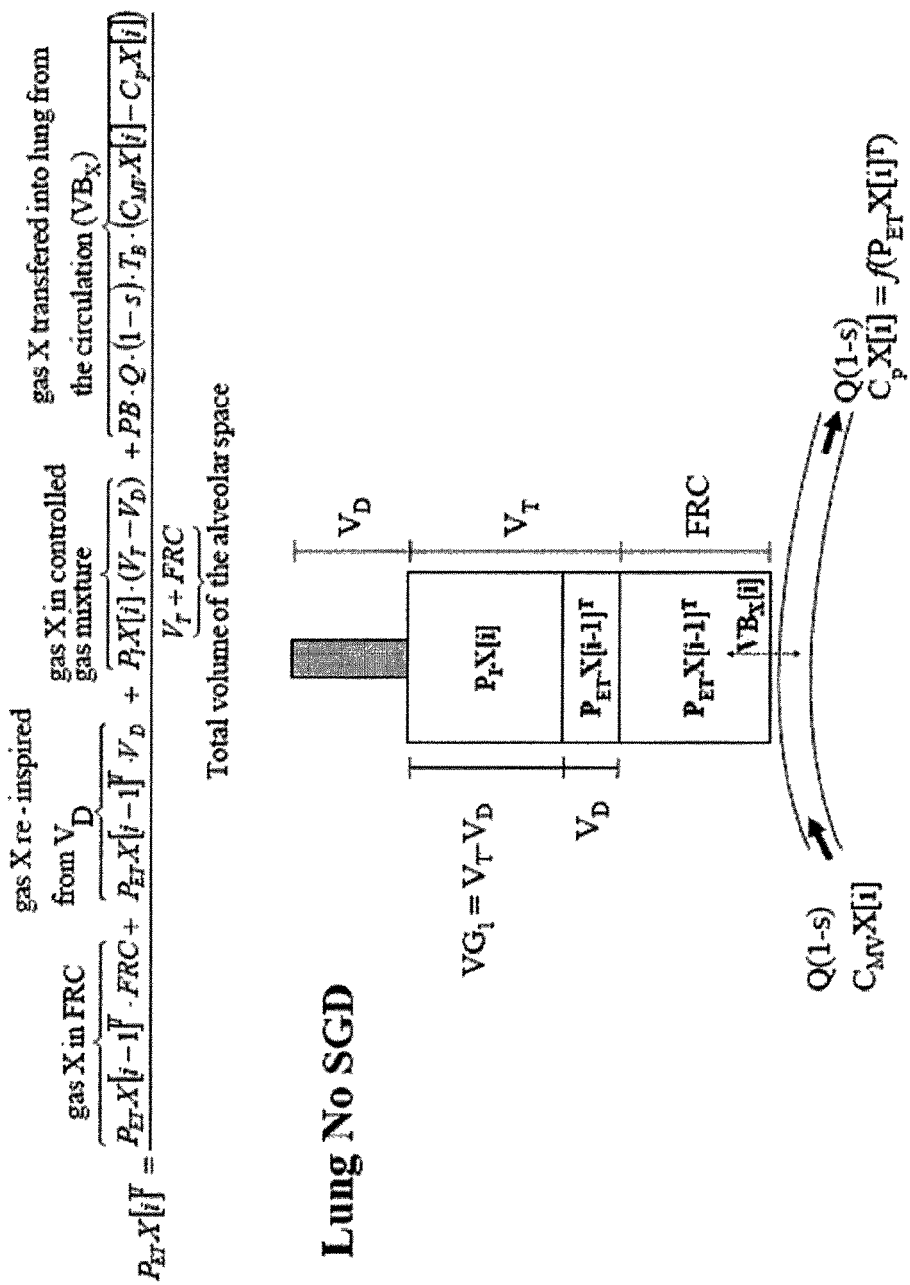

FIG. 17—the Lungs (No Sequential Rebreathing)

As shown in FIG. 17, gas enters the lungs in two ways—diffusion from the pulmonary circulation and inspiration though the airways. The pulmonary blood flow is equal to the total blood flow (Q) less the fraction (s) of the total blood flow that is shunted past the lungs. The flux rate of gas between the lungs and the pulmonary blood flow in a breath (VB[i]) is, by mass balance, the product of the pulmonary blood flow and the difference between the gas contents of the mixed-venous blood ($C_{MV}[i]$) entering the pulmonary circulation and the gas contents of the pulmonary end-capillary blood ($C_p[i]$) leaving the pulmonary circulation.

The starting volume of the lungs in any breath is given by the functional residual capacity (FRC). This is the gas left over in the lungs at the end of the previous expiration, and contains partial pressures of gases equal to the target end-tidal partial pressures from the previous breath ($P_{ET}[i-1]^T$). The first part of inspiration draws gas in the anatomical dead space ($V_D$) from the previous breath into the alveolar space. The partial pressures of gases in this volume are equal to the target end-tidal partial pressures from the previous breath. Subsequently, a volume of a controlled gas mixture ($VG_1$) with controllable partial pressures of gases ($P_I[i]$) is inspired.

Figure 18:
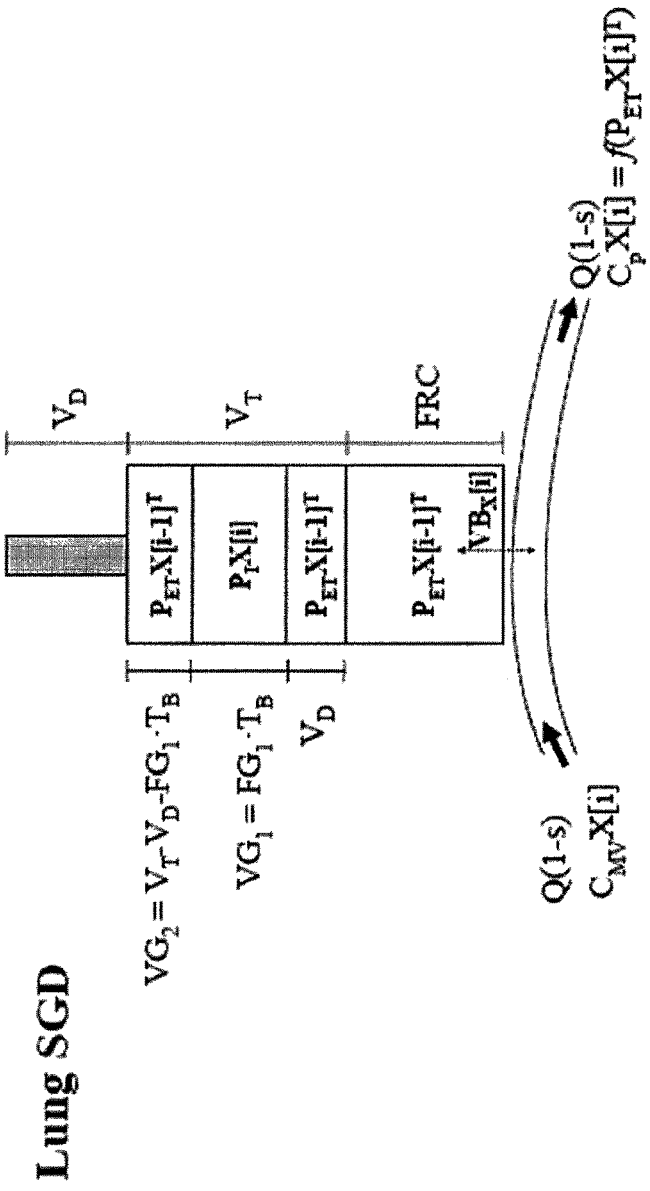

FIG. 18—the Lungs (Sequential Rebreathing)

As shown in FIG. 18, gas enters the lungs in two ways—diffusion from the pulmonary circulation and inspiration though the airways. The pulmonary blood flow is equal to the total blood flow (Q) less the fraction (s) of the total blood flow that is shunted past the lungs. The flux rate of gas between the lungs and the pulmonary blood flow in a breath (VB[i]) is, by mass balance, the product of the pulmonary blood flow and the difference between the gas contents of the mixed-venous blood ($C_{MV}[i]$) entering the pulmonary circulation and the gas contents of the pulmonary end-capillary blood ($C_p[i]$) leaving the pulmonary circulation.

The starting volume of the lungs in any breath is given by the functional residual capacity (FRC). This is the gas left over in the lungs at the end of the previous expiration, and contains partial pressures of gases equal to the target end-tidal partial pressures from the previous breath ($P_{ET}[i-1]^T$). The first part of inspiration draws gas in the anatomical dead space ($V_D$) from the previous breath into the alveolar space. The partial pressures of gases in this volume are equal to the target end-tidal partial pressures from the previous breath. Subsequently, a volume of a controlled gas mixture ($VG_1$) with controllable partial pressures of gases ($P_I[i]$) is inspired. The average volume of the controlled gas mixture inspired into the alveoli in each breath ($VG_1$) is given by the flow rate of the controlled gas mixture ($FG_1$) to the sequential gas delivery circuit (SGDC) delivered over one breath period ($T_B$). The balance of the tidal volume ($V_T$) is composed of a volume of neutral gas ($VG_2$). Where a sequential gas delivery circuit is used that provides previously expired gas as neutral gas, this volume contains partial pressures of gases equal to the target end-tidal partial pressures from the previous breath.

FIG. 19—Apparatus

Figure 19:
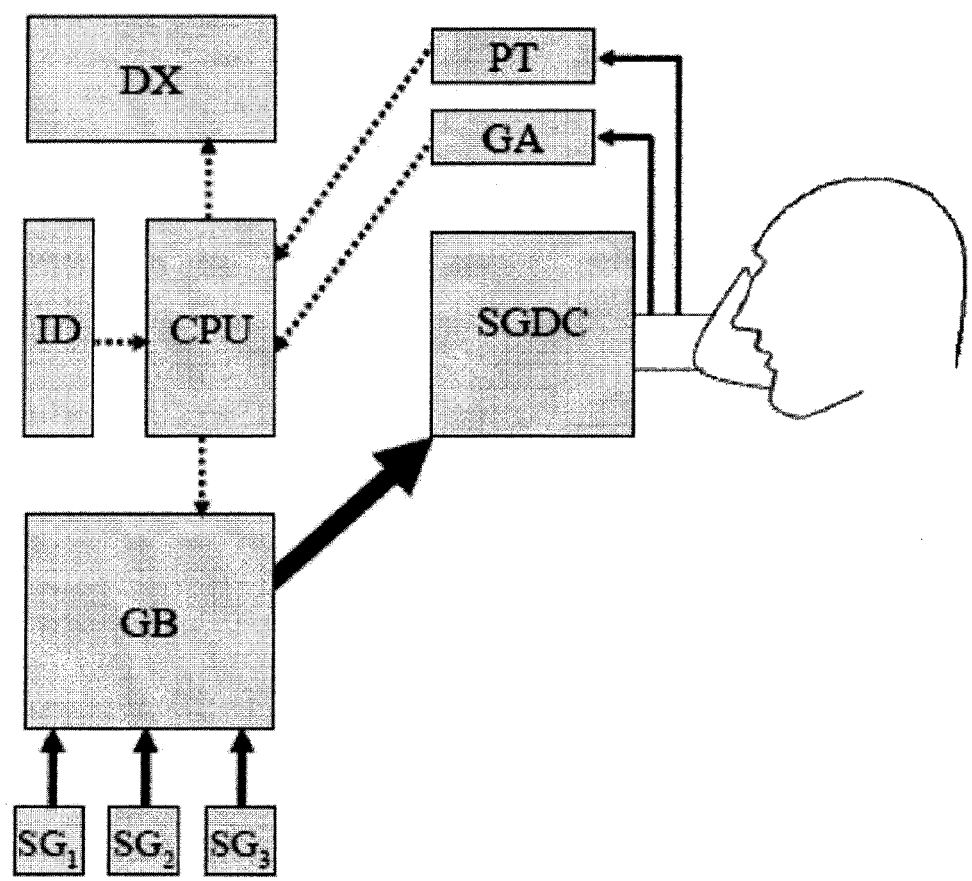

As shown in FIG. 19, according to one embodiment of an apparatus according to the invention, the apparatus consists of a gas blender (GB), a Hi-OX$_{SR}$ sequential gas delivery circuit (SGDC), gas analyzers (GA), a pressure transducer (PT), a computer (CPU), an input device (ID), and a display (DX). The gas blender contains three rapid flow controllers which are capable of delivering accurate mixes of three source gases (SG$_1$, SG$_2$, SG$_3$) to the circuit. The gases are delivered to the circuit via a gas delivery tube connecting the outlet of the gas blender to the inlet of the sequential gas delivery circuit. The gas analyzers measure the partial pressures of gases at the airway throughout the breath. The analyzers sample gas for analysis proximal to the subject's airway via a sampling catheter. A small pump is used to draw gases from the subject's airway through the gas analyzers. The pressure transducer is used for measurement of the breath period (T$_B$) and end-tidal detection, and also connected by a sampling catheter proximal to the subject's airway. The gas analyzers and pressure transducer communicate with the computer via analog or digital electrical signals. The computer runs a software implementation of the end-tidal targeting algorithm and demands the required mixtures from the blender via analog or digital electrical signals. The operator enters the target end-tidal values and subject parameters into the computer via the input device. The display shows the measured and targeted end-tidal gases.

FIG. 20—Tuning

Figure 20:
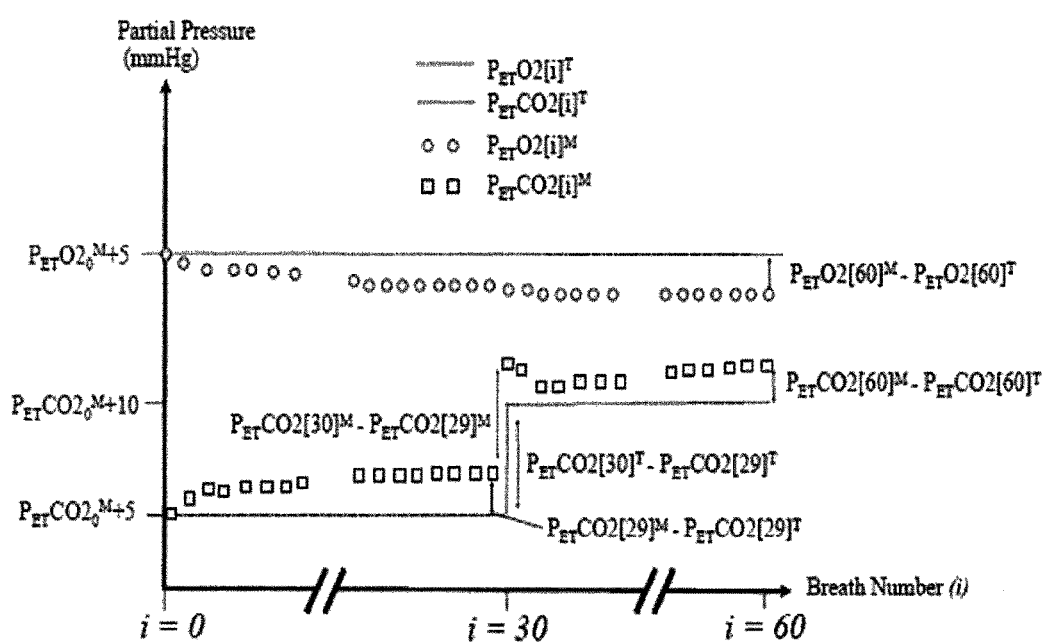

As illustrated in FIG. 20, with reference to examples of gas X (oxygen and carbon dioxide) parameters representing inputs for computation of F$_I$X can be tuned so that the measured end-tidal partial pressures of O2 (P$_{ET}$O2[i]$^M$) and the measured end-tidal partial pressures of CO2 (P$_{ET}$CO2[i]$^M$) during any sequence more closely reflect the target end-tidal partial pressures of O2 (P$_{ET}$O2[i]$^T$) and the target end-tidal partial pressures of CO2 (P$_{ET}$CO2[i]$^T$). To tune the system parameters, standardized tuning sequences are run and the measured results compared to the targets. The difference between measured end-tidal partial pressures and the target end-tidal partial pressures in the standardized tuning sequences can be used to refine the estimates of some physiological parameters.

The tuning sequence optionally sets the target end-tidal partial pressure of O2 (P$_{ET}$O2[i]$^T$) at 5 mmHg above the baseline end-tidal partial pressure of O2 (P$_{ET}$O2$_0^M$) throughout the sequence, and executes a 5 mmHg step-change in the end-tidal partial pressure of CO2 (P$_{ET}$CO2[i]$^T$) from 5 mmHg above the baseline end-tidal partial pressure of CO2 (P$_{ET}$CO2$_0^M$) to 10 mmHg above the baseline end-tidal partial pressure of CO2 in breath 30 (i=30) of the sequence.

Embodiments of Mass Balance Equations:
No SGD:

$$F_I X[i] = \frac{P_{ET} X[i]^T \cdot (FRC + V_T) - P_{ET} X[i-1]^T \cdot (FRC + V_D) - PB \cdot Q \cdot (1-s) \cdot T_B \cdot (C_{MV} X[i] - C_p X[i])}{(V_T - V_D) \cdot PB}$$

SGD:

$$F_I X[i] = \frac{(P_{ET} X[i]^T - P_{ET} X[i-1]^T) \cdot (FRC + V_T) + P_{ET} X[i-1]^T \cdot (FG_1 \cdot T_B) - PB \cdot Q \cdot (1-s) \cdot T_B \cdot (C_{MV} X[i] - C_p X[i])}{FG_1 \cdot T_B \cdot PB}$$

Abbreviations and terms are in FIG. 21.

Physiological Inputs

This section describes how to obtain measurements or estimates of all the physiological inputs required to execute a prospective end-tidal targeting sequence.

Subject Weight, Height, Age, and Sex:

Subject weight (W), height (H), age (A), and sex (G) can be obtained from a subject interview, an interview with a family member, from an attending physician, or from medical records. Weight and height can also be measured.

Bicarbonate:

The bicarbonate concentration ([HCO$_3$]) can be obtained from a blood gas measurement. If a blood gas measurement is not available or possible, it can be estimated as the middle of the normal range—24 mmol/L (9; 10).

Temperature:

Body temperature (T) can be obtained from a recent invasive or non-invasive measurement. If a measurement is not available or possible, it can be estimated as the middle of the normal range—37 C (11; 12).

Haemoglobin Concentration:

The haemoglobin concentration (Hb) can be obtained from a blood gas measurement. If a blood gas measurement is not available or possible, it can be estimated as the middle of the normal range for the subject's sex (G):

15 g/dL for males
13 g/dL for females (10; 13)

Shunt Fraction:

The intrapulmonary shunt fraction (s) can be measured using a variety of invasive and non-invasive techniques (14-17). If measurement is not available or possible, it can be estimated as the middle of the normal range—0.05 (18; 19).

Cardiac Output:

The cardiac output (Q) can be measured using a variety of invasive and non-invasive techniques (20-23). If measurement is not available or possible, it can be estimated from the subject's weight (W) according to the relationship:

$$Q = 10 \cdot (0.066 \cdot W + 1.4) \tag{24}$$

Breath Period:

The breath period (T$_B$) can be measured using a pressure transducer (PT) or flow transducer (FT) proximal to the subject's airway. Alternatively, the subject can be coached to breathe at a predetermined rate using a metronome or other prompter. If the subject is mechanically ventilated, this parameter can be determined from the ventilator settings or ventilator operator.

Recirculation Time:

The number of breaths for recirculation to occur (n$_R$) can be measured using a variety of invasive and non-invasive techniques (25-27). If measurement is not available or possible, it can be estimated from the breath period (T$_B$) and an average recirculation time (0.3 min) (28) according to the relationship:

$$n_R = 0.3 / T_B$$

Metabolic O2 Consumption:

The overall metabolic O2 consumption (VO2) can be measured using a metabolic cart. If measurement is not available or possible, it can be estimated from the subject's weight (W), height (H), age (A), and sex (G) according to the relationship:

$$VO2 = \frac{10 \cdot W + 625 \cdot H - 5 \cdot A + 5}{6.8832} \quad \text{for males} \tag{29}$$

-continued $$VO2 = \frac{10 \cdot W + 625 \cdot H - 5 \cdot A - 161}{6.8832} \text{ for females}$$

Metabolic CO2 Production:

The overall metabolic CO2 production (VCO2) can be measured using a metabolic cart. If measurement is not available or possible, it can be estimated from the overall metabolic O2 consumption (VO2) and average respiratory exchange ratio (0.8 ml CO2/ml O2) (30) according to the relationship:

$$VCO2 = 0.8 \cdot VO2$$

Functional Residual Capacity:

The functional residual capacity (FRC) can be measured using a variety of respiratory manoeuvres (31). If measurement is not available or possible, it can be estimated from the subject's height (H), age (A), and sex (G) according to the relationship:

$$FRC = (2.34 \cdot H + 0.01 \cdot A - 1.09) \cdot 1000 \text{ for males}$$

$$FRC = (2.24 \cdot H + 0.001 \cdot A - 1.00) \cdot 1000 \text{ for females} \quad (32)$$

Anatomical Dead Space:

The anatomical dead space ($V_D$) can be measured using a variety of respiratory manoeuvres (33-35). If measurement is not available or possible, it can be estimated from the subject's weight (W) and sex (G) according to the relationship:

$$V_D = 1.765 \cdot W + 32.16 \text{ for males}$$

$$V_D = 1.913 \cdot W + 21.267 \text{ for females} \quad (36)$$

Rate at which the controlled gas mixture is made available for inspiration when using a sequential gas delivery circuit (SGDC)

When using a sequential gas delivery circuit (SGDC), the rate at which the controlled gas mixture is made available for inspiration ($FG_1$) should be set so that the volume of the neutral gas inspired in each breath ($VG_2$) is greater than or equal to the anatomical dead space ($V_D$). The subject can be coached to increase their ventilation and/or the availability of the controlled gas mixture decreased until a sufficient volume of the neutral gas is observed to be inspired in each breath.

Tidal Volume:

The tidal volume ($V_T$) can be measured using a flow transducer (FT) proximal to the subject's airway. If measurement is not available or possible, in spontaneous breathers when using a sequential gas delivery circuit (SGDC), it can be estimated from the rate at which the controlled gas mixture ($G_1$) is made available for inspiration ($FG_1$), the breath period ($T_B$), and the anatomical dead space ($V_D$) according to the empirical relationship:

If $FG_1 < 15000$: $V_T = (0.75 \cdot FG_1 + 3750) \cdot T_B + V_D$ else: $V_T = FG_1 \cdot T_B + V_D$ Alternatively, the subject can be coached or trained to breathe to a defined volume using a prompter which measures the cumulative inspired volume and prompts the subject to stop inspiration when the defined volume has been inspired. If the subject is mechanically ventilated, this parameter can be determined from the ventilator settings or ventilator operator.

Target Sequence Input

The operator enters a target sequence of n breaths consisting of a target end-tidal partial pressures of O2 ($P_{ET}O2[i]^T$) and a target end-tidal partial pressure of CO2 ($P_{ET}CO2[i]^T$) for every breath (i) of the sequence.

Calculation of the Inspired Gas Composition to Induce Target End-Tidal Values

The partial pressure of O2 in the controlled gas mixture ($P_IO2[i]$) and the partial pressure of CO2 in the controlled gas mixture ($P_ICO2[i]$) required to induce the sequence of target end-tidal partial pressures of O2 ($P_{ET}O2[i]^T$) and target end-tidal partial pressures of CO2 ($P_{ET}CO2[i]^T$) can be calculated by executing the steps outlined in sections 6-15 for every breath of the sequence (i, i=1 ... n).

Calculate the O2 and CO2 Partial Pressures of Pulmonary End-Capillary Blood

When sequential rebreathing is employed (2; 37; 38), we assume that the partial pressure of O2 in pulmonary end-capillary blood ($P_pO2[i]$) is equal to the target end-tidal partial pressure of O2 ($P_{ET}O2[i]^T$), and the partial pressure of CO2 in pulmonary end-capillary blood ($P_pCO2[i]$) is equal to the target end-tidal partial pressure of CO2 ($P_{ET}CO2[i]^T$) (39).

$$P_pO2[i] = P_{ET}O2[i]^T$$

$$P_pCO2[i] = P_{ET}CO2[i]^T$$

Various other formulas have been proposed to derive blood gas partial pressures from end-tidal partial pressures. For example, see (40; 41). Any of these relationships can be used in place of the above equalities.

Calculate the pH Pulmonary End-Capillary Blood

The pH of the pulmonary end-capillary blood (pH[i]) can be calculated from the Henderson-Hasselbalch equation using the blood bicarbonate concentration ([HCO$_3$]), the blood CO2 partial pressure ($P_pCO2[i]$), and the solubility of CO2 in blood (0.03 mmol/L/mmHg) (9).

$$pH[i] = 6.1 + \log\left(\frac{[HCO_3]}{0.03 \cdot P_pCO2[i]}\right)$$

Calculate the O2 Saturation of Pulmonary End-Capillary Blood

The O2 saturation of pulmonary end-capillary blood ($S_pO2[i]$) can be calculated from experimental equations using the body temperature (T), the blood pH (pH[i]), the blood CO2 partial pressure ($P_pCO2[i]$), and the blood O2 partial pressure ($P_pO2[i]$) (42).

$$S_pO2[i] =$$
$$100 \cdot \frac{-8532.2289 \cdot z + 2121.401 \cdot z^2 - 67.073989 \cdot z^3 + z^4}{935960.87 - 31346.258 \cdot z + 2396.1674 \cdot z^2 - 67.104406 \cdot z^3 + z^4}$$

where $$z = P_pO2[i] \cdot 10^{0.024 \cdot (37-T) + 0.4 \cdot (pH[i] - 7.4) + 0.06 \cdot (\log 40 - \log P_pCO2[i])}$$

Calculate the O2 Content of Pulmonary End-Capillary Blood

The O2 content of pulmonary end-capillary blood ($C_pO2[i]$) can be calculated from the O2 saturation of the blood ($S_pO2[i]$), the blood haemoglobin concentration (Hb), the O2 carrying capacity of haemoglobin (1.36 ml/g), and the solubility of O2 in blood (0.003 ml/dL/mmHg) (43).

$$C_pO2[i] = 1.36 \cdot Hb \cdot \frac{S_pO2[i]}{100} + 0.003 \cdot P_pO2[i]$$

Alternative derivations of pH, O2 saturation, and O2 content are reviewed in detail in (44).

Calculate the CO2 Content of Pulmonary End-Capillary Blood

The CO2 content of pulmonary end-capillary blood ($C_pCO2[i]$) can be calculated from the blood haemoglobin concentration (Hb), the O2 saturation of the blood ($S_pO2[i]$), the blood pH (pH[i]), and the blood CO2 partial pressure ($P_pCO2[i]$)(45).

$$C_pCO2[i] = \left(1.0 - \frac{0.02924 \cdot Hb}{\left(2.244 - 0.422 \cdot \left(\frac{SpO2[i]}{100}\right)\right) \cdot (8.740 - pH[i])}\right) \cdot C_{pl}$$

where: $C_{pl} = 0.0301 \cdot P_pCO2[i] \cdot (1+10^{pH[i]-6.10}) \cdot 2.226$

See also (46-48) for alternative calculations of CO2 content.

Calculate the O2 and CO2 Content of Arterial Blood

The arterial blood is a mixture of the pulmonary end-capillary blood and the blood shunted past the lungs. The percentage of the cardiac output (Q) that is shunted past the lungs is given by the intrapulmonary shunt fraction (s).

The content of O2 in the arterial blood ($C_aO2[i]$) is a weighted average of the O2 content of the pulmonary end-capillary blood ($C_pO2[i]$) and the O2 content of the blood which is shunted directly from the mixed-venous circulation ($C_{MV}O2[i]$).

$C_aO2[i] = (1-s) \cdot C_pO2[i] + s \cdot C_{MV}O2[i]$

The content of CO2 in the arterial blood ($C_aCO2[i]$) is a weighted average of the CO2 content of the pulmonary end-capillary blood ($C_pCO2[i]$) and the CO2 content of the blood which is shunted directly from the mixed-venous circulation ($C_{MV}CO2[i]$).

$C_aCO2[i] = (1-s) \cdot C_pCO2 + s \cdot C_{MV}CO2[i]$

Calculate the O2 Content of the Mixed-Venous Blood

Before returning to the venous circulation, the arterial blood passes through the tissue capillary beds where O2 is consumed and exchanged. This system can be modelled as a compartmental system where each compartment (j) represents a single tissue or group of tissues. Each compartment is assigned a storage capacity for O2 ($dO2_j$). Each compartment is also modelled as being responsible for a fraction ($vo2_j$) of the overall metabolic O2 consumption (VO2), and receiving a fraction ($q_j$) of the total cardiac output (Q). The content of O2 in the venous blood leaving a compartment ($C_VO2[i]$) is equal to the content of O2 in the compartment. Assuming an O2 model with $n_{O2}$ compartments, the O2 content of the venous blood leaving each compartment can be calculated from the O2 content in the compartment during the previous breath ($C_VO2_j[i-1]$), the compartment parameters, and the period of the breath ($T_B$).

For $j = 1 ... n_{o2}$ $$C_VO2_j[i] = C_VO2_j[i-1] + \frac{100 \cdot T_B}{dO2_j} \cdot (q_j \cdot Q \cdot (C_aO2[i] - C_VO2_j[i-1]) - vo2_j \cdot VO2)$$

The values for a one compartment model ($n_{O2}=1$) are given below. The model assumes a single compartment with a storage capacity for O2 ($dO2_k$) proportional to the subjects weight (W) (49).

| j | $q_j$ | $dO2_j$ | $vo2_j$ |
|---|---|---|---|
| 1 | 1 | (1500/70) · W | 1 |

The mixed-venous O2 content leaving the tissues ($C_{MV(T)}O2[i]$) is the sum of the O2 content leaving each compartment ($C_VO2_j[i]$) weighted by the fraction of the cardiac output ($q_j$) received by the compartment.

$$C_{MV(T)}O2[i] = \sum_{j=1}^{n_{O2}} q_j \cdot C_VO2_j[i]$$

Alternatively, since the storage capacity of O2 in the tissues of the body is small, the O2 content of the mixed-venous blood leaving the tissues ($C_{MV(T)}O2[i]$) can be assumed to be equal to the arterial inflow of O2 to the tissues ($Q \cdot C_aO2[i]$) less the overall metabolic O2 consumption of the tissues (VO2) distributed over the cardiac output (Q).

$$C_{MV(T)}O2_j[i] = \frac{Q \cdot C_aO2_j[i] - VO2}{Q}$$

The O2 content of the mixed-venous blood entering the pulmonary circulation ($C_{MV}O2[i]$) is equal to the O2 content of the mixed-venous blood leaving the tissues delayed by the recirculation time ($C_{MV(T)}O2[i-n_R]$)

$C_{MV}O2[i] = C_{MV(T)}O2[i-n_R]$

Other O2 model parameters are available from (49; 50).

Calculate the CO2 Content of the Mixed-Venous Blood

Before returning to the venous circulation, the arterial blood passes through the tissue capillary beds where CO2 is produced and exchanged. This system can be modelled as a compartmental system where each compartment (k) represents a single tissue or group of tissues. Each compartment is assigned a storage capacity for CO2 ($dCO2_k$). Each compartment is also modelled as being responsible for a fraction ($vco2_k$) of the overall metabolic CO2 production (VCO2), and receiving a fraction ($q_k$) of the total cardiac output (Q). The content of CO2 in the venous blood leaving a compartment ($C_VCO2_k[i]$) is equal to the content of CO2 in the compartment. Assuming a CO2 model with $n_{CO2}$ compartments, the CO2 content of the venous blood leaving each compartment can be calculated from the CO2 content in the compartment during the previous breath ($C_VCO2_j[i-1]$), the compartment parameters, and the period of the breath ($T_B$).

For $k = 1 ... n_{CO2}$ $$C_VCO2_k[i] = C_VCO2_k[i-1] + \frac{100 \cdot T_B}{dCO2_k} \cdot (vco2_k \cdot VCO2 - q_k \cdot Q \cdot (C_VCO2_k[i-1] - C_aCO2[i]))$$

The values for a five compartment model ($n_{CO2}=5$) are given below (51). The model assumes each compartment has a storage capacity for CO2 ($dCO2_k$) proportional to the subjects weight (W).

| k | $q_k$ | $dCO2_k$ | $vco2_k$ |
|---|-------|----------|----------|
| 1 | 0.04 | (225/70) · W | 0.11 |
| 2 | 0.14 | (902/70) · W | 0.28 |
| 3 | 0.16 | (9980/70) · W | 0.17 |
| 4 | 0.15 | (113900/70) · W | 0.15 |
| 5 | 0.51 | (3310/70) · W | 0.29 |

The values for a one compartment model ($n_{CO2}=1$) are given below. The model assumes a single compartment with a storage capacity for CO2 ($dCO2_k$) proportional to the subjects weight (W). The storage capacity for the single compartment is calculated as the average of the storage capacity for each compartment of the multi-compartment model weighted by the fraction of the cardiac output assigned to the compartment.

| k | $q_k$ | $dCO2_k$ | $vco2_k$ |
|---|-------|----------|----------|
| 1 | 1 | (20505/70) · W | 1 |

The mixed-venous CO2 content leaving the tissues ($C_{MV(T)}CO2[i]$) is the sum of the CO2 content leaving each compartment ($C_VCO2_k[i]$) weighted by the fraction of the cardiac output ($q_k$) received by the compartment.

$$C_{MV(T)}CO2[i] = \sum_{k=1}^{n_{CO2}} q_k \cdot C_V CO2_k[i]$$

The CO2 content of the mixed-venous blood entering the pulmonary circulation ($C_{MV}CO2[i]$) is equal to the CO2 content of the mixed-venous blood leaving the tissues delayed by the recirculation time ($C_{MV(T)}CO2[i-n_R]$).

$$C_{MV}CO2[i]=C_{MV(T)}CO2[i-n_R]$$

Other CO2 model parameters are available from (49; 52).

Calculate PIO2 and PICO2 to Deliver with No Sequential Gas Delivery Circuit

On each inspiration, a tidal volume ($V_T$) of gas is inspired into the alveoli. When the subject is not connected to a sequential gas delivery circuit, gas is inspired in the following order: a) the gas in the anatomical dead space ($V_D$) is re-inspired with a partial pressure of O2 equal to the target end-tidal partial pressure of O2 from the previous breath ($P_{ET}O2[i-1]^T$) and a partial pressure of CO2 equal to the target end-tidal partial pressure of CO2 from the previous breath ($P_{ET}CO2[i-1]^T$); b) a volume of controlled gas mixture ($VG_1$) with controllable partial pressure of O2 ($P_IO2[i]$) and controllable partial pressure of CO2 ($P_ICO2[i]$). This inspired gas mixes with the volume of gas in the functional residual capacity (FRC) with a partial pressure of O2 and CO2 equal to the target end-tidal partial pressures from the previous breath.

A volume of O2 is transferred between the alveolar space and the pulmonary circulation ($VB_{O2}[i]$). The rate of O2 transfer between the alveolar space and the pulmonary circulation depends on the product of the cardiac output (Q) less the intrapulmonary shunt fraction (s), and the difference between the mixed-venous O2 content entering the pulmonary circulation ($C_{MV}O2[i]$) and the pulmonary end-capillary O2 content ($C_pO2[i]$) leaving the pulmonary circulation. This transfer occurs over the breath period ($T_B$).

$$VB_{O2}[i]=Q\cdot(1-s)\cdot T_B\cdot(C_{MV}O2[i]-C_pO2[i])$$

A volume of CO2 is transferred between the alveolar space and the pulmonary circulation ($VB_{CO2}[i]$). The rate of CO2 transfer between the alveolar space and the pulmonary circulation depends on the product of the cardiac output (Q) less the intrapulmonary shunt fraction (s), and the difference between the mixed-venous CO2 content entering the pulmonary circulation ($C_{MV}CO2[i]$) and the pulmonary end-capillary CO2 content ($C_pCO2[i]$) leaving the pulmonary circulation. This transfer occurs over the breath period ($T_B$).

$$VB_{CO2}[i]=Q\cdot(1-s)\cdot T_B\cdot(C_{MV}CO2[i]-C_pCO2[i])$$

The average volume of the controlled gas mixture inspired into the alveoli in each breath ($VG_1$) is given by the tidal volume ($V_T$) less the anatomical dead space ($V_D$).

$$VG_1=V_T-V_D$$

The end-tidal partial pressure O2 ($P_{ET}O2[i]^T$) is simply the total volume of O2 in the alveolar space, divided by the total volume of the alveolar space. The end-tidal partial pressure CO2 ($P_{ET}CO2[i]^T$) is simply the total volume of CO2 in the alveolar space, divided by the total volume of the alveolar space.

$$P_{ET}O2[i]^T = \frac{\left\{\begin{array}{c}\overbrace{P_{ET}O2[i-1]^T\cdot FRC}^{O2\ in\ FRC}+\overbrace{P_{ET}O2[i-1]^T\cdot V_D}^{O2\ re-inspired\ from\ V_D}+\\ \underbrace{P_IO2[i]\cdot(V_T-V_D)}_{O2\ in\ controlled\ gas\ mixture}+\underbrace{PB\cdot Q\cdot(1-s)\cdot T_B\cdot(C_{MV}O2[i]-C_pO2[i])}_{O2\ transfered\ into\ lung\ from\ the\ circulation\ (VB_{O2})}\end{array}\right\}}{\underbrace{V_T+FRC}_{Total\ volume\ of\ the\ alveolar\ space}}$$

$$P_{ET}CO2[i]^T = \frac{\left\{\begin{array}{c}\overbrace{P_{ET}CO2[i-1]^T\cdot FRC}^{CO2\ in\ FRC}+\overbrace{P_{ET}CO2[i-1]^T\cdot V_D}^{CO2\ re-inspired\ from\ V_D}+\\ \underbrace{P_ICO2[i]\cdot(V_T-V_D)}_{CO2\ in\ controlled\ gas\ mixture}+\underbrace{PB\cdot Q\cdot(1-s)\cdot T_B\cdot(C_{MV}CO2[i]-C_pCO2[i])}_{CO2\ transfered\ into\ lung\ from\ the\ circulation\ (VB_{CO2})}\end{array}\right\}}{\underbrace{V_T+FRC}_{Total\ volume\ of\ the\ alveolar\ space}}$$

Since all of these volumes and partial pressures are either known, or can be estimated, the partial pressure of O2 in the controlled gas mixture ($P_IO2[i]$) and the partial pressure of CO2 in the controlled gas mixture ($P_ICO2[i]$) can be set to induce target end-tidal partial pressures.

In some cases, some of the terms (braced terms in the numerator of the above equations) contributing to the target end-tidal partial pressure of O2 ($P_{ET}O2[i]^T$) or the target end-tidal partial pressure of CO2 ($P_{ET}CO2[i]^T$) may be neglected. For example, in most cases, the O2 or CO2 re-inspired from the anatomical dead space ($V_D$) is small compared to the O2 or CO2 in the other volumes that contribute to the end-tidal partial pressures. In a case where the volume of $O_2$ or $CO_2$ in the controlled gas mixture is very large, for example when trying to induce a large increase in the target end-tidal partial pressures, the $O_2$ or $CO_2$ transferred into the lung from the circulation may be comparatively small and neglected. Neglecting any terms of the mass balance equations will decrease computational complexity at the expense of the accuracy of the induced end-tidal partial pressures of gases.

After re-arranging the above equations for the partial pressure of O2 in the controlled gas mixture and the partial pressure of CO2 in the controlled gas mixture, simplification, and grouping of terms:

$$P_I O2[i] = \frac{P_{ET}O2[i]^T \cdot (FRC + V_T) - P_{ET}O2[i-1]^T \cdot (FRC + V_D) - PB \cdot Q \cdot (1-s) \cdot T_B \cdot (C_{MV}O2[i] - C_p O2[i])}{V_T - V_D}$$

$$P_I CO2[i] = \frac{P_{ET}CO2[i]^T \cdot (FRC + V_T) - P_{ET}CO2[i-1]^T \cdot (FRC + V_D) - PB \cdot Q \cdot (1-s) \cdot T_B \cdot (C_{MV}CO2[i] - C_p CO2[i])}{V_T - V_D}$$

These equations can be used to calculate the partial pressure of O2 in the controlled gas mixture ($P_I O2[i]$) and the partial pressure of CO2 in the controlled gas mixture ($P_I CO2[i]$) required to induce a target end-tidal partial pressure of O2 ($P_{ET}O2[i]^T$) and target end-tidal partial pressure of CO2 ($P_{ET}CO2[i]^T$) where the target end-tidal partial pressure of O2 from the previous breath ($P_{ET}O2[i-1]^T$), the target end-tidal partial pressure of CO2 from the previous breath ($P_{ET}CO2[i-1]^T$), the functional residual capacity (FRC), the anatomical dead space ($V_D$), tidal volume ($V_T$), the breath period ($T_B$), cardiac output (Q), intrapulmonary shunt fraction (s), mixed-venous content of O2 entering the pulmonary circulation ($C_{MV}O2[i]$), mixed-venous content of CO2 entering the pulmonary circulation ($C_{MV}CO2[i]$), pulmonary end-capillary content of O2 ($C_p O2[i]$), and pulmonary end-capillary content of CO2 ($C_p CO2[i]$) are either known, calculated, estimated, measured, or predicted.

Notice that the partial pressure of O2 in the controlled gas mixture ($P_I O2[i]$) and the partial pressure of CO2 in the controlled gas mixture ($P_I CO2[i]$) required to induce a target end-tidal partial pressure of O2 ($P_{ET}O2[i]^T$) or a target end-tidal partial pressure of CO2 ($P_{ET}CO2[i]^T$) depends strongly on the tidal volume ($V_T$), anatomical dead space ($V_D$), and the functional residual capacity (FRC).

It is often useful in practise to maintain the end-tidal partial pressures of gases steady for a predefined number of breaths or period of time. This is a special case of inducing target end-tidal partial pressures of gases where the target end-tidal partial pressure of a gas in a breath is equal to the target end-tidal partial pressure of said gas from the previous breath.

$$P_{ET}O2[i]^T = P_{ET}O2[i-1]^T \text{ OR}$$

$$P_{ET}CO2[i]^T = P_{ET}CO2[i-1]^T$$

Herein, the above general equations for calculating the composition of the controlled gas mixture reduce to the following:

$$P_I O2[i] = \frac{P_{ET}O2[i]^T \cdot (V_T - V_D) - PB \cdot Q \cdot (1-s) \cdot T_B \cdot (C_{MV}O2[i] - C_p O2[i])}{V_T - V_D}$$

-continued $$P_I CO2[i] = \frac{P_{ET}CO2[i]^T \cdot (V_T - V_D) - PB \cdot Q \cdot (1-s) \cdot T_B \cdot (C_{MV}CO2[i] - C_p CO2[i])}{V_T - V_D}$$

Notice, these equations still require the estimation, measurement, or determination of many of the subject's ventilatory or pulmonary parameters, namely tidal volume ($V_T$), functional residual capacity (FRC), breath period ($T_B$), and anatomical dead space ($V_D$). Therefore, in the absence of sequential rebreathing, the calculation of the partial pressure of $O_2$ in the controlled gas mixture ($P_I O2[i]$) and the partial pressure of CO2 in the controlled gas mixture ($P_I CO2[i]$) required to induce a target end-tidal partial pressure of $O_2$ ($P_{ET}O2[i]^T$) and a target end-tidal partial pressure of $CO_2$ ($P_{ET}CO2[i]^T$) is highly dependant on the subjects ventilatory and pulmonary parameters. However, some of these parameters, namely functional residual capacity (FRC) and the anatomical dead space ($V_D$), can be measured or estimated prior to execution of the targeting sequence, and can be reasonably assumed not to change over the course of the experiment. Other parameters, namely tidal volume ($V_T$) and breath period ($T_B$), while normally highly variable, are very well controlled and stable in mechanically ventilated subjects.

This method, therefore, is optional, especially where a simpler approach is preferred, and the subject's ventilation can be reasonably controlled or predicted.

It will be recognized that the volumes and partial pressures required to calculate the partial pressure of $O_2$ in the controlled gas mixture ($P_I O2[i]$) and the partial pressure of $CO_2$ in the controlled gas mixture ($P_I CO2[i]$) may need to be corrected for differences in temperature or presence of water vapour between the lung and the conditions under which they are measured, estimated, or delivered. The corrections applied will depend on the conditions under which these volumes and partial pressures are measured, estimated, or delivered. All volumes and partial pressures should be corrected to body temperature and pressure saturated conditions. A person skilled in the art will be comfortable with these corrections.

A person skilled in the art will also recognize the equivalence between partial pressures and fractional concentrations. Any terms expressed as partial pressures can be converted to fractional concentrations and vice-versa. For example, the partial pressure of O2 in the controlled gas mixture ($P_I O2[i]$) and the partial pressure of CO2 in the controlled gas mixture ($P_I CO2[i]$) may be converted a fractional concentration of O2 in the controlled gas mixture ($F_I O2[i]$) and a fractional concentration of CO2 in the controlled gas mixture ($F_I CO2[i]$).

$$F_I O2[i] = \frac{P_I O2[i]}{PB}$$

$$F_I CO2[i] = \frac{P_I CO_2[i]}{PB}$$

Calculate PIO2 and PICO2 to Deliver to a Sequential Gas Delivery Circuit

On each inspiration, a tidal volume ($V_T$) of gas is inspired into the alveoli. When the subject is connected to a sequential gas delivery circuit (SGDC) that collects previously expired gas in a reservoir for later inspiration as neutral gas (ex. Hi-Ox$_{SR}$), gas is inspired in the following order: a) the gas in the anatomical dead space ($V_D$) is re-inspired with a partial pressure of O2 equal to the target end-tidal partial pressure of O2 from the previous breath ($P_{ET}O2[i-1]^T$) and a partial pressure of CO2 equal to the target end-tidal partial pressure of $CO_2$ from the previous breath ($P_{ET}CO2[i-1]^T$); b) a volume of controlled gas mixture ($VG_1$) with controllable partial pressure of $O_2$ ($P_IO2[i]$) and controllable partial pressure of CO2 ($P_ICO2[i]$); c) a volume of neutral gas ($VG_2$) with a partial pressure of O2 and CO2 equal to the target end-tidal partial pressures from the previous breath. This inspired gas mixes with the volume of gas in the functional residual capacity (FRC) with a partial pressure of O2 and CO2 equal to the target end-tidal partial pressures from the previous breath.

A volume of O2 is transferred between the alveolar space and the pulmonary circulation ($VB_{O2}[i]$). The rate of O2 transfer between the alveolar space and the pulmonary circulation depends on the product of the cardiac output (Q) trolled gas mixture inspired into the alveoli in each breath ($VG_1$) is given by the rate at which the controlled gas mixture is made available for inspiration ($FG_1$) delivered over a single breath period ($T_B$):

$$VG_1 = FG_1 \cdot T_B$$

The average volume of neutral gas that is inspired into the alveoli in each breath is given by the tidal volume ($V_T$) less the volume of inspired controlled gas mixture ($VG_1$) and the volume of gas that remains in the anatomical dead space ($V_D$):

$$VG_2 = V_T - V_D - FG_1 \cdot T_B$$

The end-tidal partial pressure O2 ($P_{ET}O2[i]^T$) is simply the total volume of O2 in the alveolar space, divided by the total volume of the alveolar space. The end-tidal partial pressure CO2 ($P_{ET}CO2[i]^T$) is simply the total volume of CO2 in the alveolar space, divided by the total volume of the alveolar space.

$$P_{ET}O2[i]^T = \frac{\left(\begin{array}{c}\overbrace{P_{ET}O2[i-1]^T \cdot FRC}^{O2 \text{ in FRC}} + \overbrace{P_{ET}O2[i-1]^T \cdot V_D}^{O2 \text{ re-inspired from } V_D} + \\ \underbrace{P_IO2[i] \cdot (FG_1 \cdot T_B)}_{O2 \text{ in controlled gas mixture}} + \underbrace{P_{ET}O2[i-1]^T \cdot (V_T - V_D - FG_1 \cdot T_B)}_{O2 \text{ in neutral gas}} + \\ \underbrace{PB \cdot Q \cdot (1-s) \cdot T_B \cdot (C_{MV}O2[i] - C_pO2[i])}_{O2 \text{ transferred into lung from the circulation}(VB_{O2})}\end{array}\right)}{\underbrace{V_T + FRC}_{\text{Total volume of the alveolar space}}}$$

$$P_{ET}CO2[i]^T = \frac{\left(\begin{array}{c}\overbrace{P_{ET}CO2[i-1]^T \cdot FRC}^{CO2 \text{ in FRC}} + \overbrace{P_{ET}CO2[i-1]^T \cdot V_D}^{CO2 \text{ re-inspired from } V_D} + \\ \underbrace{P_ICO2[i] \cdot (FG_1 \cdot T_B)}_{CO2 \text{ in controlled gas mixture}} + \underbrace{P_{ET}CO2[i-1]^T \cdot (V_T - V_D - FG_1 \cdot T_B)}_{CO2 \text{ in neutral gas}} + \\ \underbrace{PB \cdot Q \cdot (1-s) \cdot T_B \cdot (C_{MV}CO2[i] - C_pCO2[i])}_{CO2 \text{ transferred into lung from the circulation}(VB_{O2})}\end{array}\right)}{(\underbrace{V_T + FRC}_{\text{Total volume of the alveolar space}})}$$

less the intrapulmonary shunt fraction (s), and the difference between the mixed-venous O2 content entering the pulmonary circulation ($C_{MV}O2[i]$) and the pulmonary end-capillary O2 content ($C_pO2[i]$) leaving the pulmonary circulation. This transfer occurs over the breath period ($T_B$).

$$VB_{O2}[i] = Q \cdot (1-s) \cdot T_B \cdot (C_{MV}O2[i] - C_pO2[i])$$

A volume of CO2 is transferred between the alveolar space and the pulmonary circulation ($VB_{CO2}[i]$). The rate of CO2 transfer between the alveolar space and the pulmonary circulation depends on the product of the cardiac output (Q) less the intrapulmonary shunt fraction (s), and the difference between the mixed-venous CO2 content entering the pulmonary circulation ($C_{MV}CO2[i]$) and the pulmonary end-capillary CO2 content ($C_pCO2[i]$) leaving the pulmonary circulation. This transfer occurs over the breath period ($T_B$).

$$VB_{CO2}[i] = Q \cdot (1-s) \cdot T_B \cdot (C_{MV}CO2[i] - C_pCO2[i])$$

Assuming a neutral gas at least fills the subject's anatomical dead space ($V_D$), the average volume of the con- Since all of these volumes and partial pressures are either known, or can be estimated, the partial pressure of O2 in the controlled gas mixture ($P_IO2[i]$) and the partial pressure of CO2 in the controlled gas mixture ($P_ICO2[i]$) can be set to induce target end-tidal partial pressures.

In some cases, some of the terms (braced terms in the numerator of the above equations) contributing to the target end-tidal partial pressure of O2 ($P_{ET}O2[i]^T$) or the target end-tidal partial pressure of CO2 ($P_{ET}CO2[i]^T$) may be neglected. For example, in most cases, the $O_2$ or $CO_2$ re-inspired from the anatomical dead space ($V_D$) is small compared to the $O_2$ or $CO_2$ in the other volumes that contribute to the end-tidal partial pressures. In the case where the volume of O2 or CO2 in the controlled gas mixture is very large, for example when trying to induce a large increase in the target end-tidal partial pressures, the O2 or CO2 transferred into the lung from the circulation may be comparatively small and neglected. Neglecting any terms of the mass balance equations will decrease computational complexity at the expense of the accuracy of the induced end-tidal partial pressures of gases.

After re-arranging the above equations for the partial pressure of O2 in the controlled gas mixture and the partial pressure of CO2 in the controlled gas mixture, simplification, and grouping of terms:

$$P_I O2[i] = \frac{\begin{array}{c}(P_{ET}O2[i]^T - P_{ET}O2[i-1]^T) \cdot (FRC + V_T) + \\ P_{ET}O2[i-1]^T \cdot (FG_1 \cdot T_B) - PB \cdot \\ Q \cdot (1-s) \cdot T_B \cdot (C_{MV}O2[i] - C_p O2[i])\end{array}}{FG_1 \cdot T_B}$$

$$P_I CO2[i] = \frac{\begin{array}{c}(P_{ET}CO2[i]^T - P_{ET}CO2[i-1]^T) \cdot (FRC + V_T) + \\ P_{ET}CO2[i-1]^T \cdot (FG_1 \cdot T_B) - PB \cdot \\ Q \cdot (1-s) \cdot T_B \cdot (C_{MV}CO2[i] - C_p CO2[i])\end{array}}{FG_1 \cdot T_B}$$

The above equations can be used to calculate the partial pressure of O2 in the controlled gas mixture ($P_I O2[i]$) and the partial pressure of CO2 in the controlled gas mixture ($P_I CO2[i]$) required to induce a target end-tidal target partial pressure of O2 ($P_{ET}O2[i]^T$) and a target end-tidal partial pressure of CO2 ($P_{ET}CO2[i]^T$) where the target end-tidal partial pressure of O2 from the previous breath ($P_{ET}O2[i-1]^T$), the target end-tidal partial pressure of CO2 from the previous breath ($P_{ET}CO2[i-1]^T$), the functional residual capacity (FRC), tidal volume ($V_T$), rate at which the controlled gas mixture is made available for inspiration ($FG_1$), the breath period ($T_B$), cardiac output (Q), intrapulmonary shunt fraction (s), recirculation time ($n_R$), mixed-venous content of O2 entering the pulmonary circulation ($C_{MV}O2[i]$), mixed-venous content of CO2 entering the pulmonary circulation ($C_{MV}CO2[i]$), pulmonary end-capillary content of O2 ($C_p O2[i]$), and pulmonary end-capillary content of CO2 ($C_p CO2[i]$) are either known, calculated, estimated, measured, or predicted.

Notice that where this form sequential rebreathing is employed, the anatomical dead space ($V_D$) does not factor into the above equations and end-tidal targeting is independent of its measurement or estimation. Notice also that the tidal volume ($V_T$) appears only in summation with the functional residual capacity (FRC). Since the tidal volume is, in general, small compared to the functional residual capacity ($V_T \leq 0.1 \cdot FRC$), errors in measurement or estimation of the tidal volume have little effect on inducing target end-tidal partial pressures of gases. In fact, the above equations can be used with the tidal volume term omitted completely with little effect on results.

It is often useful in practise to maintain the end-tidal partial pressures of gases steady for a predefined number of breaths or period of time. This is a special case of inducing target end-tidal partial pressures of gases where the target end-tidal partial pressure of a gas in a breath is equal to the target end-tidal partial pressure of said gas from the previous breath.

$$P_{ET}O2[i]^T = P_{ET}O2[i-1]^T \text{ OR}$$

$$P_{ET}CO2[i]^T = P_{ET}CO2[i-1]^T$$

Herein, the above general equations for calculating the composition of the controlled gas mixture reduce to the following:

$$P_I O2[i] = \frac{P_{ET}O2[i]^T \cdot FG_1 - PB \cdot Q \cdot (1-s) \cdot (C_{MV}O2[i] - C_p O2[i])}{FG_1}$$

$$P_I CO2[i] = \frac{P_{ET}CO2[i]^T \cdot FG_1 - PB \cdot Q \cdot (1-s) \cdot (C_{MV}CO2[i] - C_p CO2[i])}{FG_1}$$

Notice, these equations do not require the estimation, measurement, or determination of any of the subject's ventilatory or pulmonary parameters, namely, tidal volume ($V_T$), functional residual capacity (FRC), breath period ($T_B$), or anatomical dead space ($V_D$). The reduced or eliminated sensitivity of the equations to the subject's ventilatory parameters makes this method useful in practise with spontaneously breathing subjects. It is, however, not limited to spontaneously breathing subjects, and may also be used in mechanically ventilated subjects.

A person skilled in the art will recognize that the volumes and partial pressures required to calculate the partial pressure of O2 in the controlled gas mixture ($P_I O2[i]$) and the partial pressure of CO2 in the controlled gas mixture ($P_I CO2[i]$) may need to be corrected for differences in temperature or presence of water vapour between the lung and the conditions under which they are measured, estimated, or delivered. The corrections applied will depend on the conditions under which these volumes and partial pressures are measured, estimated, or delivered. All volumes and partial pressures should be corrected to body temperature and pressure saturated conditions. A person skilled in the art will be comfortable with these corrections.

A person skilled in the art will also recognize the equivalence between partial pressures and fractional concentrations. Any terms expressed as partial pressures can be converted to fractional concentrations and vice-versa. For example, the partial pressure of O2 in the controlled gas mixture ($P_I O2[i]$) and the partial pressure of CO2 in the controlled gas mixture ($P_I CO2[i]$) may be converted a fractional concentration of O2 in the controlled gas mixture ($F_I O2[i]$) and a fractional concentration of CO2 in the controlled gas mixture ($F_I CO2[i]$).

$$F_I O2[i] = \frac{P_I O2[i]}{PB}$$

$$F_I CO2[i] = \frac{P_I CO2[i]}{PB}$$

Determine if Targets are Logistically Feasible

In practise, many different implementations of gas delivery devices and sequential gas delivery circuits may be used. In general, it is logistically feasible to induce the target end-tidal partial pressures for the current breath ($P_{ET}O2[i]^T$, $P_{ET}CO2[i]^T$) if:

1) The required partial pressures of gases in the controlled gas mixture are physically realizable:

a) $0 \leq P_I O2[i] \leq PB$ b) $0 \leq P_I CO2[i] \leq PB$ c) $P_I O2[i] + P_I CO2[i] \leq PB$ 2) The gas delivery device is capable of delivering a controlled mixture of the desired composition at the required flow rate Where sequential rebreathing is carried out with a Hi-Ox$_{SR}$ sequential gas delivery circuit and a gas blender:

Assuming $n_{SG}$ source gases ($SG_1 \ldots SG_{n_G}$) are blended to deliver the required mixture to the Hi-Ox$_{SR}$ sequential gas delivery circuit (SGDC). Each gas (m) contains a known fractional concentration of O2 ($fo2_m$) and a known fractional concentration of CO2 ($fco2_m$). The flow rate of each gas ($FSG_m[i]$) required to deliver the total desired flow rate of the controlled gas ($FG_1$) with the required partial pressure of O2 ($P_I O2[i]$) and the required partial pressure of CO2 ($P_I CO2[i]$) can be determined by solving the following set of equations:

$$\sum_{m=1}^{n_{SG}} FSG_m[i] = FG_1$$

$$\sum_{m=1}^{n_{SG}} fo2_m \cdot FSG_m[i] = \frac{P_I O2[i]}{PB} \cdot FG_1$$

$$\sum_{m=1}^{n_{SG}} fco2_m \cdot FSG_m[i] = \frac{P_I CO2[i]}{PB} \cdot FG_1$$

The target end-tidal partial pressures for the current breath ($P_{ET}O2[i]^T$, $P_{ET}CO2[i]^T$) are logistically feasible if:
1) $0 \leq P_I O2[i] \leq PB$
2) $0 \leq P_I CO2[i] \leq PB$
3) $P_I O2[i] + P_I CO2[i] \leq PB$
4) There exists a solution to the above system of equations, and
5) $FSG_m[i] \geq 0 \forall m$
6) The gas blender is capable of delivering a controlled mixture of the desired composition at the required flow rate It is therefore required that $n_{SG} \geq 3$. It is computationally optimal to have $n_{SG} = 3$.

One possible set of gases is:
$SG_1$: $fco2_1=0$, $fo2_1=1$
$SG_2$: $fco2_2=1$, $fo2_2=0$
$SG_3$: $fco2_3=0$, $fo2_3=0$ It may enhance the safety of the system to use gases with a minimal concentration of O2 and maximum concentration of CO2. In this case, a possible set of gases is:
$SG_1$: $fco2_1=0$, $fo2_1=0.1$
$SG_2$: $fco2_2=0.4$, $fo2_2=0.1$
$SG_3$: $fco2_3=0$, $fo2_3=1$ The balance of the source gases when not entirely composed of O2 and CO2 can be made up of any gas or combination of gases, which may vary depending on the context. The balance of the source gases is most often made up of N2 because it is physiologically inert.

Adjusting parameters to make logistically infeasible targets logistically feasible:

It may occur that inducing a target end-tidal partial pressure of O2 ($P_{ET}O2[i]^T$) or a target end-tidal partial pressure of CO2 ($P_{ET}CO2[i]^T$) in a given breath is not logistically feasible. This may occur because the partial pressure of O2 in the controlled gas mixture ($P_I O2[i]$) or the partial pressure of CO2 in the controlled gas mixture ($P_I CO2[i]$) required to induce the target end-tidal partial pressure of O2 or the target end-tidal partial pressure of CO2 is either not physically realizable, or there does not exist a blend of the current source gases ($SG_1 \ldots SG_{n_G}$) resulting in the required partial pressure of O2 in the controlled gas mixture and the required partial pressure of CO2 in the controlled gas mixture. If the composition of the controlled gas mixture is not physically realizable for a given set of targets, the targets may be modified and/or the rate at which the controlled gas mixture is made available to the circuit ($FG_1$) modified, or where applicable, the tidal volume ($V_T$) modified, until the composition is physically realizable. If the composition of the controlled gas mixture is physically realizable for a given set of targets, but no combination of the source gases results in the required composition, the targets may be modified and/or the rate at which the controlled gas mixture is made available to the circuit modified, or where applicable, the tidal volume ($V_T$) modified, and/or different source gases used.

If $P_I O2[i] < 0$—The target end-tidal partial pressure of O2 ($P_{ET}O2[i]^T$) is not logistically feasible because the partial pressure of O2 in the controlled gas mixture ($P_I O2[i]$) required to induce the target end-tidal partial pressure of O2 is not physically realizable. To make induction of the target logistically feasible, increase the target end-tidal partial pressure of O2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_I O2[i] > PB$—The target end-tidal partial pressure of O2 ($P_{ET}O2[i]^T$) is not logistically feasible because the partial pressure of O2 in the controlled gas mixture ($P_I O2[i]$) required to induce the target end-tidal partial pressure of O2 is not physically realizable. To make induction of the target logistically feasible, decrease the target end-tidal partial pressure of O2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_I CO2[i] < 0$—The target end-tidal partial pressure of CO2 ($P_{ET}CO2[i]^T$) is not logistically feasible because the partial pressure of CO2 in the controlled gas mixture ($P_I CO2[i]$) required to induce the target end-tidal partial pressure of CO2 is not physically realizable. To make induction of the target logistically feasible, decrease the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_I CO2[i] > PB$—The target end-tidal partial pressure of CO2 ($P_{ET}CO2[i]^T$) is not logistically feasible because the partial pressure of CO2 in the controlled gas mixture ($P_I CO2[i]$) required to induce the target end-tidal partial pressure of CO2 is not physically realizable. To make induction of the target logistically feasible, decrease the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_I O2[i] + P_I CO2[i] > PB$—The combination of the target end-tidal partial pressure of O2 ($P_{ET}O2[i]^T$) and the target end-tidal partial pressure of CO2 ($P_{ET}CO2[i]^T$) is not logistically feasible because the combination of the partial pressure of O2 in the controlled gas mixture ($P_I O2[i]$) and the partial pressure of CO2 in the controlled gas mixture ($P_I CO2[i]$) required to induce the targets is not physically realizable. To make induction of the targets logistically feasible, decrease the target end-tidal partial pressure of O2 and/or the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If there does not exist a solution to the above system of equations, or there exists a solution for which $FSG_m[i]<0$ for any m, then the current source gases ($SG_1 \ldots SG_{n_G}$) cannot be blended to create the controlled gas mixture. Different source gases must be used to induce the end-tidal target of O2 ($P_{ET}O2[i]^T$) and the end-tidal target of CO2 ($P_{ET}CO2[i]^T$), or the desired targets must be changed. Alternatively, it may be possible to modify the rate at which the controlled gas mixture is made available to the circuit ($FG_1$) until the partial pressure of O2 in the controlled gas mixture ($P_fO2[i]$) and the partial pressure of CO2 in the controlled gas mixture ($P_fCO2[i]$) required to induce the targets are realizable with the current source gases.

Often, the rate at which the controlled gas mixture is made available to the circuit ($FG_1$) is modified to make a target end-tidal partial pressure of O2 ($P_{ET}O2[i]^T$) or a target end-tidal partial pressure of CO2 ($P_{ET}CO2[i]^T$) logistically feasible to induce. However, the rate at which the controlled gas mixture is made available to the circuit should not be increased to a rate beyond which the subject fails to consistently exhaust the supply of the controlled gas mixture in each breath. This maximal rate varies between subjects. However, it is not necessary that the rate at which the controlled gas mixture is made available to the circuit be the same in every breath. Therefore, the rate at which the controlled gas mixture is made available to the circuit may be set to some basal value for most breaths, and only increased in particular breaths in which the inducing the target end-tidal partial pressures is not logistically feasible at the basal rate of flow. The basal rate at which the controlled gas mixture is made available to the circuit should be a rate at which the subject can comfortably, without undo ventilatory effort, exhaust the supply of the controlled gas mixture in each breath. The maximal rate at which the controlled gas mixture is made available to the circuit should be the maximum rate at which the subject can consistently exhaust the supply of the controlled gas mixture in each breath with a maximal ventilatory effort. The subject may be prompted to increase their ventilatory effort in breaths where the rate at which the controlled gas mixture is made available to the circuit is increased.

Initializing the System

Let the index [0] represent the value of a variable for all breaths before the start of the sequence (all values of i≤0). To initialize the system, the subject is allowed to breathe freely, without intervention, until the measured end-tidal partial pressure of O2 ($P_{ET}CO2^M$) and the measured end-tidal partial pressure of CO2 ($P_{ET}CO2^M$) are stable—these are taken as the baseline partial pressure of O2 ($P_{ET}O2_0^M$) and the baseline partial pressure of CO2 ($P_{ET}CO2_0^M$). The measured end-tidal partial pressures are considered stable when there is less than ±5 mmHg change in the measured end-tidal partial pressure of O2 and less than ±2 mmHg change in the measured end-tidal partial pressure of CO2 over 3 consecutive breaths. The rest of the variables are initialized by assuming the whole system has equilibrated to a steady state at the baseline end-tidal partial pressures.

Assume that end-tidal partial pressures are equal to the baseline measurements:

$$P_{ET}O2[0]^T = P_{ET}O2_0^M$$

$$P_{ET}CO2[0]^T = P_{ET}CO2_0^M$$

Assume pulmonary end-capillary partial pressures are equal to end-tidal partial pressures:

$$P_pO2[0] = P_{ET}O2_0^T$$

$$P_pCO2[0] = P_{ET}CO2[0]^T$$

Calculate O2 Blood Contents Assuming Steady State:
Pulmonary End-Capillary O2 Saturation:

$$pH[0] = 6.1 + \log\left(\frac{[HCO_3]}{0.03 \cdot P_pCO2[0]}\right)$$

$$S_pO2[0] = 100 \cdot \frac{-8532.2289 \cdot z + 2121.401 \cdot z^2 - 67.073989 \cdot z^3 + z^4}{935960.87 - 31346.258 \cdot z + 2396.1674 \cdot z^2 - 67.1204406 \cdot z^3 + z^4}$$

where $$z = P_pO2[0] \cdot 10^{0.024 \cdot (37-T) + 0.4 \cdot (pH[0]-7.4) + 0.06 \cdot (\log 40 - \log P_pCO2[0])}$$

Pulmonary End-Capillary O2 Content:

$$C_pO2[0] = 1.36 \cdot Hb \cdot \frac{S_pO2[0]}{100} + 0.003 \cdot P_pO2[0]$$

Mixed-Venous O2 Content:

$$C_{MV(T)}O2[0] = C_pO2[0] - \frac{VO2}{(1-s) \cdot Q}$$

$$C_{MV}O2[0] = C_{MV(T)}O2[0]$$

Arterial O2 Content:

$$C_aO2[0] = (1-s) \cdot C_pO2[0] + s \cdot C_{MV}O2[0]$$

O2 Content of Each Compartment in the Model:

For $j = 1 \ldots n_{O2}$ $$C_VO2_j[0] = C_aO2[0] - \frac{vo2_j \cdot VO2}{q_j \cdot Q}$$

Calculate CO2 Blood Contents Assuming Steady State:
Pulmonary End-Capillary CO2 Content:

$$C_pCO2[0] = \left(1.0 - \frac{0.02924 \cdot Hb}{\left(2.244 - 0.422 \cdot \left(\frac{SpO2[0]}{100}\right)\right) \cdot (8.740 - pH[0])}\right) \cdot C_{pl}$$

$$C_{pl} = 0.0301 \cdot P_pCO2[0] \cdot (1 + 10^{pH[0]-6.10}) \cdot 2.226$$

Mixed-Venous CO2 Content:

$$C_{MV(T)}CO2[0] = C_p CO2[0] + \frac{VCO2}{(1-s)\cdot Q}$$

$$C_{MV}CO2[0] = C_{MV(T)}CO2[0]$$

Arterial CO2 Content:

$$C_a CO2[0] = (1-s)\cdot C_p CO2[0] + s\cdot C_{MV}CO2[0]$$

CO2 Content of Each Compartment in the Model:

For $k = 1 \ldots n_{CO2}$ $$C_V CO2_k[0] = C_a CO2[0] + \frac{vco2_k \cdot VCO2}{q_k \cdot Q}$$

Tuning the System

The parameters of the system can be tuned so that the measured end-tidal partial pressures of O2 ($P_{ET}O2[i]^M$) and the measured end-tidal partial pressures of CO2 ($P_{ET}CO2[i]^M$) during any sequence more closely reflect the target end-tidal partial pressures of O2 ($P_{ET}O2[i]^T$) and target end-tidal partial pressures of CO2 ($P_{ET}CO2[i]^T$). To tune the system parameters, standardized tuning sequences are run and the measured results compared to the targets. The difference between measured end-tidal partial pressures and the target end-tidal partial pressures in the standardized tuning sequences can be used to refine the estimates of some physiological parameters.

Example Tuning Sequence:

The tuning sequence sets the target end-tidal partial pressure of O2 ($P_{ET}O2[i]^T$) at 5 mmHg above the baseline end-tidal partial pressure of O2 ($P_{ET}O2_0^M$) throughout the sequence, and executes a 5 mmHg step-change in the end-tidal partial pressure of CO2 ($P_{ET}CO2[i]^T$) from 5 mmHg above the baseline end-tidal partial pressure of CO2 ($P_{ET}CO2_0^M$) to 10 mmHg above the baseline end-tidal partial pressure of CO2 in breath 30 (i=30) of the sequence.

$$P_{ET}O2[i]^T = P_{ET}O2_0^M + 5 \quad i=1 \ldots 60$$

$$P_{ET}CO2[i]^T = P_{ET}CO2_0^M + 5 \quad i=1 \ldots 29$$

$$P_{ET}CO2[i]^T = P_{ET}CO2_0^M + 10 \quad i=30 \ldots 60$$

The estimate of the functional residual capacity (FRC) can be refined as a function of the difference between the actual step change induced in the end-tidal CO2 ($P_{ET}CO2[30]^M - P_{ET}CO2[29]^M$) and the target step-change ($P_{ET}CO2[30]^T - P_{ET}CO2[29]^T = 5$) in breath 30 (i=30).

$$FRC = FRC_0 + \alpha((P_{ET}CO2[30]^M - P_{ET}CO2[29]^M) - (P_{ET}CO2[30]^T - P_{ET}CO2[29]^T))$$

$\alpha = 200$ ml/mmHg

In general, the correction factor ($\alpha$) can range from 50-500 ml/mmHg. Lower values of the correction factor will produce a more accurate estimate of the functional residual capacity (FRC) while requiring more tuning iterations. Higher values will reduce the number of tuning iterations but may cause the refined estimate of the parameter to oscillate around the optimal value.

The estimate of the overall metabolic O2 consumption (VO2) can be refined as a function of the difference between the target end-tidal partial pressure of O2 ($P_{ET}O2[60]^T$) and the measured end-tidal partial pressure of O2 ($P_{ET}O2[60]^M$) in breath 60 (i=60).

$$VO2 = VO2_0 - \beta(P_{ET}O2[60]^M - P_{ET}O2[60]^T) \quad \beta=10 \text{ ml/min/mmHg}$$

In general, the correction factor ($\beta$) can range from 5-200 ml/min/mmHg. Lower values of the correction factor will produce a more accurate estimate of the overall metabolic O2 consumption (VO2) while requiring more tuning iterations. Higher values will reduce the number of tuning iterations but may cause the refined estimate of the parameter to oscillate around the optimal value.

The estimate of the overall metabolic CO2 production (VCO2) can be refined as a function of the difference between the target end-tidal partial pressure of CO2 ($P_{ET}CO2[29]^T$) and the measured end-tidal partial pressure of CO2 ($P_{ET}CO2[29]^M$) in breath 29 (i=29).

$$VCO2 = VCO2_0 + \gamma(P_{ET}CO2[29]^M - P_{ET}CO2[29]^T) \quad \gamma=10 \text{ ml/min/mmHg}$$

Alternatively, the estimate of the overall metabolic CO2 production (VCO2) can be refined as a function of the difference between the target end-tidal partial pressure of CO2 ($P_{ET}CO2[60]^T$) and the measured end-tidal partial pressure of CO2 ($P_{ET}CO2[60]^M$) in breath 60 (i=60)

$$VCO2 = VCO2_0 + \gamma(P_{ET}CO2[60]^M - P_{ET}CO2[60]^T) \quad \gamma=10 \text{ ml/min/mmHg}$$

In general, the correction factor ($\gamma$) can range from 5-200 ml/min/mmHg. Lower values of the correction factor will produce a more accurate estimate of the overall metabolic CO2 production (VCO2) while requiring more tuning iterations. Higher values will reduce the number of tuning iterations but may cause the refined estimate of the parameter to oscillate around the optimal value.

General Requirements of a Tuning Sequence:

In breaths where the target end-tidal partial pressures of gases are transitioning between values, the estimate of the functional residual capacity (FRC) determines the magnitude of the change induced in the actual end-tidal tidal partial pressures of gases. The estimate of the overall metabolic O2 consumption (VO2) influences the induced/measured end-tidal partial pressure of O2 ($P_{ET}O2[i]^M$) in steady state. Similarly, the estimate of the overall metabolic CO2 production (VCO2) influences the induced/measured end-tidal partial pressure of CO2 ($P_{ET}CO2[i]^M$) in steady state.

It therefore follows that a difference between the measured change in the end-tidal partial pressure of O2 ($P_{ET}O2[i]^M - P_{ET}O2[i-1]^M$) and the targeted change in the end-tidal partial pressure of O2 ($P_{ET}O2[i]^T - P_{ET}O2[i-1]^T$) in breaths where the target end-tidal partial pressure of O2 is not equal to the target end-tidal partial pressure of O2 from the previous breath ($P_{ET}O2[i]^T \neq P_{ET}O2[i-1]^T$), or a difference between the measured change in the end-tidal partial pressure of CO2 ($P_{ET}CO2[i]^M - P_{ET}CO2[i-1]^M$) and the targeted change in the end-tidal partial pressure of CO2 ($P_{ET}CO2[i]^T - P_{ET}CO2[i-1]^T$) in breaths where the target end-tidal partial pressure of CO2 is not equal to the target end-tidal partial pressure of CO2 from the previous breath ($P_{ET}CO2[i]^T \neq P_{ET}CO2[i-1]^T$), reflect errors in the estimate of the functional residual capacity (FRC).

Conversely, differences between the target end-tidal partial pressure of O2 ($P_{ET}O2[i]^T$) and the measured end-tidal tidal partial pressure of O2 ($P_{ET}O2[i]^M$) in breaths at the end of a long (20 breath) period of constant target end-tidal partial pressures of O2 ($P_{ET}O2[i]^T = P_{ET}O2[i-1]^T$) reflect errors in the overall metabolic O2 consumption (VO2). It is assumed that the measured end-tidal partial pressures of O2 will have stabilized (less than ±5 mmHg change in the measured end-tidal partial pressure of O2 over 3 consecutive breaths), although not necessarily at the target end-tidal partial pressure of O2, after 20 breaths of targeting the same end-tidal partial pressures of O2. If, however, the measured end-tidal partial pressure of O2 has not stabilized after 20 breaths of targeting the same end-tidal partial pressures of O2, a longer duration of targeting the same end-tidal partial pressure of O2 should be used for tuning the overall metabolic consumption of O2.

Differences between the target end-tidal partial pressure of CO2 ($P_{ET}CO2[i]^T$) and the measured end-tidal tidal partial pressure of CO2 ($P_{ET}CO2[i]^T$) in breaths at the end of a long (20 breath) period of constant target end-tidal partial pressures of CO2 (($P_{ET}CO2[i]^T=P_{ET}CO2[i-1]^T$) reflect errors in the overall metabolic CO2 production (VCO2). It is assumed that the measured end-tidal partial pressures of CO2 will have stabilized (less than ±2 mmHg change in the measured end-tidal partial pressure of CO2 over 3 consecutive breaths), although not necessarily at the target end-tidal partial pressure of CO2, after 20 breaths of targeting the same end-tidal partial pressures of CO2. If, however, the measured end-tidal partial pressure of CO2 has not stabilized after 20 breaths of targeting the same end-tidal partial pressures of CO2, a longer duration of targeting the same end-tidal partial pressure of CO2 should be used for tuning the overall metabolic production of CO2.

The tuning sequence described above is only an example of one sequence that can be used to tune the estimates of the physiological parameters.

The functional residual capacity (FRC) can be tuned by observing the difference between the measured change in the end-tidal partial pressure of O2 ($P_{ET}O2[i]^M-P_{ET}O2[i]^M$) and the targeted change in the end-tidal partial pressure of O2 ($P_{ET}O2[i]^T \neq P_{ET}O2[i-1]^T$) in breaths where the target end-tidal partial pressure of O2 is not equal to the target end-tidal partial pressure of O2 from the previous breath ($P_{ET}O2[i]^T \neq P_{ET}O2[i-1]^T$), or a difference between the measured change in the end-tidal partial pressure of CO2 ($P_{ET}CO2[i]^M-P_{ET}CO2[i-1]^M$) and the targeted change in the end-tidal partial pressure of CO2 ($P_{ET}CO2[i]^T-P_{ET}CO2[i-1]^T$) in breaths where the target end-tidal partial pressure of CO2 is not equal to the target end-tidal partial pressure of CO2 from the previous breath ($P_{ET}CO2[i]^T \neq P_{ET}CO2[i-1]^T$). Therefore, any sequence that targets the induction of a change in the end-tidal partial pressure of O2, or a change in the end-tidal partial pressure of CO2, can be used to tune the estimate of the functional residual capacity.

The overall metabolic consumption of O2 (VO2) can be tuned by observing the difference between the target end-tidal partial pressure of O2 ($P_{ET}O2[i]^T$) and the measured end-tidal tidal partial pressure of O2 ($P_{ET}O2[i]^M$) in breaths at the end of a long (20 breath) period of constant target end-tidal partial pressures of O2 ($P_{ET}O2[i]^T=P_{ET}O2[i-1]^T$). It is assumed that the measured end-tidal partial pressures of O2 will have stabilized (less than ±5 mmHg change in the measured end-tidal partial pressure of O2 over 3 consecutive breaths), although not necessarily at the target end-tidal partial pressures of O2, after 20 breaths of targeting the same end-tidal partial pressures of O2. If, however, the measured end-tidal partial pressure of O2 has not stabilized after 20 breaths of targeting the same end-tidal partial pressures of O2, a longer duration of targeting the same end-tidal partial pressure of O2 should be used for tuning the overall metabolic consumption of O2. Therefore, any sequence that targets to maintain the end-tidal partial pressure of O2 constant for a sufficiently long duration may be used to tune the estimate of the overall metabolic consumption of O2.

The overall metabolic production of CO2 (VCO2) can be tuned by observing the difference between the target end-tidal partial pressure of CO2 ($P_{ET}CO2[i]^T$) and the measured end-tidal tidal partial pressure of CO2 ($P_{ET}CO2[i]^M$) in breaths at the end of a long (20 breath) period of constant target end-tidal partial pressures of CO2 ($P_{ET}CO2[i]^T=P_{ET}CO2[i-1]^T$). It is assumed that the measured end-tidal partial pressures of CO2 will have stabilized (less than ±2 mmHg change in the measured end-tidal partial pressure of CO2 over 3 consecutive breaths), although not necessarily at the target end-tidal partial pressure of CO2, after 20 breaths of targeting the same end-tidal partial pressures of CO2. If, however, the measured end-tidal partial pressure of CO2 has not stabilized after 20 breaths of targeting the same end-tidal partial pressures of CO2, a longer duration of targeting the same end-tidal partial pressure of CO2 should be used for tuning the overall metabolic production of CO2. Therefore, any sequence that targets to maintain the end-tidal partial pressure of CO2 constant for a sufficiently long duration may be used to tune the estimate of the overall metabolic production of CO2.

It is not required that all parameter estimates are tuned in the same sequence. Tuning of all parameters in the example sequence is done only for convenience. Different tuning sequences may be used to tune the estimates of different individual, or groups of, parameters.

Embodiments of Mass Balance Equations:
No SGD:

$$F_I X[i] = \frac{P_{ET}X[i]^T \cdot (FRC+V_T) - P_{ET}X[i-1]^T \cdot (FRC+V_D) - PB \cdot Q \cdot (1-s) \cdot T_B \cdot (C_{MV}X[i] - C_p X[i])}{(V_T - V_D) \cdot PB}$$

SGD:

$$F_I X[i] = \frac{(P_{ET}X[i]^T - P_{ET}X[i-1]^T) \cdot (FRC+V_T) + P_{ET}X[i-1]^T \cdot (FG_1 \cdot T_B) - PB \cdot Q \cdot (1-s) \cdot T_B \cdot (C_{MV}X[i] - C_p X[i])}{FG_1 \cdot T_B \cdot PB}$$

Figure 22A:
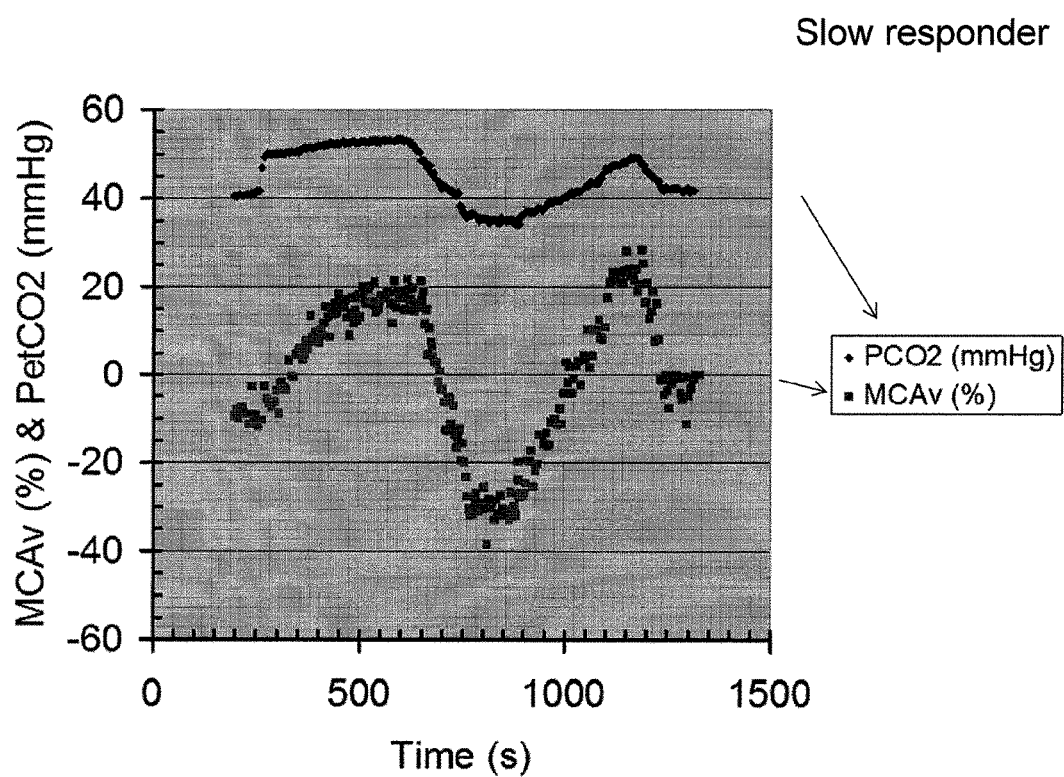
FIGS. 22a and 22b are graphical representations of changes in target end tidal values of CO2 and response—mid-cerebral artery blood flow velocity, for a slow responder and a fast responder as revealed by a ramp sequence.
Figure 22B:
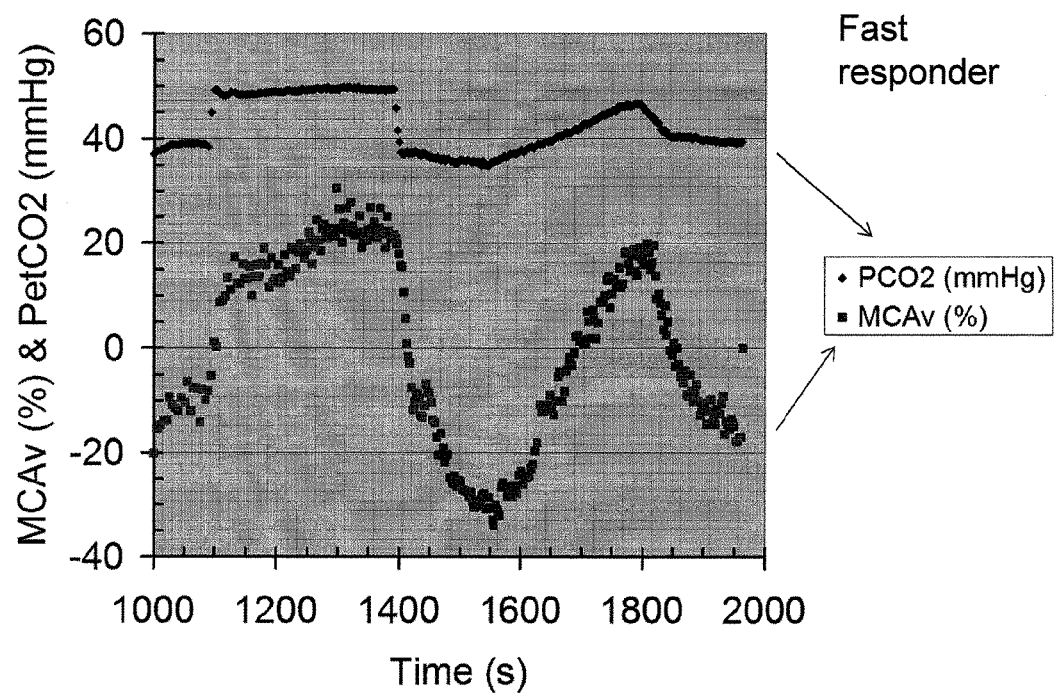

As seen in FIGS. 22a and 22b a ramp sequence reveals the sigmoidal nature of a pattern of a physiological response—mid-cerebral artery blood flow velocity—showing its sigmoidal nature over different time courses depending on whether the subject is a fast or slow responder.

Figure 23:
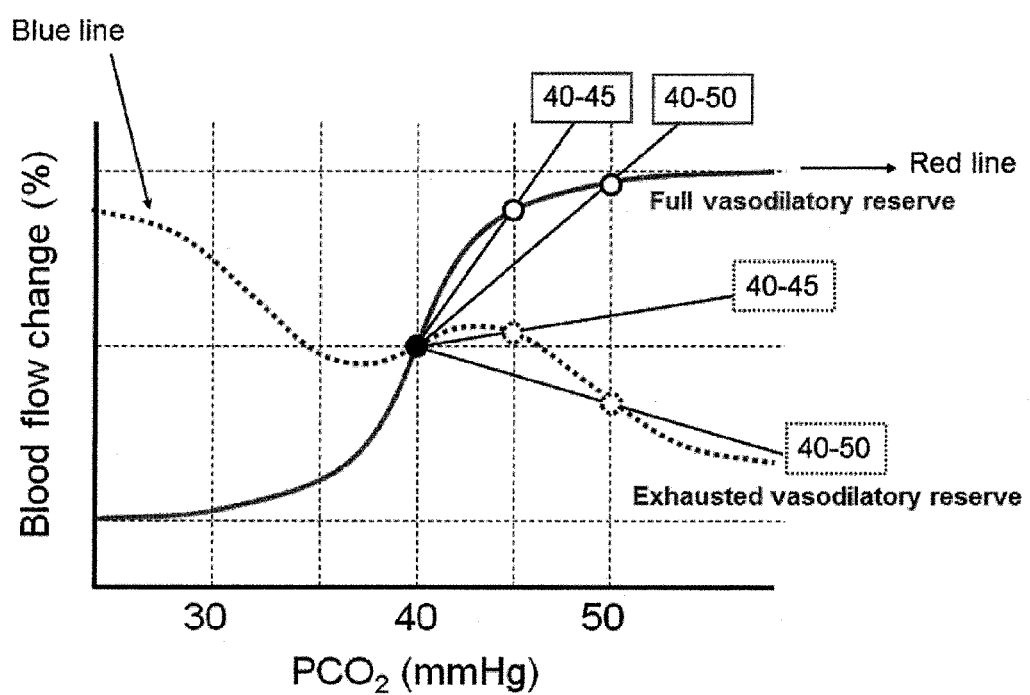

FIG. 23 blood flow responses to $PCO_2$ predicted for the model of a brain vascular territory with a partially-stenosed vessel branch and a healthy branch in parallel. Where there is some blood flow resistance upstream from the branches, it causes the partially-stenosed vessel to encroach on its vasodilatory reserve by an auto-regulatory mechanism. A vasodilatory stimulus such as in increase in arterial $CO_2$ will stimulate all vessels to dilate, but those vessels that have already dilated in response to the increase in upstream resistance have a reduced range of response. The solid red line in FIG. 23 depicts the sigmoidal response of a normal branch. The dotted blue line depicts the response of the partially stenosed vessel branch when coupled in parallel with the normal vessel branch, showing steal in hypercapnia and reverse steal in hypocapnia. The slopes of the straight lines show the predicted CVR values for $PCO_2$ stimulus ranges 40-45 and 40-50 mmHg. The filled circle marks the resting blood flow at resting $PCO_2$ and the open circles show the measured responses for a healthy territory (solid circles and line) and a territory perfused via a stenosed vessel (dotted circles and line).

FIG. 23 illustrates the sigmoidal relationship between regional blood flow and $PCO_2$ predicts that CVR in a vascular territory with adequate vasodilatory reserve will be greater for increases in $PCO_2$ from 40 to 45 mmHg vs. increases from 40 to 50 mmHg. By contrast, a vascular territory downstream from a hemodynamically significant stenosis may have a positive CVR when the $PCO_2$ change is in a range where some vasodilatory reserve is preserved, but, with a greater stimulus range such as 40-50 mmHg $PCO_2$, these vessels reach their vasodilatory limit and the continued vasodilatory capacity in other regions will induce steal.

The model outlined in FIG. 23 was investigated a comprehensive manner by using it to predict the change in CBF region by region in response to graded changes in $P_{ET}CO_2$ in a patient with steno-occlusive disease.

Figure 24:
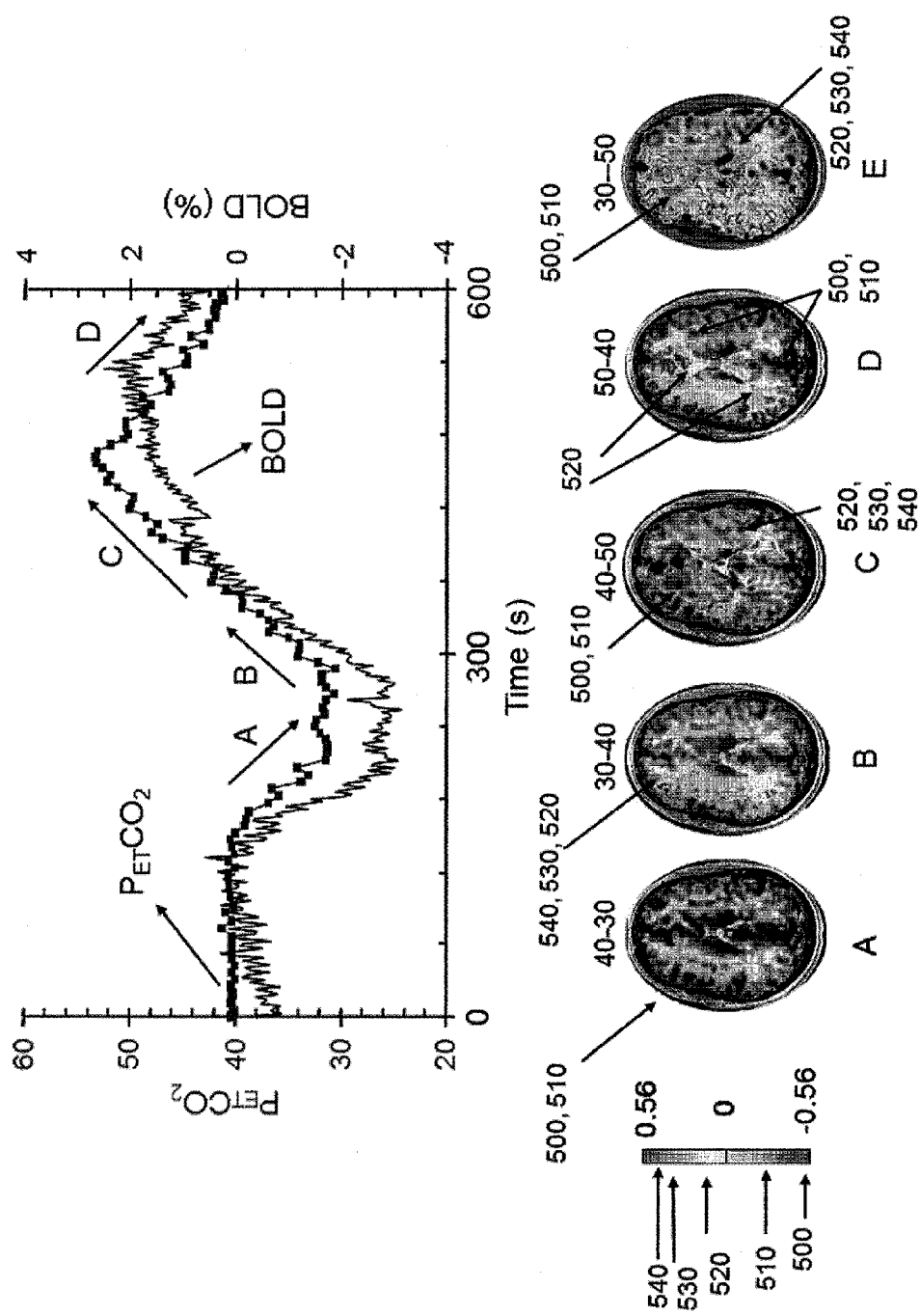

FIG. 24 shows an example of the development of steal with hypercapnia, and reverse steal (Robin Hood effect) with hypocapnia [Lassen, 1968 #16325]. Both of these conditions were observed in the same patient, confirming that steal and reverse steal are a function of the changes taking place in the parallel branches of the vascular bed with intact cerebral autoregulation. The CVR map in response to a hypercapnic change in $P_{ET}CO_2$ from 30 to 50 mmHg is shown in FIG. 24A and colour coded with the scale shown. We interpret the blue colour of the right MCA territory as signifying a vascular bed with reduced vasodilatory reserve (presumably as a result of MCA stenosis). The CVR maps for an axial slice at different $P_{ET}CO_2$ ranges for a 18 year old male patient with moya moya disease affecting the right MCA territory are divided as follows (A) CVR map calculated for a hypocapnic $P_{ET}CO_2$ change from 40 to 30 mmHg. (B) CVR map calculated for a hypercapnic $P_{ET}CO_2$ change from 30 to 40 mmHg. (C) CVR map calculated for a hypercapnic $P_{ET}CO_2$ change from 40 to 50 mmHg. (D) CVR map calculated for a hypocapnic $P_{ET}CO_2$ change from 50 to 40 mmHg. (E) CVR map calculated over the full hypercapnic $P_{ET}CO_2$ change from 30 to 50 mmHg. In this subject, inducing a reduction of $P_{ET}CO_2$ from 40 mmHg to 30 mmHg produces a robust constriction in the healthy left brain territory and a decrease in the blood flow and BOLD signal (FIG. 24, CVR A). The CVR is color coded as before, but with the convention that its sign follows the BOLD change, so the CVR map is predominantly blue in the 'normal' vascular beds. However, a careful inspection of FIG. 24 (CVR A) shows some yellow and orange colouration in the right MCA territory, indicating areas of increasing blood flow and CVR due to reverse steal, as predicted by the model demonstrated in FIG. 23. With another change in the direction of the stimulus, the hypercapnic increase in $P_{ET}CO_2$ from 30 to 40 mmHg produces a large increase in flow in the healthy left MCA region, but a lesser increase in the compromised right MCA region (FIG. 24, CVR B). Within this range of $P_{ET}CO_2$ hypercapnia, the right MCA territory demonstrates some vasodilatory reserve. Nevertheless, as predicted and illustrated in FIG. 23, further hypercapnia to 50 mmHg results in a greater steal and the CVR values are negative, and the map is coloured blue (FIG. 24, CVR C). Finally, our conceptual model predicts that withdrawal of the vasodilatory stimulus will abolish the steal and induce a reverse steal via the Robin Hood effect. Once again, this result is observed in FIG. 24 (CVR D); this CVR map is virtually the reverse image of the CVR map calculated for the full range of 30 to 50 mmHg change in $P_{ET}CO_2$ (FIG. 24, CVR E). In FIG. 24 the BOLD signal vs. time is presented for the whole brain, an average value of all voxels.

Example 1

An apparatus according to the invention was used to target end tidal gas concentrations of $CO_2$ and $O_2$ in 35 subjects. We targeted the following sequence (values attained in brackets): normocapnia (60 seconds a $PetCO_2$=40 mm Hg, SD=1 mm; $PetO_2$=100 mm Hg, SD=2 mm), Hypercapnia (60 seconds at $PetCO_2$=50 mm Hg, SD=1 mm; $PetO_2$=100 mm Hg, SD=2 mm), normocapnia (100 seconds), hypercapnia (180 seconds), and normocapnia (110 seconds). FIG. 25, comprise a partial raw data set for 6 subjects.

The content of all of the patent and scientific references herein is hereby incorporated by reference.

1. Robbins P A, Swanson G D, Howson M G. A prediction-correction scheme for forcing alveolar gases along certain time courses. J Appl Physiol 1982 May; 52(5):1353-1357. [cited 2011 Oct. 11]
2. Slessarev M, Han J, Mardimae A, Prisman E, Preiss D, Volgyesi G, Ansel C, Duffin J, Fisher J A. Prospective targeting and control of end-tidal CO2 and O2 concentrations. J. Physiol. (Lond.) 2007 June; 581(Pt 3):1207-1219. [cited 2011 Oct. 6]
3. Banzett R B, Garcia R T, Moosavi S H. Simple contrivance "clamps" end-tidal and despite rapid changes in ventilation. Journal of Applied Physiology 2000 May; 88(5):1597-1600. [cited 2011 Oct. 7]
4. Fisher J. Breathing circuits to facilitate the measurement of cardiac output during . . . [Internet]. [date unknown]; [cited 2011 Oct. 11] Available from: http://www.google.com/patents/about?id=RSqbAAAAEBAJ
5. Fisher J. Method of measuring cardiac related parameters non-invasively via the lung . . . [Internet]. [date unknown]; [cited 2011 Oct. 11] Available from: http://www.google.com/patents/about?id=QiqbAAAAEBAJ
6. Fisher J A. Method And Apparatus For Inducing And Controlling Hypoxia [Internet]. [date unknown]; [cited 2011 Oct. 11] Available from: http://www.google.com/patents/about?id=Cd7HAAAAEBAJ
7. Slessarev M. Method and Apparatus to Attain and Maintain Target End Tidal Gas Concentrations [Internet]. [date unknown]; [cited 2011 Oct. 11] Available from: http://www.google.com/patents/about?id=23XGAAAAEBAJ
8. Stenzler A. High FIO2 oxygen mask with a sequential dilution feature [Internet]. [date unknown]; [cited 2011 Oct. 11] Available from: http://www.google.com/patents/about?id=v1WIAAAAEBAJ
9. Bray J, Cragg P A, Macknight A, Mills R, Taylor D. Lecture Notes on Human Physiology. 4th ed. Wiley-Blackwell; 1999.
10. Kratz A, Lewandrowski K B. Case records of the Massachusetts General Hospital. Weekly clinicopathological exercises. Normal reference laboratory values. N. Engl. J. Med. 1998 October; 339(15):1063-1072. [cited 2011 Oct. 6]
11. Sund-Levander M, Forsberg C, Wahren L K. Normal oral, rectal, tympanic and axillary body temperature in adult men and women: a systematic literature review. Scand J Caring Sci 2002 June; 16(2):122-128. [cited 2011 Oct. 6]
12. Mackowiak P A, Wasserman S S, Levine M M. A critical appraisal of 98.6 degrees F., the upper limit of the normal body temperature, and other legacies of Carl Reinhold August Wunderlich. JAMA 1992 September; 268(12): 1578-1580. [cited 2011 Oct. 6]
13. Beutler E, Waalen J. The definition of anemia: what is the lower limit of normal of the blood hemoglobin concentration? Blood 2006 March; 107(5):1747-1750. [cited 2011 Oct. 6]
14. Peyton P J, Poustie S J, Robinson G J B, Penny D J, Thompson B. Non-invasive measurement of intrapulmonary shunt during inert gas rebreathing. Physiol Meas 2005 June; 26(3):309-316. [cited 2011 Oct. 6]
15. Peyton P J, Robinson G J B, McCall P R, Thompson B. Noninvasive measurement of intrapulmonary shunting. J. Cardiothorac. Vasc. Anesth. 2004 February; 18(1):47-52. [cited 2011 Oct. 6]
16. Hope D A, Jenkins B J, Willis N, Maddock H, Mapleson W W. Non-invasive estimation of venous admixture: validation of a new formula. Br J Anaesth 1995 May; 74(5):538-543. [cited 2011 Oct. 6]
17. Smith H L, Jones J G. Non-invasive assessment of shunt and ventilation/perfusion ratio in neonates with pulmonary failure. Arch. Dis. Child. Fetal Neonatal Ed. 2001 September; 85(2):F127-132. [cited 2011 Oct. 6]
18. Finley T N, Lenfant C, Haab P, Piiper J, Rahn H. Venous admixture in the pulmonary circulation of anesthetized dogs. J Appl Physiol 1960 May; 15:418-424. [cited 2011 Oct. 6]
19. Krowka M J, Cortese D A. Hepatopulmonary syndrome: an evolving perspective in the era of liver transplantation. Hepatology 1990 January; 11(1):138-142. [cited 2011 Oct. 6]
20. Reuter D A, Goetz A E. Measurement of cardiac output. Anaesthesist 2005 November; 54(11):1135-1151; quiz 1152-1153. [cited 2011 Oct. 6]
21. Ehlers K C, Mylrea K C, Waterson C K, Calkins J M. Cardiac output measurements. A review of current techniques and research. Ann Biomed Eng 1986; 14(3):219-239. [cited 2011 Oct. 6]
22. Geerts B F, Aarts L P, Jansen J R. Methods in pharmacology: measurement of cardiac output. Br J Clin Pharmacol 2011 March; 71(3):316-330. [cited 2011 Oct. 6]
23. Pugsley J, Lerner A B. Cardiac output monitoring: is there a gold standard and how do the newer technologies compare? Semin Cardiothorac Vasc Anesth 2010 December; 14(4):274-282. [cited 2011 Oct. 6]
24. Jegier W, Sekelj P, Auld P A, Simpson R, McGregor M. The relation between cardiac output and body size. Br Heart J 1963 July; 25:425-430. [cited 2011 Oct. 6]
25. Ross D N. Theophylline-ethylenediamine in the measurement of blood circulation time. Br Heart J 1951 January; 13(1):56-60. [cited 2011 Oct. 6]
26. Zubieta-Calleja G R, Zubieta-Castillo G, Paulev P-E, Zubieta-Calleja L. Non-invasive measurement of circulation time using pulse oximetry during breath holding in chronic hypoxia. J. Physiol. Pharmacol. 2005 September; 56 Suppl 4:251-256. [cited 2011 Oct. 6]
27. Sowton E, Bloomfield D, Jones N L, Higgs B E, Campbell E J. Recirculation time during exercise. Cardiovasc. Res. 1968 October; 2(4):341-345. [cited 2011 Oct. 6]
28. Chapman C B, Fraser R S. Studies on the effect of exercise on cardiovascular function. I. Cardiac output and mean circulation time. Circulation 1954 January; 9(1):57-62. [cited 2011 Oct. 6]
29. Mifflin M D, St Jeor S T, Hill L A, Scott B J, Daugherty S A, Koh Y O. A new predictive equation for resting energy expenditure in healthy individuals. Am. J. Clin. Nutr. 1990 February; 51(2):241-247. [cited 2011 Oct. 6]
30. Lenfant C. Time-dependent variations of pulmonary gas exchange in normal man at rest. J Appl Physiol 1967 April; 22(4):675-684. [cited 2011 Oct. 6]
31. Wanger J, Clausen J L, Coates A, Pedersen O F, Brusasco V, Burgos F, Casaburi R, Crapo R, Enright P, van der Grinten C P M, Gustafsson P, Hankinson J, Jensen R, Johnson D, Macintyre N, McKay R, Miller M R, Navajas D, Pellegrino R, Viegi G. Standardisation of the measurement of lung volumes. Eur. Respir. J. 2005 September; 26(3):511-522. [cited 2011 Oct. 6]
32. Stocks J, Quanjer P H. Reference values for residual volume, functional residual capacity and total lung capacity. ATS Workshop on Lung Volume Measurements. Official Statement of The European Respiratory Society. Eur. Respir. J. 1995 March; 8(3):492-506. [cited 2011 Oct. 6]
33. Arnold J H, Thompson J E, Arnold L W. Single breath CO2 analysis: description and validation of a method. Crit. Care Med. 1996 January; 24(1):96-102. [cited 2011 Oct. 6]
34. Heller H, Könen-Bergmann M, Schuster K D. An algebraic solution to dead space determination according to Fowler's graphical method. Comput. Biomed. Res. 1999 April; 32(2):161-167. [cited 2011 Oct. 6]
35. Williams E M, Hamilton R M, Sutton L, Viale J P, Hahn C E. Alveolar and dead space volume measured by oscillations of inspired oxygen in awake adults. Am. J. Respir. Crit. Care Med. 1997 December; 156(6):1834-1839. [cited 2011 Oct. 6]
36. Hart M C, Orzalesi M M, Cook C D. Relation between anatomic respiratory dead space and body size and lung volume. Journal of Applied Physiology 1963 May; 18(3): 519-522. [cited 2011 Oct. 6]
37. Ito S, Mardimae A, Han J, Duffin J, Wells G, Fedorko L, Minkovich L, Katznelson R, Meineri M, Arenovich T, Kessler C, Fisher J A. Non-invasive prospective targeting of arterial PCO2 in subjects at rest. J. Physiol. (Lond.) 2008 August; 586(Pt 15):3675-3682. [cited 2011 Oct. 6]
38. Somogyi R B, Vesely A E, Preiss D, Prisman E, Volgyesi G, Azami T, Iscoe S, Fisher J A, Sasano H. Precise control of end-tidal carbon dioxide levels using sequential rebreathing circuits. Anaesth Intensive Care 2005 December; 33(6):726-732. [cited 2011 Oct. 6]
39. Fierstra J, Machina M, Battisti-Charbonney A, Duffin J, Fisher J A, Minkovich L. End-inspiratory rebreathing reduces the end-tidal to arterial PCO2 gradient in mechanically ventilated pigs. Intensive Care Med 2011 September; 37(9):1543-1550. [cited 2011 Oct. 6]
40. Jones N L, Robertson D G, Kane J W, Campbell E J. Effect of PCO2 level on alveolar-arterial PCO2 difference during rebreathing. J Appl Physiol 1972 June; 32(6):782-787. [cited 2011 Oct. 6]
41. Raine J M, Bishop J M. A-a difference in O2 tension and physiological dead space in normal man. J Appl Physiol 1963 March; 18:284-288. [cited 2011 Oct. 6]
42. Kelman G R. Digital computer subroutine for the conversion of oxygen tension into saturation. J Appl Physiol 1966 July; 21(4):1375-1376. [cited 2011 Oct. 6]
43. Wheeler D S, Wong H R, Shanley T P. Pediatric Critical Care Medicine: Basic Science and Clinical Evidence. 1st ed. Springer; 2007.
44. Burnett R W, Noonan D C. Calculations and correction factors used in determination of blood pH and blood gases. Clin. Chem. 1974 December; 20(12):1499-1506. [cited 2011 Oct. 6]

45. Loeppky J A, Luft U C, Fletcher E R. Quantitative description of whole blood CO2 dissociation curve and Haldane effect. Respir Physiol 1983 February; 51(2):167-181. [cited 2011 Oct. 6]
46. Douglas A R, Jones N L, Reed J W. Calculation of whole blood CO2 content. J. Appl. Physiol. 1988 July; 65(1): 473-477. [cited 2011 Oct. 6]
47. Kelman G R. Digital computer procedure for the conversion of PCO2 into blood CO2 content. Respir Physiol 1967 August; 3(1):111-115. [cited 2011 Oct. 6]
48. Olszowka A J, Farhi L E. A system of digital computer subroutines for blood gas calculations. Respir Physiol 1968 March; 4(2):270-280. [cited 2011 Oct. 6]
49. Cherniack N S, Longobardo G S. Oxygen and carbon dioxide gas stores of the body. Physiol. Rev. 1970 April; 50(2):196-243. [cited 2011 Oct. 6]
50. Cherniack N S, Longobardo G S, Palermo F P, Heymann M. Dynamics of oxygen stores changes following an alteration in ventilation. J Appl Physiol 1968 June; 24(6): 809-816. [cited 2011 Oct. 6]
51. Farhi L E, Rahn H. Dynamics of changes in carbon dioxide stores. Anesthesiology 1960 December; 21:604-614. [cited 2011 Oct. 6]
52. Cherniack N S, Longobardo G S, Staw I, Heymann M. Dynamics of carbon dioxide stores changes following an alteration in ventilation. J Appl Physiol 1966 May; 21(3): 785-793. [cited 2011 Oct. 6]

PUBMED CROSS-REFERENCED REFERENCES

1: Mutch W A, Patel S R, Shahidi A M, Kulasekara S I, Fisher J A, Duffin J, Hudson C. Cerebral oxygen saturation: graded response to carbon dioxide with isoxia and graded response to oxygen with isocapnia. PLoS One. 2013; 8(2):e57881. doi: 10.1371/journal.pone.0057881. Epub 2013 Feb. 28. PubMed PMID: 23469096; PubMed Central PMCID: PMC3585256.
2: Tancredi F B, Gauthier C J, Madjar C, Bolar D S, Fisher J A, Wang D J, Hoge R D. Comparison of pulsed and pseudocontinuous arterial spin-labeling for measuring CO2-induced cerebrovascular reactivity. J Magn Reson Imaging. 2012 August; 36(2):312-21. doi: 10.1002/jmri.23658. Epub 2012 Apr. 27. PubMed PMID: 22544711.
3: Han J S, Abou-Hamden A, Mandell D M, Poublanc J, Crawley A P, Fisher J A, Mikulis D J, Tymianski M. Impact of extracranial-intracranial bypass on cerebrovascular reactivity and clinical outcome in patients with symptomatic moyamoya vasculopathy. Stroke. 2011 November; 42(11):3047-54. doi: 10.1161/STROKEAHA.111.615955. Epub 2011 Sep. 8. PubMed PMID: 21903951.
4: Fierstra J, Spieth S, Tran L, Conklin J, Tymianski M, ter Brugge K G, Fisher J A, Mikulis D J, Krings T. Severely impaired cerebrovascular reserve in patients with cerebral proliferative angiopathy. J Neurosurg Pediatr. 2011 September; 8(3):310-5. doi: 10.3171/2011.6.PEDS1170. PubMed PMID: 21882924.
5: Han J S, Mikulis D J, Mardimae A, Kassner A, Poublanc J, Crawley A P, deVeber G A, Fisher J A, Logan W J. Measurement of cerebrovascular reactivity in pediatric patients with cerebral vasculopathy using blood oxygen level-dependent MRI. Stroke. 2011 May; 42(5):1261-9. doi: 10.1161/STROKEAHA.110.603225. Epub 2011 Apr. 14. PubMed PMID: 21493907.
6: Fierstra J, Conklin J, Krings T, Slessarev M, Han J S, Fisher J A, Terbrugge K, Wallace M C, Tymianski M, Mikulis D J. Impaired peri-nidal cerebrovascular reserve in seizure patients with brain arteriovenous malformations. Brain. 2011 January; 134(Pt 1):100-9. doi: 10.1093/brain/awq286. Epub 2010 Nov. 24. PubMed PMID: 21109501.
7: Winter J D, Fierstra J, Dorner S, Fisher J A, St Lawrence K S, Kassner A. Feasibility and precision of cerebral blood flow and cerebrovascular reactivity MRI measurements using a computer-controlled gas delivery system in an anesthetised juvenile animal model. J Magn Reson Imaging. 2010 November; 32(5):1068-75. doi: 10.1002/jmri.22230. PubMed PMID: 21031510.
8: Mark C I, Fisher J A, Pike G B. Improved fMRI calibration: precisely controlled hyperoxic versus hypercapnic stimuli. Neuroimage. 2011 January 15; 54(2): 1102-11. doi: 10.1016/j.neuroimage.2010.08.070. Epub 2010 Sep. 7. PubMed PMID: 20828623.
9: Mark C I, Slessarev M, Ito S, Han J, Fisher J A, Pike G B. Precise control of end-tidal carbon dioxide and oxygen improves BOLD and ASL cerebrovascular reactivity measures. Magn Reson Med. 2010 September; 64(3):749-56. doi: 10.1002/mrm.22405. PubMed PMID: 20648687.
10: Battisti A, Fisher J A, Duffin J. Measuring the hypoxic ventilatory response. Adv Exp Med Biol. 2010; 669:221-4. doi: 10.1007/978-1-4419-5692-7_44. PubMed PMID: 20217353.
11: Heyn C, Poublanc J, Crawley A, Mandell D, Han J S, Tymianski M, terBrugge K, Fisher J A, Mikulis D J. Quantification of cerebrovascular reactivity by blood oxygen level-dependent MR imaging and correlation with conventional angiography in patients with Moyamoya disease. AJNR Am J Neuroradiol. 2010 May; 31(5):862-7. doi: 10.3174/ajnr.A1922. Epub 2010 Jan. 14. PubMed PMID: 20075092.
12: Cohen-Adad J, Gauthier C J, Brooks J C, Slessarev M, Han J, Fisher J A, Rossignol S, Hoge R D. BOLD signal responses to controlled hypercapnia in human spinal cord. Neuroimage. 2010 Apr. 15; 50(3):1074-84. doi: 10.1016/j.neuroimage.2009.12.122. Epub 2010 Jan. 11. PubMed PMID: 20060914.
13: Venkataraman S T, Hudson C, Rachmiel R, Buys Y M, Markowitz S N, Fisher J A, Trope G E, Flanagan J G. Retinal arteriolar vascular reactivity in untreated and progressive primary open-angle glaucoma. Invest Ophthalmol Vis Sci. 2010 April; 51(4):2043-50. doi: 10.1167/iovs.09-3630. Epub 2009 Nov. 11. PubMed PMID: 19907031.
14: Han J S, Mandell D M, Poublanc J, Mardimae A, Slessarev M, Jaigobin C, Fisher J A, Mikulis D J. BOLD-MRI cerebrovascular reactivity findings in cocaine-induced cerebral vasculitis. Nat Clin Pract Neurol. 2008 November; 4(11):628-32. doi: 10.1038/ncpneuro0918. Epub 2008 Oct. 7. PubMed PMID: 18839005.
15: Mandell D M, Han J S, Poublanc J, Crawley A P, Kassner A, Fisher J A, Mikulis D J. Selective reduction of blood flow to white matter during hypercapnia corresponds with leukoaraiosis. Stroke. 2008 July; 39(7):1993-8. doi: 10.1161/STROKEAHA.107.501692. Epub 2008 May 1. PubMed PMID: 18451357.
16: Ito S, Mardimae A, Han J, Duffin J, Wells G, Fedorko L, Minkovich L, Katznelson R, Meineri M, Arenovich T, Kessler C, Fisher J A. Non-invasive prospective targeting of arterial P(CO2) in subjects at rest. J Physiol. 2008 Aug. 1; 586(Pt 15):3675-82. doi: 10.1113/jphysiol.2008.154716. Epub 2008 Jun. 19. PubMed PMID: 18565992; PubMed Central PMCID: PMC2538829.

The content of all the references in this document is hereby incorporated by reference.

What is claimed is:

1. A system for targeting an end tidal partial pressure of at least one gas X ($PetX^T$) in a mammalian subject's lung, comprising:
   (1) a gas delivery device configured for connection to a breathing circuit;
   (2) a control system;
   (3) a measurement system configured to obtain a value which represents an approximation of the partial pressure of the at least one gas X in a subject's arterial blood after gas exchange in a previous breath [i−1];
   wherein the control system is configured, with respect to a series of respective breaths [i] of respective sizes determined by the subject spontaneously, to:
   (A) make available for inspiration to the subject, a first gas in a first part of a respective breath [i], the volume of the first gas selected such that a neutral second gas is arranged for inspiration in a second part of the respective breath [i], wherein the volume of neutral gas arranged for inspiration in the respective breath [i] at least equals and preferably exceeds the subject's anatomic dead space volume; and
   (B) use a feedback control algorithm to:
   (i) obtain, on a breath by breath basis, the measured value at least approximately corresponding to the arterial partial pressure of gas X after gas exchange in a previous breath ([i−1]);
   (ii) based on the measured value, compute an error signal with respect to the $PetX^T$ for the respective breath [i]; and
   (iii) generate a control signal based on the error signal that controls an amount of gas X delivered for inspiration by the subject in the first gas to target $PetX^T$ for the respective breath [i], the control signal signalling the gas delivery apparatus to deliver for inspiration in the first part of the respective breath [i], the amount of gas X that targets $PetX^T$ for the respective breath [i].

2. A system according to claim 1, wherein the measured value is the concentration of the at least one gas X in a subject's expired end tidal gas after gas exchange in breath [i−1].

3. A system according to claim 1, wherein the neutral gas has a partial pressure of gas X that equals the end tidal partial pressure of gas X targeted for the respective breath [i] or the end tidal partial pressure of gas X measured or computed for a previous breath, preferably an immediately preceding breath [i−1].

4. A system according to claim 1, wherein the control system is implemented by a computer, the computer configured to provide control signals to one or more rapid flow controllers.

5. A system according to claim 1, wherein the gas delivery device is a gas blender and wherein the measurement system includes at least one flow sensor positioned to measure flow of an inspiratory gas stream to the subject, and wherein the gas blender is controlled to add a varying amount of gas X to the inspiratory gas stream based on measurements obtained from the flow sensor to deliver the respective amounts of gas X required to be inspired by the subject to target the respective $PetX^T$ for the series of respective breaths [i].

6. A system according to claim 1, wherein the breathing circuit is a sequential gas delivery (SGD) circuit.

7. A system according to claim 1, wherein the control system implements a virtual SGD circuit.

8. A system according to claim 1, wherein the gas X is carbon dioxide or oxygen.

9. A system according to claim 1, wherein the control system is configured to contemporaneously target for the respective breath [i], a target end tidal concentration of gas X and at least a gas Y.

10. A system as claimed in claim 9, wherein the gas X is carbon dioxide and the gas Y is oxygen.

11. A system according to claim 1, wherein the system is configured to be used when the subject is hyperventilating.

12. A system according to claim 1, wherein the amount of gas X required to be delivered in the first inspired gas to target the end tidal partial pressure of gas X for the respective breath [i] is determined prospectively based on a predictive algorithm, and wherein the error signal is added to the signal generated by the predictive algorithm.

13. A system according to claim 1, wherein the feedback control algorithm is selected from a group comprising a PD, a PI and a PID control algorithm.

* * * * *